(12) United States Patent
Helgerson et al.

(10) Patent No.: US 9,737,342 B2
(45) Date of Patent: Aug. 22, 2017

(54) SYSTEM AND METHOD FOR FACET JOINT REPLACEMENT

(71) Applicant: GLOBUS MEDICAL, INC., Audubon, PA (US)

(72) Inventors: Joel R. Helgerson, Erie, CO (US); Daniel J. Triplett, Providence, UT (US); Andrew R. Fauth, River Heights, UT (US); David M. Skinlo, North Logan, UT (US); E. Marlowe Goble, Logan, UT (US); Daniel E. Gerbec, Logan, UT (US)

(73) Assignee: Globus Medical, Inc., Audubon, PA (US)

( * ) Notice: Subject to any disclaimer, the term of this patent is extended or adjusted under 35 U.S.C. 154(b) by 86 days.

(21) Appl. No.: 14/703,160

(22) Filed: May 4, 2015

(65) Prior Publication Data
US 2015/0230826 A1  Aug. 20, 2015

Related U.S. Application Data

(63) Continuation of application No. 13/559,159, filed on Jul. 26, 2012, now Pat. No. 9,050,145, which is a continuation of application No. 12/201,128, filed on Aug. 29, 2008, now Pat. No. 8,252,027, which is a continuation-in-part of application No. 12/104,726, filed on Apr. 17, 2008, now Pat. No. 8,353,933, and a continuation-in-part of application No. 12/104,855,
(Continued)

(51) Int. Cl.
*A61B 17/70* (2006.01)

(52) U.S. Cl.
CPC .......... *A61B 17/705* (2013.01); *A61B 17/704* (2013.01); *A61B 17/707* (2013.01); *A61B 17/7007* (2013.01); *A61B 17/7011* (2013.01); *A61B 17/7035* (2013.01); *A61B 17/7041* (2013.01); *A61B 17/7064* (2013.01)

(58) Field of Classification Search
CPC ............ A61B 17/7062; A61B 17/7064; A61B 17/7067; A61B 17/7068; A61B 2017/7073
USPC .................................................. 606/246-279
See application file for complete search history.

(56) References Cited

U.S. PATENT DOCUMENTS

| 2005/0131537 A1* | 6/2005 | Hoy ..................... A61F 2/30771 623/17.11 |
| 2006/0058791 A1* | 3/2006 | Broman ................ A61B 17/686 623/17.16 |
| 2006/0149229 A1* | 7/2006 | Kwak ................. A61B 17/7023 606/256 |

* cited by examiner

*Primary Examiner* — Ellen C Hammond
*Assistant Examiner* — Christina Negrellirodrigue

(57) ABSTRACT

A facet joint replacement system includes an inferior implant with an inferior articular surface, a superior implant with a superior articular surface and may include a crosslink extending across a vertebral sagittal plane. The inferior implant may comprise an inferior strut, and a polyaxially adjustable, lockable mechanism which may couple the inferior articular surface with a first end of the inferior strut, and couple the inferior articular surface with the crosslink. A second end of the inferior strut may be secured to a polyaxially adjustable, lockable fixation assembly securable in a vertebra. The superior implant may be secured to a polyaxially adjustable lockable fixation assembly securable in a vertebra. The positions of the inferior articular surface and the first end of the inferior strut are independently translatable along a medial-lateral axis of the vertebra prior to lockout by the lockable mechanism. The crosslink may be placed into the lockable mechanism from a posterior approach.

19 Claims, 47 Drawing Sheets

Related U.S. Application Data filed on Apr. 17, 2008, now Pat. No. 8,333,789, which is a continuation-in-part of application No. 11/972,158, filed on Jan. 10, 2008, now Pat. No. 8,900,273, said application No. 12/104,726 is a continuation-in-part of application No. 11/972,158.

(60) Provisional application No. 60/884,233, filed on Jan. 10, 2007, provisional application No. 60/912,323, filed on Apr. 17, 2007, provisional application No. 60/950,012, filed on Jul. 16, 2007, provisional application No. 60/950,021, filed on Jul. 16, 2007, provisional application No. 60/950,031, filed on Jul. 16, 2007, provisional application No. 60/950,038, filed on Jul. 16, 2007, provisional application No. 60/957,505, filed on Aug. 23, 2007, provisional application No. 60/968,324, filed on Aug. 27, 2007, provisional application No. 60/968,925, filed on Aug. 30, 2007, provisional application No. 60/975,731, filed on Sep. 28, 2007, provisional application No. 60/984,434, filed on Nov. 1, 2007, provisional application No. 60/984,428, filed on Nov. 1, 2007, provisional application No. 60/984,594, filed on Nov. 1, 2007, provisional application No. 60/984,798, filed on Nov. 2, 2007, provisional application No. 60/984,814, filed on Nov. 2, 2007, provisional application No. 60/984,983, filed on Nov. 2, 2007, provisional application No. 61/014,344, filed on Dec. 17, 2007, provisional application No. 61/015,866, filed on Dec. 21, 2007, provisional application No. 61/015,876, filed on Dec. 21, 2007, provisional application No. 61/015,886, filed on Dec. 21, 2007, provisional application No. 61/015,840, filed on Dec. 21, 2007, provisional application No. 61/023,927, filed on Jan. 28, 2008, provisional application No. 61/033,473, filed on Mar. 4, 2008, provisional application No. 61/040,041, filed on Mar. 27, 2008, provisional application No. 61/042,896, filed on Apr. 7, 2008, provisional application No. 61/045,526, filed on Apr. 16, 2008.

SYSTEM AND METHOD FOR FACET JOINT REPLACEMENT

CROSS REFERENCE TO RELATED APPLICATIONS

This Patent Application is a continuation application claiming priority to U.S. patent application Ser. No. 13/559,159, filed Jul. 26, 2012, which is a continuation application claiming priority to U.S. patent application Ser. No. 12/201,128, filed Aug. 29, 2008, now issued as U.S. Pat. No. 8,252,027, which is a continuation-in-part application of each of the following:

U.S. application Ser. No. 12/104,726, filed Apr. 17, 2008, now U.S. Pat. No. 8,353,933, and is entitled FACET JOINT REPLACEMENT; and U.S. application Ser. No. 12/104,855, filed Apr. 17, 2008, now U.S. Pat. No. 8,333,789, and is entitled FACET JOINT REPLACEMENT.

Each of these is a continuation-in-part of the following:

U.S. application Ser. No. 11/972,158, filed Jan. 10, 2008, now U.S. Pat. No. 8,900,273, and is entitled TAPER-LOCKING FIXATION SYSTEM, which claims the benefit of the following:

U.S. Provisional Patent Application No. 60/884,233, filed Jan. 10, 2007, and is entitled TAPER-LOCKING ROD FIXATION SYSTEM;

U.S. Provisional Application No. 60/912,323, filed Apr. 17, 2007, and is entitled AFRS MULTI-LEVEL IMPLANT SYSTEM;

U.S. Provisional Application No. 60/950,012, filed Jul. 16, 2007, and is entitled INFERIOR FACET IMPLANT HOLDER;

U.S. Provisional Application No. 60/950,021, filed Jul. 16, 2007, and is entitled MONORAIL INSTRUMENT GUIDANCE SYSTEM FOR LUMBAR SPINAL SURGERY;

U.S. Provisional Application No. 60/950,031, filed Jul. 16, 2007, and is entitled LINEAR POLYAXIAL LOCKING MECHANISM WITH TOOL;

U.S. Provisional Application No. 60/950,038, filed Jul. 16, 2007, and is entitled MOBILE INFERIOR FACET BEARING WITH SUPERIOR CLIP;

U.S. Provisional Application No. 60/957,505, filed Aug. 23, 2007, and is entitled DYNAMIC STABILIZATION AND STATIC FIXATION OPTIONS FOR FACET REPLACEMENT PROSTHESIS;

U.S. Provisional Application No. 60/968,324, filed Aug. 27, 2007, and is entitled INTERVERTEBRAL DISC IMPLANT WITH FACET MOTION CONSTRAINTS;

U.S. Provisional Application No. 60/968,925, filed Aug. 30, 2007, and is entitled SYSTEMS AND METHODS FOR LESS INVASIZE FACET JOINT REPLACEMENT;

U.S. Provisional Application No. 60/975,731, filed Sep. 28, 2007, and is entitled MONOLITHIC INFERIOR IMPLANT STRUT WITH INTEGRAL CROSS LINK CLAMP;

U.S. Provisional Application No. 60/984,434, filed Nov. 1, 2007, and is entitled SUPERIOR INSTRUMENTS;

U.S. Provisional Application No. 60/984,428, filed Nov. 1, 2007, and is entitled CROSS LINK CLAMP;

U.S. Provisional Application No. 60/984,594, filed Nov. 1, 2007, and is entitled LOW PROFILE POLYAXIAL FACET IMPLANT;

U.S. Provisional Application No. 60/984,798, filed Nov. 2, 2007, and is entitled LOW PROFILE POLYAXIAL FACET IMPLANT;

U.S. Provisional Application No. 60/984,814, filed Nov. 2, 2007, and is entitled HINGED EYELET SCREW;

U.S. Provisional Application No. 60/984,983, filed Nov. 2, 2007, and is entitled ADJUSTABLE FACET IMPLANT BASE PIECE;

U.S. Provisional Application No. 61/014,344, filed Dec. 17, 2007, and is entitled INFERIOR STRUT UPDATE;

U.S. Provisional Application No. 61/015,866, filed Dec. 21, 2007, and is entitled INTERVERTEBRAL DISC IMPLANT WITH FACET MOTION CONSTRAINTS INCLUDING POSTERIOR COMBINATION;

U.S. Provisional Application No. 61/015,876, filed Dec. 21, 2007, and is entitled INTERVERTEBRAL DISC IMPLANT WITH FACET MOTION CONSTRAINTS AND METHODS FOR IMPLANT ALIGNMENT;

U.S. Provisional Application No. 61/015,886, filed Dec. 21, 2007, and is entitled EYELET PEDICLE SCREW WITH MULTI-AXIAL FIXATION; and U.S. Provisional Application No. 61/015,840, filed Dec. 21, 2007, and is entitled CERVICAL PLATE WITH FACET MOTION CONTROL.

U.S. Ser. No. 12/201,128 also claims the benefit of the following, which are incorporated herein by reference:

U.S. Provisional Application No. 61/023,927, filed Jan. 28, 2008, and is entitled AFRS GENERATION II INSTRUMENTS;

U.S. Provisional Application No. 61/033,473, filed Mar. 4, 2008, and is entitled TOP LOADING RECEIVER FOR AN ADJUSTABLE FACET REPLACEMENT;

U.S. Provisional Application No. 61/040,041, filed Mar. 27, 2008, and is entitled FACET JOINT REPLACEMENT;

U.S. Provisional Application No. 61/042,896, filed Apr. 7, 2008, and is entitled SPINAL FIXATION ON AN IMPLANT BASE; and U.S. Provisional Application No. 61/045,526, filed Apr. 16, 2008, and is entitled INFERIOR BASE-SPLIT CLAMP AND MULTI-LEVEL SPLIT CLAMP.

All of the foregoing are incorporated herein by reference.

FIELD OF THE INVENTION

The present invention relates to spinal surgery. More specifically, the invention relates to replacement of natural vertebral facet joints with implantable artificial facet joint replacements.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to replace natural vertebral facet joints with implantable artificial facet joint prostheses in a manner that provides a high degree of implant adjustability, simplicity, and ease of use.

In this application, "polyaxial" rotation is rotation that can occur about at least two axes that are not parallel to each other. "Lock-out" or "lock-down" between two or more component parts refers to a state in which movement of any component part is prevented by frictional, compression, expansion, or other forces. A "taper-lock connector" refers to a locking mechanism that uses a taper to effect locking.

Figure 1:
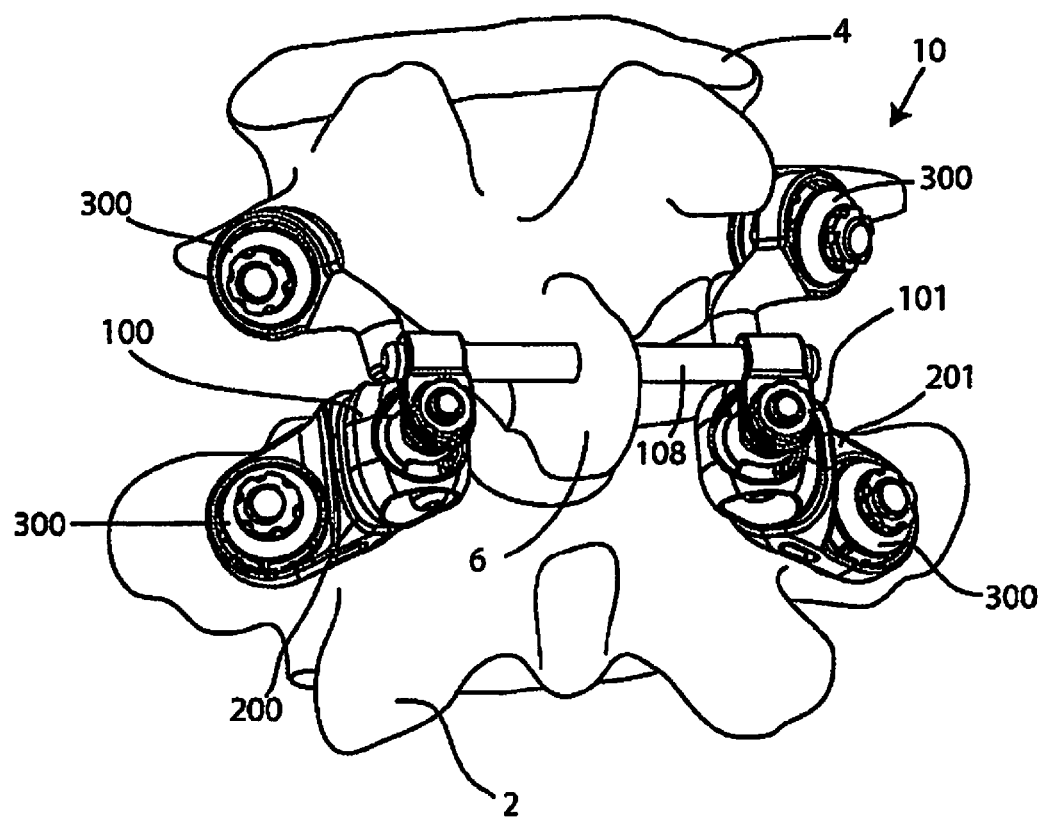
FIG. 1 is a perspective view of a portion of a spine with a bi-lateral facet joint replacement system implanted into two adjacent vertebrae.

Referring to FIG. 1, a perspective view depicts a portion of a spine including a first vertebra 2 and a second vertebra 4. A system 10 of bi-lateral facet joint replacements joined by a crosslink rod passing through a spinous process 6 is implanted in the vertebrae. On the left side of the vertebrae, an inferior facet joint implant 100 is secured to a fixation assembly 300 implanted in vertebra 4. Together the inferior facet joint implant 100 and fixation assembly 300 form inferior facet joint prosthesis 11. A superior facet joint implant 200 is secured to a fixation assembly 300 implanted in vertebra 2, and together the superior facet joint implant 200 and fixation assembly 300 form superior facet joint prosthesis 12. On the right side of the vertebrae, an inferior facet joint implant 101 is secured to a fixation assembly 300 implanted in vertebra 4, and a superior facet joint implant 201 is secured to a fixation assembly 200 implant in vertebra 2. It is appreciated that many of the facet joint replacement prostheses, implants and fixation assemblies described herein may each be configured in a "right" or a "left" configuration to be implanted on the right or left lateral side of the vertebrae. However, in most cases, only one (right or left) configuration will be described, and it is assumed that the other (right or left) configuration is a mirror-image of the one described. It is also appreciated that the implants described herein may be implanted bi-laterally as in FIG. 1, or unilaterally, if desired.

Figure 2:
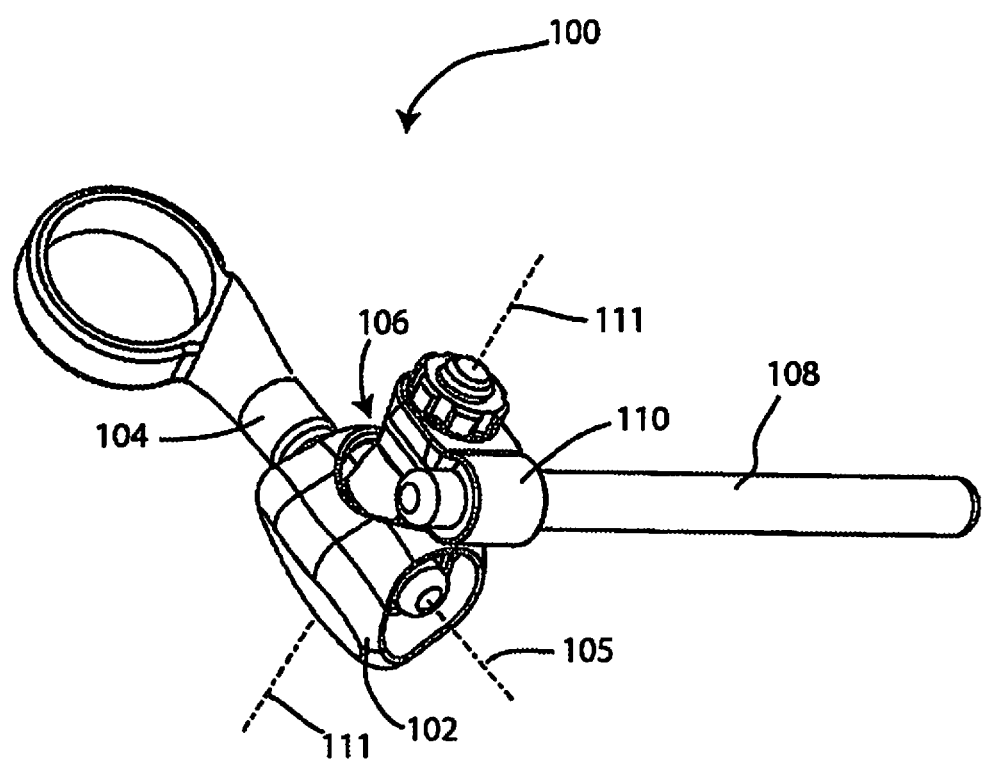
FIG. 2 is perspective view of an inferior facet joint implant coupled to a crosslink rod.

Referring to FIG. 2, a perspective view depicts polyaxially adjustable left inferior facet joint implant 100. Inferior facet joint implant 100 comprises an inferior articular body 102, an inferior strut 104, and an attachment mechanism 106 which adjustably secures the articular body to the inferior strut. The attachment mechanism 106 has an adjustable configuration in which the inferior articular body 102 can rotate relative to the inferior strut 104 about three orthogonal axes, and it has a locked configuration in which the inferior articular body 102 is rigidly secured to inferior strut 104. A crosslink rod 108 may optionally be secured to the implant 100 by a split clamp 110. The attachment mechanism 106 may be actuated to simultaneously lock the crosslink rod 108 in the split clamp 110 as the inferior articular body 102 is locked to the inferior strut 104. A clamp axis 111 extends longitudinally through the attachment mechanism. A strut axis 105 extends longitudinally along the inferior strut 104.

Figure 3:
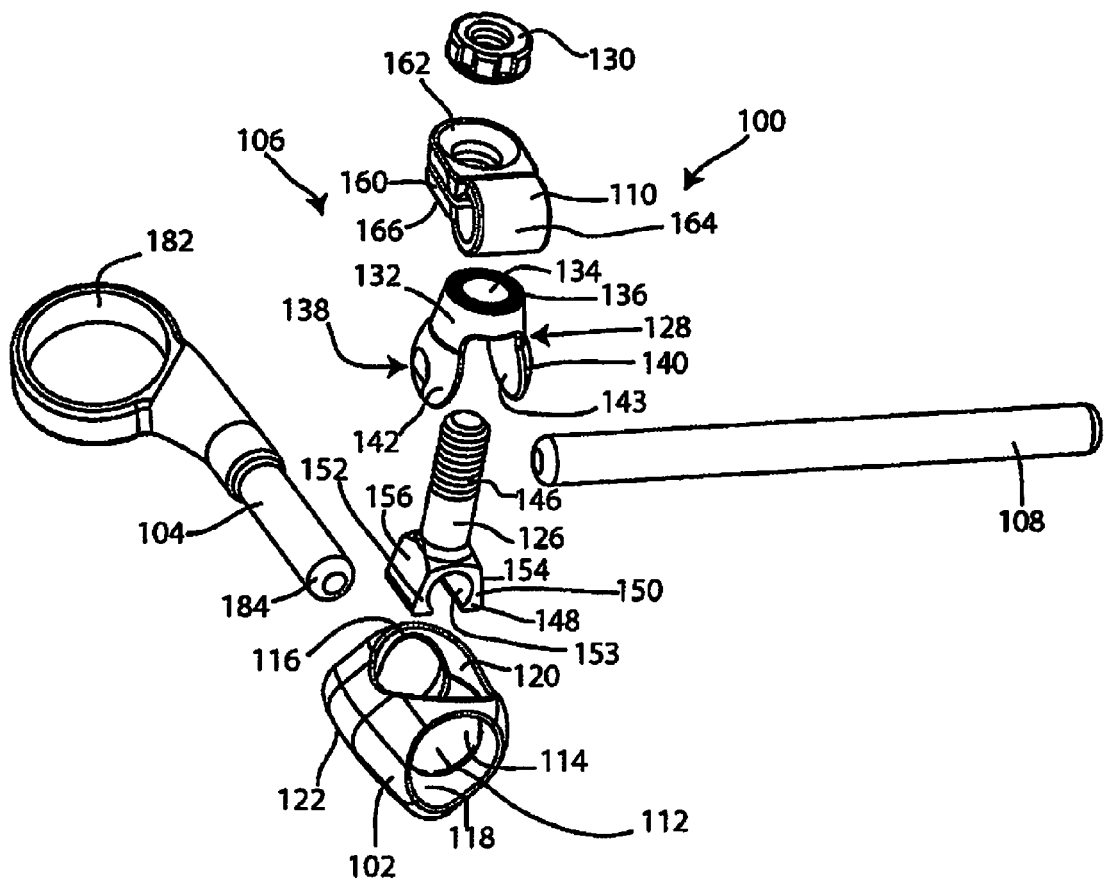
FIG. 3 is an exploded view of the inferior facet joint implant and crosslink rod of FIG. 2.

Referring to FIG. 3, an exploded perspective view illustrates the component parts which may comprise the left inferior facet joint implant 100. The inferior articular body 102 is shell-like and has a substantially concave interior cavity 112 which is defined by an interior wall 114. A first chamfered opening 116 and a second chamfered opening 118 in the inferior articular body 102 create a passageway through which a portion of the inferior strut may fit when the implant is assembled. An attachment post opening 120, which may also be chamfered, is situated orthogonal to the first and second chamfered openings 116, 118. The chamfered openings may provide additional range of motion between the inferior articular body and the inferior strut 104 as the articular body 102 is polyaxially adjusted prior to locking down. An inferior articular surface 122 is located on the exterior of the inferior articular body 102, and is shaped to replace a natural inferior articular surface of a vertebra. Inferior facet implant 100 may be implanted in conjunction with a superior facet implant, wherein the inferior articular surface 122 articulates with an artificial superior facet articular surface. Alternately, inferior facet implant 100 may be implanted such that the inferior articular surface 122 articulates with a natural superior facet articular surface. In either case, the articulation between superior and inferior articular surfaces, whether natural or artificial, provides preservation of a level of natural spinal motion.

Figure 4:
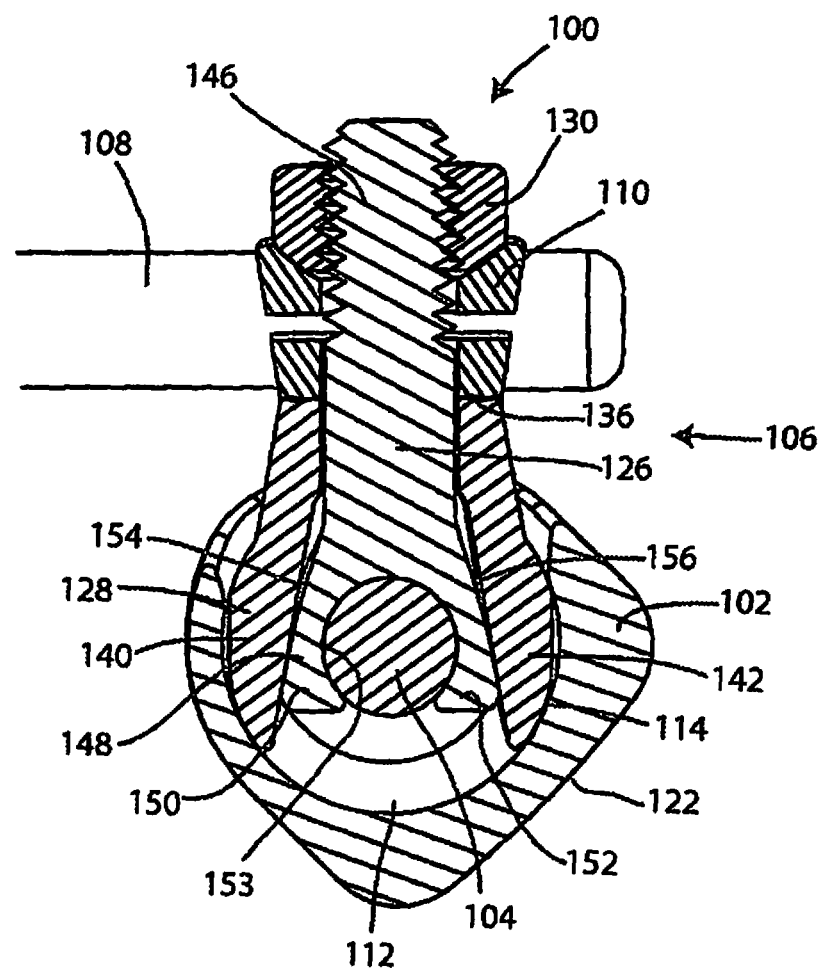
FIG. 4 is a partial cross-sectional view of an attachment mechanism of the facet joint implant of FIG. 2.

FIG. 4 displays the attachment mechanism in a cross-sectional view. The attachment mechanism 106 is configured to provide polyaxial adjustability between the inferior articular surface 122 and the inferior strut 104. Once the desired orientation of the articular surface 122 relative to the inferior strut 104 is reached, the attachment mechanism 106 may be locked down, securing the articular surface to the inferior strut. Referring to FIGS. 3 and 4, the attachment mechanism comprises a locking member which is a threaded conical expander 126, an expandable member which is an expandable split shell 128, the split clamp 110, and a nut 130. An alternative embodiment of an attachment mechanism may exclude the split clamp 110.

The split shell 128 has a circular neck portion 132 through which passes a bore 134. The bore opening is surrounded by a radial spline 136. Adjacent to the neck portion 132 is a spherical portion 138 which comprises two expandable lobes 140, 142. An interior surface 143 of the lobes 140 may be tapered. The present embodiment of the invention includes two lobes, however it is appreciated that more lobes may be included, or other expandable portions, in other embodiments. The split shell 128 fits over the conical expander 126 such that a threaded post 146 of the conical expander passes through the bore 134. An expansion portion 148 of the conical expander 126 is forked and has two opposing flanges 150, 152 which are shaped to fit around and grip the inferior strut 104. An inner wall 153 of the flanges is curved to fit around the inferior strut, and the outer walls 154, 156 are tapered.

The split ring clamp 110 comprises an inner ring 160, an outer ring 162 and a collar 164 which joins the inner and outer rings. The collar 164 is shaped to receive and grip the crosslink rod 108. The split ring clamp is configured such that when the inner and outer rings 160, 162 are compressed together, a diameter of the collar 164 decreases and the collar can tighten around and secure the crosslink rod. The surface of an exterior side of the inner ring 160 is a radial spline 166, which is shaped to engage with the radial spline 136 on the split shell 128.

When assembled, the split shell 128 fits over the conical expander 126, and the two parts fit within the inferior articular body 102 such that the interior cavity 112 houses the expansion portion 148 of the conical expander 126 nested inside the spherical portion 138 of the split shell 128. The conical expander 126, split shell 128 and inferior articular body 102 are oriented so that in general the flanges 150, 152 are adjacent to the lobes 140, 142, and the lobes are adjacent to the interior wall 114 of the interior cavity 112. A rod portion of the inferior strut 104 fits between the flanges 150, 152 of the conical expander.

The split ring clamp 110 fits over the threaded post 146 of the conical expander so that the radial spline 166 of the split clamp meets the radial spline 136 of the split shell 128. The crosslink rod 108 extends through the collar 164 of the split clamp. The nut 130 is threaded onto the threaded post 146 of the conical expander.

Until the attachment mechanism 106 is locked down by actuating the nut 130, the implant is adjustable in multiple ways. The crosslink rod 108 has relative angular freedom of motion about the clamp axis 111 and the inferior strut axis 105. The position of the crosslink rod 108 relative to the split clamp 110 may be adjusted such that a relatively longer or shorter portion of the crosslink rod 108 extends through the clamp. This provides an opportunity to select the best fit to the patient's anatomy and the specific vertebral level being treated. Similarly, the position of the inferior strut 104 may be adjusted relative to the inferior articular body 102 such that a relatively longer or shorter length of the inferior strut 104 extends through the flanges 150, 152 of the conical expander 126. Also, the inferior strut 104 has relative angular freedom of motion about the clamp axis 111. The inferior articular body 102 may be polyaxially rotated about the conical expander 126 and the split shell 128. The adjustments provide relative rotation between the inferior articulation surface 122 and the inferior strut 104 about three orthogonal axes. In addition, prior to lockdown, relative translation between the inferior strut 104, the inferior articulation surface 122, and the crosslink 108 is permitted.

The attachment mechanism 106 is locked down in a taper lock mechanism by actuating, or turning the nut 130. As the nut is turned and its threads engage the threaded post 146, the conical expander 126 is urged "upward" through the nut 130, while the outer ring 162 of the split clamp 110 is urged "downward" toward the inner ring 160. As the conical expander 126 moves, the flanges 150, 152 push against the lobes 140, 142 of the split shell 128, and in turn the lobes expand and push against the interior wall 114 of the interior cavity 112. Simultaneously, the flanges 150, 152 are compressed around the inferior strut 104. Similarly, the collar 164 of the split clamp 110 is compressed around the crosslink rod 108 as the inner 160 and outer 162 rings of the clamp are urged together. The nut 130 may be actuated until the resulting internal compression prevents any further motion, and the mechanism is locked down.

The inferior implant 100 may be delivered in an assembled, but not locked down, configuration. The crosslink rod 108 may be included in the assembly, provided separately, or excluded. The inferior implant 100 may be delivered in combination with a superior implant, in which a clip or other temporary fastener holds the inferior articular surface to a superior articular surface of the superior implant.

Figure 5:
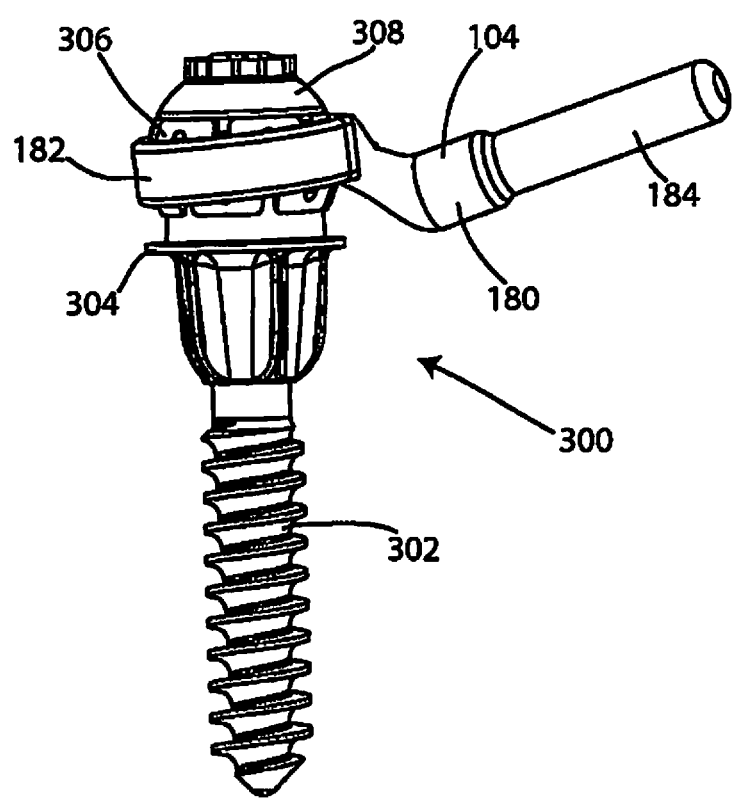
FIG. 5 is a perspective view of a fixation assembly secured to an inferior strut.

Referring to FIG. 5, inferior strut 104 is shown coupled to fixation assembly 300, which may also be termed an attachment mechanism. Fixation assembly 300 is configured to be implanted in a pedicle of a vertebra, and to be coupled to inferior implant 100 or another implant. The fixation assembly 300 is polyaxially adjustable, and comprises a fixation member 302, a base member 304, a split sphere 306, and a top nut 308. The inferior strut 104 is generally elongated in configuration, with a central portion 180, a first end or fixation portion which is a ring 182, and a second end which is a strut post 184. The ring 180 may be set at an angle relative to the central portion 180 and the strut post 184. Conversely, the strut post 184 may be at an angle relative to the central portion and the ring; also the central portion 180 may be straight, bent or curved.

Figure 6:
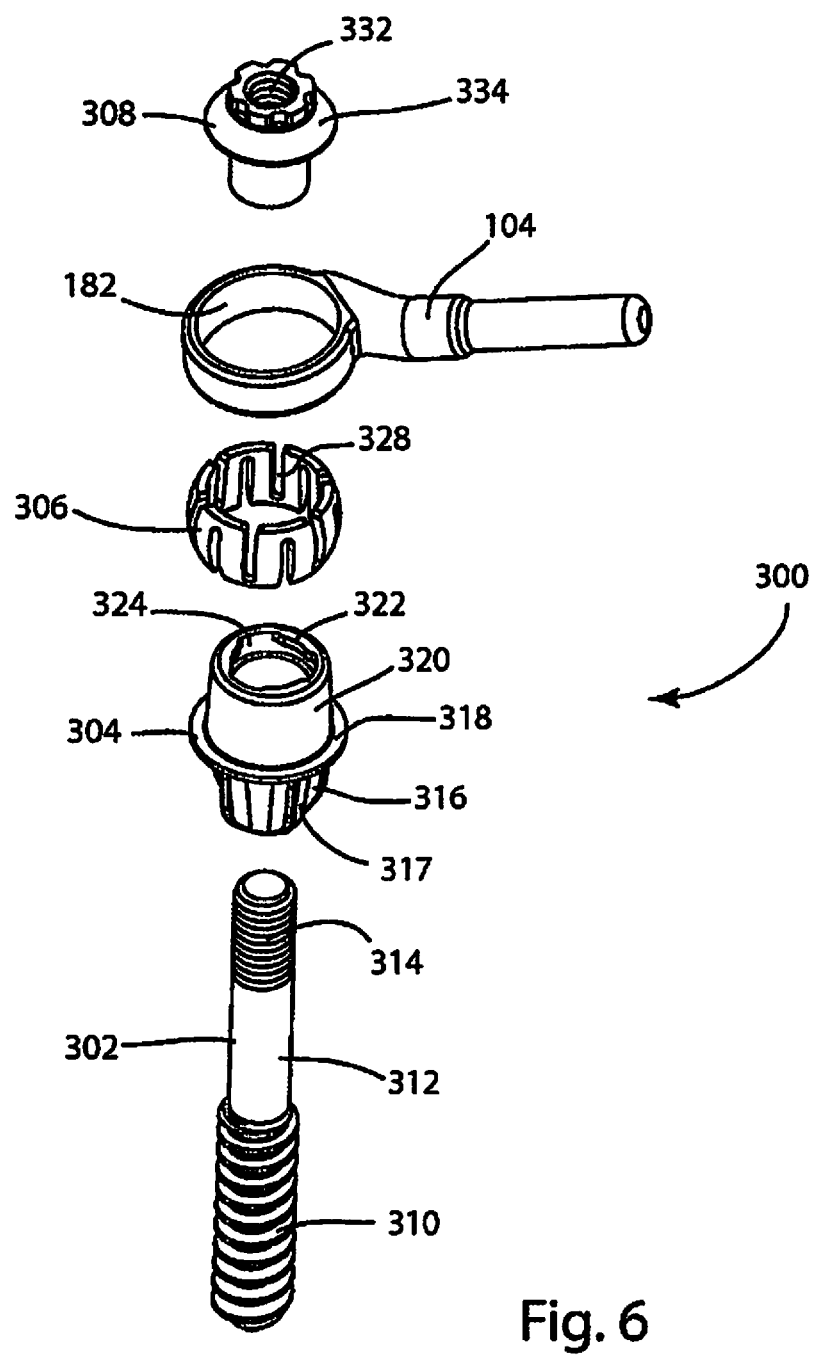
FIG. 6 is an exploded view of the fixation assembly and inferior strut of FIG. 5.

FIG. 6 is an exploded view of the inferior strut 104 and the fixation assembly 300. The fixation member 302, which may be a pedicle screw, has a distal threaded bone-engaging portion 310, a shaft 312, and a proximal threaded attachment portion 314. The base member 304 is cannulated throughout, and has a bone-engaging portion 316, a flange 318 and a tapered portion 320. The bone-engaging portion may be tapered to provide compression to the surrounding bone, and may have a plurality of fins 317 which prevent rotation of the base 304 in the bone. In alternate embodiments of the invention, the bone-engaging portion 316 may include teeth, studs, posts, fins, or combinations thereof, or other anti-rotation features, or no anti-rotation features. The tapered portion 320 may serve as an attachment portion, configured for attachment of an implant. At an open end of the tapered portion 320, a tool engagement rim 322 includes a plurality of notches 324. Other embodiments of the base may include threads or other features instead of notches configured to engage a tool. The split sphere 306 is sized to fit over the tapered portion 320 of the base 304, and includes a plurality of slits 328 which allow the sphere to be expandable. The split sphere 306 may also include a tapered inner wall. The top nut 308 has a threaded bore 332 and a flange 334 which encircles the nut 308.

The fixation assembly 300 may be delivered in a partially assembled state or be assembled from the components described above. During implantation, the fixation member 302 may be implanted in the pedicle of the vertebra using methods known in the art. The base member 304 is fit over the shaft of the fixation member 302. The split sphere 306 fits over the tapered portion 320 of the base 304. The fixation portion, or ring 182 of the inferior strut 104 is placed so it encircles the split sphere 306, attaching the inferior strut to the fixation member. Optionally, split sphere 306 may be provided already captured in the fixation portion of the strut. Before or after placement on the base 304, the ring 182 may be polyaxially adjusted around the split sphere so that the inferior strut 104 attains a desired orientation. To lock down the desired orientation, a compression lockout tool (not shown) engages the notches 324 of the tool engagement rim 322 on the base 304. Other embodiments of the base may include a threaded tool engagement interface, configured to engage with a threaded lockout tool. The lockout tool provides compression on the split sphere 306, urging it farther onto the tapered portion 320 toward the flange 318. As the split sphere 306 moves down the tapered portion 320, it expands and engages the ring 182 of the inferior strut 104. Once all motion between the tapered portion 320, split sphere 306 and ring 182 is locked out, the tool is removed. The top nut is threaded onto the threaded attachment portion 314 of the fixation member 302, to retain the base 304, sphere 306 and ring 182 on the fixation member, and to further secure the bone-engaging portion 316 in the vertebra. Optionally, the base 304, split sphere 306, and ring 182 may be assembled and locked out independently of the fixation member 302, then dropped onto the fixation member 302 and retained with the top nut 308. The inferior implant 100 may be secured to the inferior strut 104 before or after the inferior strut 104 is locked into position with the base 304 and split sphere 306.

Figure 7:
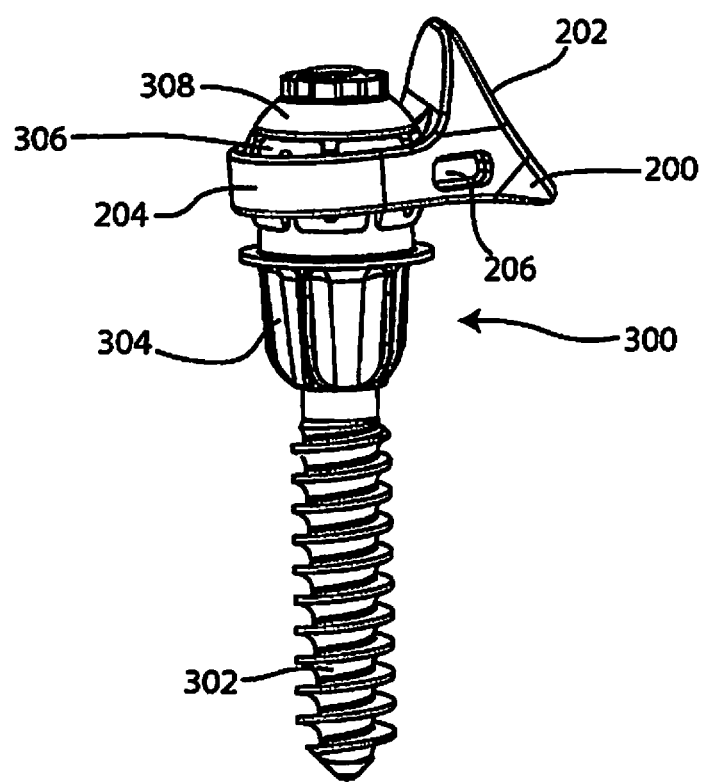
FIG. 7 is a perspective view of a fixation assembly secured to a superior facet joint implant.

Referring to FIG. 7, the superior implant 200 is shown secured to the fixation assembly 300. The superior implant 200 may be monolithic and includes a superior articulation surface 202 shaped to replace a natural superior articular surface of a vertebra, a fixation portion or ring 204, and may include at least one notch-like gripping feature 206. The superior implant 200 may be secured to the fixation assembly 300 in the same method as described previously for the inferior strut 104. The ring 204 of the superior implant 200 is locked in position relative to the split sphere 306 and the base member 304. The base 304, split sphere 306 and implant 200 may be dropped over an implanted fixation member 302, and the top nut 308 secured on the fixation member to retain the assembly. The superior implant 200 may be delivered in combination with an inferior implant 100, and the superior articular surface 202 may be temporarily clipped to the inferior articular surface 122.

Returning to FIG. 1, the components comprising the fixation assembly 300, superior 200, 201 and inferior 100, 101 implants and crosslink 108 may be implanted as follows. The pedicles are prepared for implantation, which may include removal of natural facet surfaces and bone preparation, and may include a broaching step to shape the pedicles to receive the base components. Broaching may ensure bone ingrowth and better mechanical retention of the bases and therefore the full implant system. Initially the fixation member 302 for each fixation assembly 300 is driven into the pedicles to a prescribed or desired depth. A base member 304 is placed on each fixation assembly 300, and the bone-engaging portion may be urged into the bone by pressing, tapping or other means. A split sphere 306 is placed on the bases in the caudal vertebra 2 intended for the superior implants, and the fixation portions of the superior implants 200, 201 are placed over the split spheres, and locked down relative to the fixation assembly as described previously. Alternatively, the split sphere 306 may be captured in the ring 204 of the implant 200 or 201, and the implant/ring assembly placed on the base 304.

Next, the inferior implants 100, 101 are each assembled with an inferior strut 104, but not yet locked to the strut. A split sphere 306 is captured in the fixation ring 182 of each strut 104, and each inferior implant/strut/sphere assembly is placed on the attachment portion of the base member 304 on a fixation member 302 on the cephalad vertebra 4. An offset distance between the inferior articular surface and the fixation assembly may be adjusted by moving the conical expander 126 relative to the inferior strut 104. At this point, the inferior articular surfaces are aligned with the superior articular surfaces, and may be temporarily clipped together to maintain the alignment. Additionally, the orientation of the inferior articular surface 122 may be polyaxially adjusted relative to the strut 104 by moving the split shell 128 relative to the cavity 112. The inferior implant/strut assemblies are locked down to the fixation assemblies.

The crosslink 108 may now be inserted through the collar 164 of the split clamp 110 of one inferior implant 100 or 101 and optionally through a prepared spinous process, and through the other collar 164 on the remaining inferior implant 100 or 101. It is appreciated that as the crosslink 108 is inserted, the split clamp 110 is rotatable about the clamp axis 111. Therefore, the crosslink 108 may be positioned to pass through a spinous process, or may pass through soft tissue caudal to the spinous process. Alternatively, the crosslink 108 may be inserted before the inferior implants are locked down to the fixation assemblies. The attachment assemblies 106 of each inferior implant 100, 101 are actuated to lock down the implants, fixing the positions of the articular surfaces 122, the inferior struts 104 and the crosslink 108 relative to their respective fixation assemblies. Post-operatively, the articular surfaces will be capable to articulate against one another, allowing a level of natural spinal motion.

Some variation in the steps described above may occur. For example, the inferior articular body 102 may be available packaged with the superior implant 200, temporarily clipped together such that the articular surfaces 122, 202 are in a desired alignment. In this instance, the inferior articular body 102 is inserted with the superior implant 200 as the superior implant 200 is placed and locked with the fixation assembly 300. Then the inferior strut 104 and the remaining components of the inferior implant 100, including the conical expander, split shell, and split clamp are assembled with the inferior articular body 102. The fixation portion, or ring 182 of the inferior strut 104 is assembled and locked down with the inferior fixation assembly 300. The insertion of the crosslink 108 and final lockdown is as described previously, and the clip is removed.

Alternatively, the inferior implant 100 may be available secured to a clip. The implant 100, with the attached clip, may be inserted adjacent to an already implanted and locked down superior implant, and the inferior and superior implants temporarily clipped together. The inferior strut is adjusted and locked down to its fixation assembly. The insertion of the crosslink 108 and final lockdown of the inferior implant is as described previously, and the clip is removed.

System 10, and other facet replacement components disclosed herein, may also be implanted on multiple vertebral levels to provide facet joint replacement across several levels. In a multi-level application, additional superior implants could be added to the fixation assemblies 300 which secure the inferior struts 104, to extend the system in a cephalad direction. Similarly, to extend the system caudally, additional inferior struts coupled to inferior implants could be added to the fixation assemblies 300 which secure the original superior implants 200. Also, fusion rods (not shown) may be secured between fixation assemblies 300 on adjacent vertebra to provide rigid fusion at a desired vertebral level.

Figure 8:
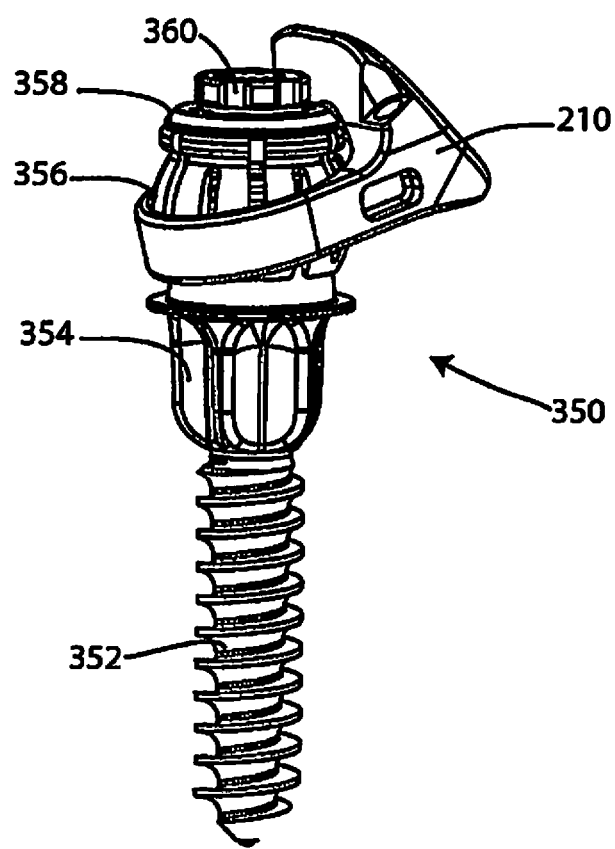
FIG. 8 is a perspective view of an alternate fixation assembly secured to a superior facet joint implant.
Figure 9:
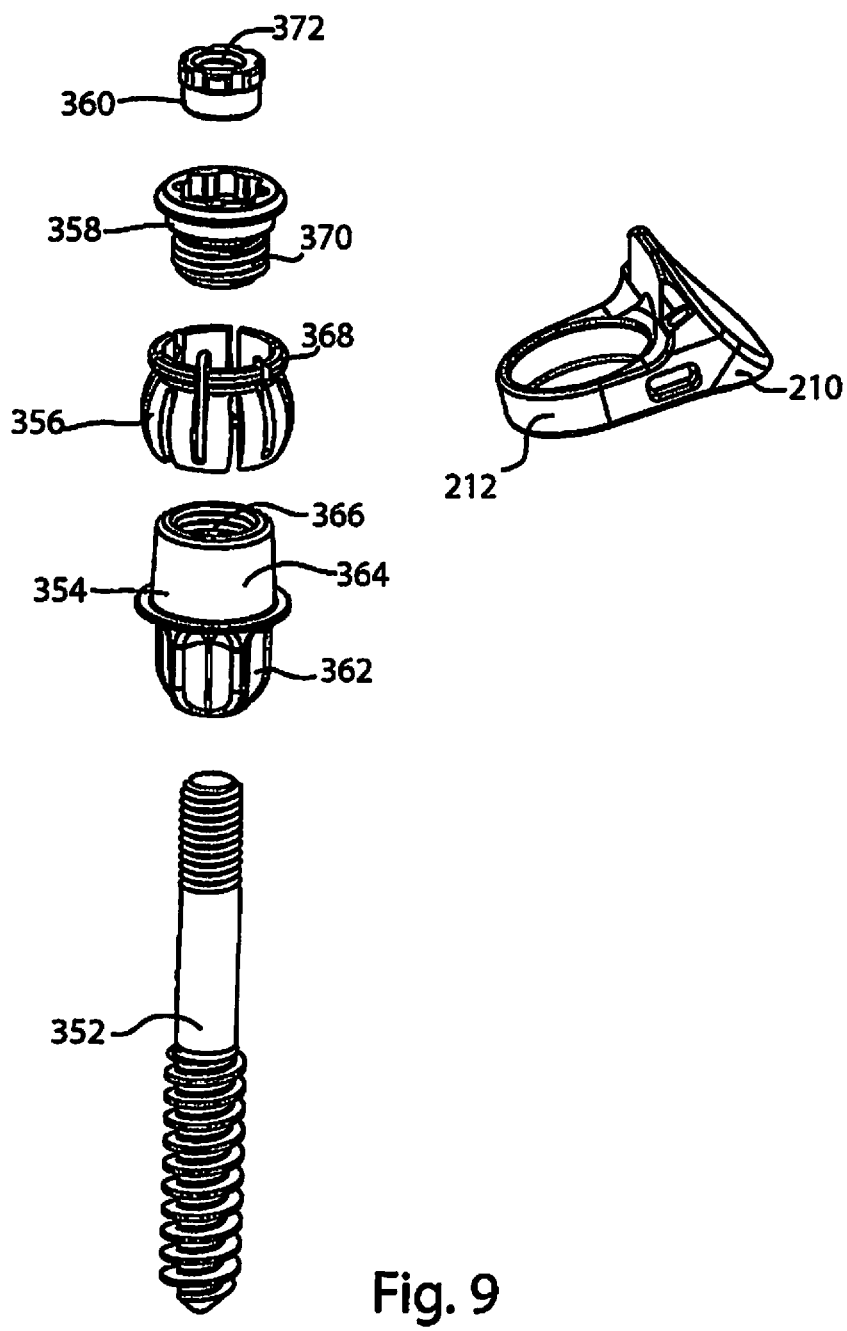
FIG. 9 is an exploded view of the alternate fixation assembly and superior facet joint implant of FIG. 8.
Figure 10:
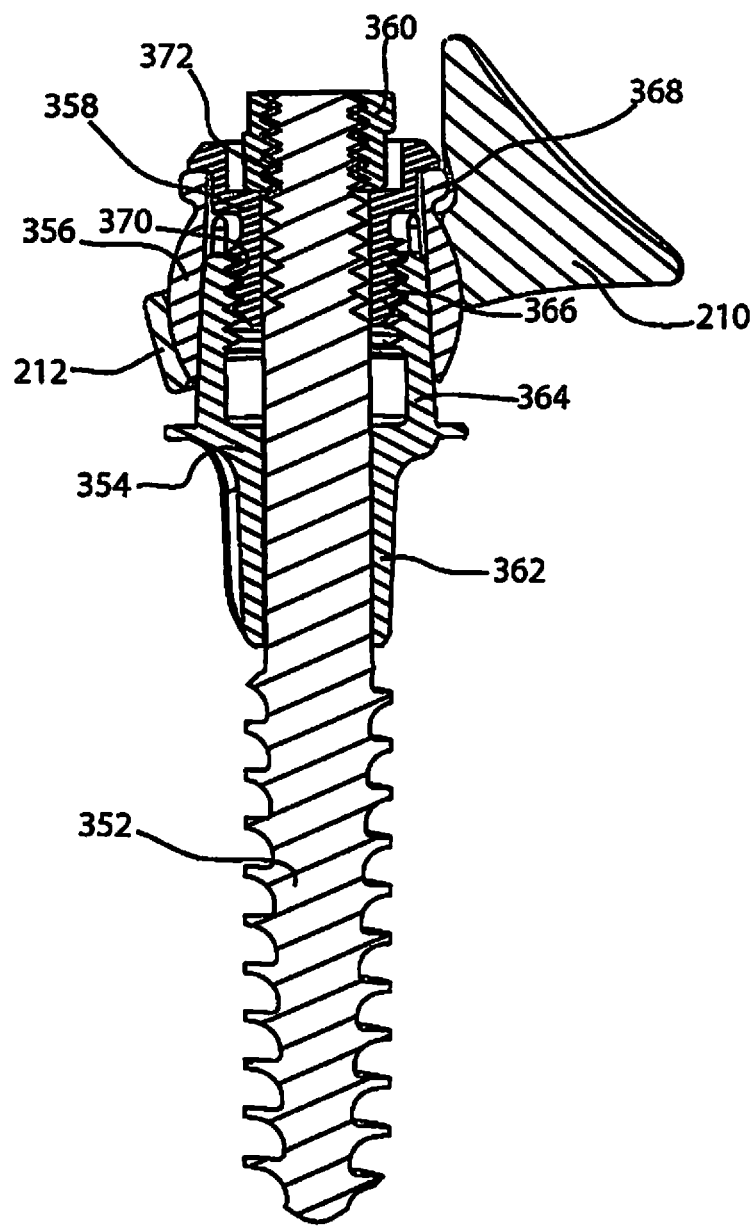
FIG. 10 is a partial cross-sectional view of the alternate fixation assembly and superior facet joint implant of FIG. 8.

FIG. 8 presents an alternative embodiment of a polyaxially adjustable fixation assembly 350 with an alternative embodiment of a superior implant 210. FIG. 9 presents an exploded view of fixation assembly 350, and FIG. 10 presents a cross-sectional post-assembly view of the assembly. With reference to all three figures, fixation assembly 350 comprises a fixation member 352, a base member 354, a flanged split sphere 356, a capture nut 358, and a top nut 360. The cannulated base member 354 has a bone-engaging portion 362 which may include anti-rotation features such as fins, teeth or studs. A tapered portion 364 has a threaded lumen 366. The split sphere 356 includes a split flange 368 which encircles one open end of the sphere. The capture nut 358 has a threaded outer surface 370, while the top nut 360 has a threaded inner surface 372. Fixation assembly 350 may also be termed an attachment mechanism. It is appreciated that fixation assembly 350 may be substituted for fixation assembly 300 in any fixation procedure disclosed or depicted herein, and vice versa. Also, a combination of fixation assemblies 300 and 350 may be used in an implant system.

The fixation member 352 is initially implanted into the pedicle, and the base member 354 is inserted over the fixation member 352 and seated in the bone. The split sphere is placed over the tapered portion 364 of the base member 354. A fixation portion, or ring 212 of the superior implant 210 is placed around the split sphere 356. At this point, the ring 212 may be polyaxially adjusted to attain a desired orientation of the superior implant 210. To lock the orientation and position of the superior implant 200, a lockout tool (not shown) is actuated to effect the taper lock. The lockout tool has an externally threaded inner shaft tip which is engaged in the threaded lumen 366 of the base member 354. The lockout tool is actuated, using tensile force to simultaneously pull on the base member 354 with the inner shaft, and push on the flange 368 of the split sphere 356 with an outer shaft. This force moves the split sphere 356 farther onto the tapered portion 364. The split sphere 356 expands and engages the ring 212 of the superior implant 210 until all motion ceases and the position of the ring 212 is locked down. The lockout tool is unthreaded and removed, and the capture nut 358 is threaded into the tapered lumen 366, also capturing the flange 368 of the split sphere 356. The capture nut 358 is included to ensure the long-term integrity of the lock. The top nut 360 is threaded onto the fixation member 352, and assists in holding the tapered base 362 against the bone surface. The top nut 360 and capture nut 358 may use the same driver.

Figure 11:
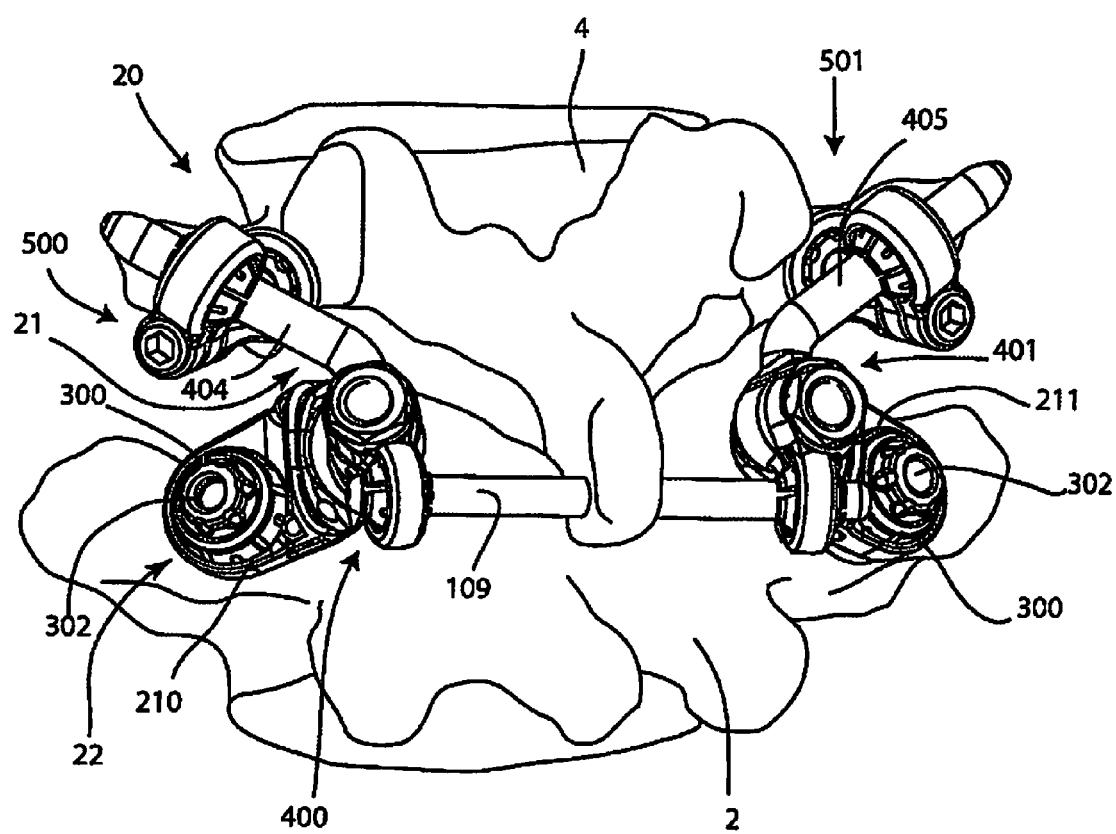
FIG. 11 is a perspective view of a portion of a spine with an alternate bi-lateral facet joint replacement system implanted into two adjacent vertebrae.

Referring to FIG. 11, a perspective posterior view depicts an alternative embodiment of a bi-lateral facet joint replacement system 20, implanted in two vertebrae. On the left lateral side, superior facet joint prosthesis 22 comprises a superior implant 210 and a fixation assembly 300, secured to the first vertebra 2. The superior articular surface articulates with an inferior articular surface of an inferior facet joint prosthesis 21, which comprises implant 400 and fixation assembly 500. An polyaxially adjustable attachment mechanism couples an inferior implant body to one end of an inferior strut 404, and a crosslink rod 109 which crosses a sagittal plane of the vertebrae. An opposite end of the inferior strut is secured to the second vertebra 4 by the fixation assembly 500. On the right lateral side, a mirror-image of the system is implanted, including superior implant 211, second fixation assembly 300, inferior implant 401, inferior strut 405 and fixation assembly 501. The crosslink rod 109 links the left inferior implant 400 to the right inferior implant 401. As previously set forth, only one lateral side of the system will be depicted and described.

Figure 12:
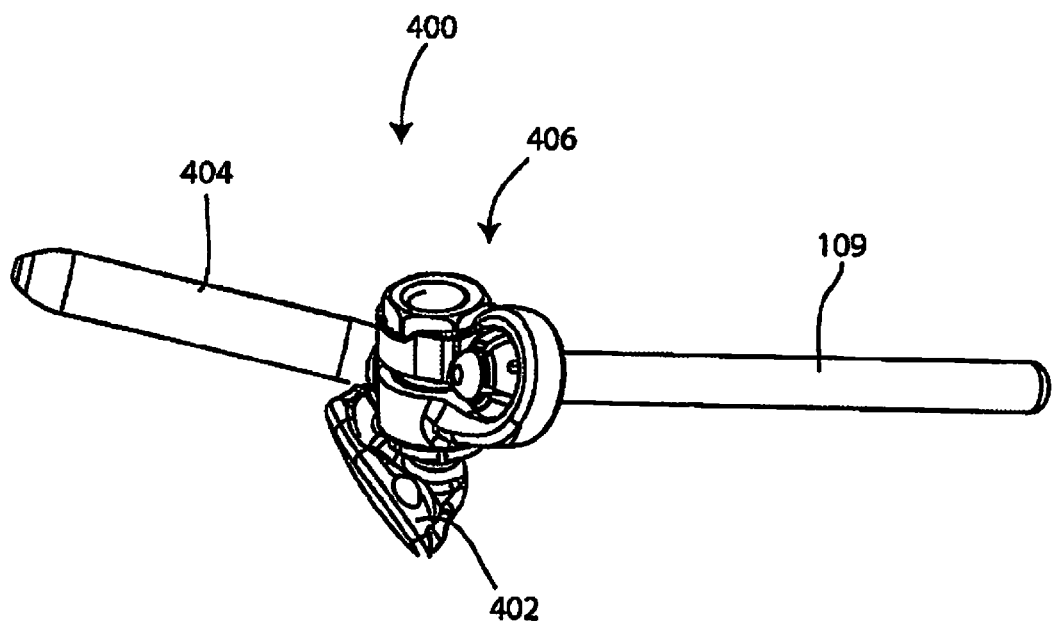
FIG. 12 is a perspective view of an inferior facet joint implant coupled to a crosslink rod.

FIG. 12 depicts the inferior implant 400, which comprises an inferior articular body 402, an inferior strut 404, and an attachment mechanism 406 which polyaxially adjustably secures the articular body to the inferior strut. The crosslink rod 109 may be also secured to the inferior implant 400 by the attachment mechanism 406. Attachment mechanism 406 may have two configurations: an adjustable configuration in which there is relative rotation between the inferior articular body 402, the inferior strut 404 and the crosslink rod 109, and a locked configuration in which the inferior articular body 402, the inferior strut 404 and the crosslink rod 109 are rigidly secured to each other.

Figure 13:
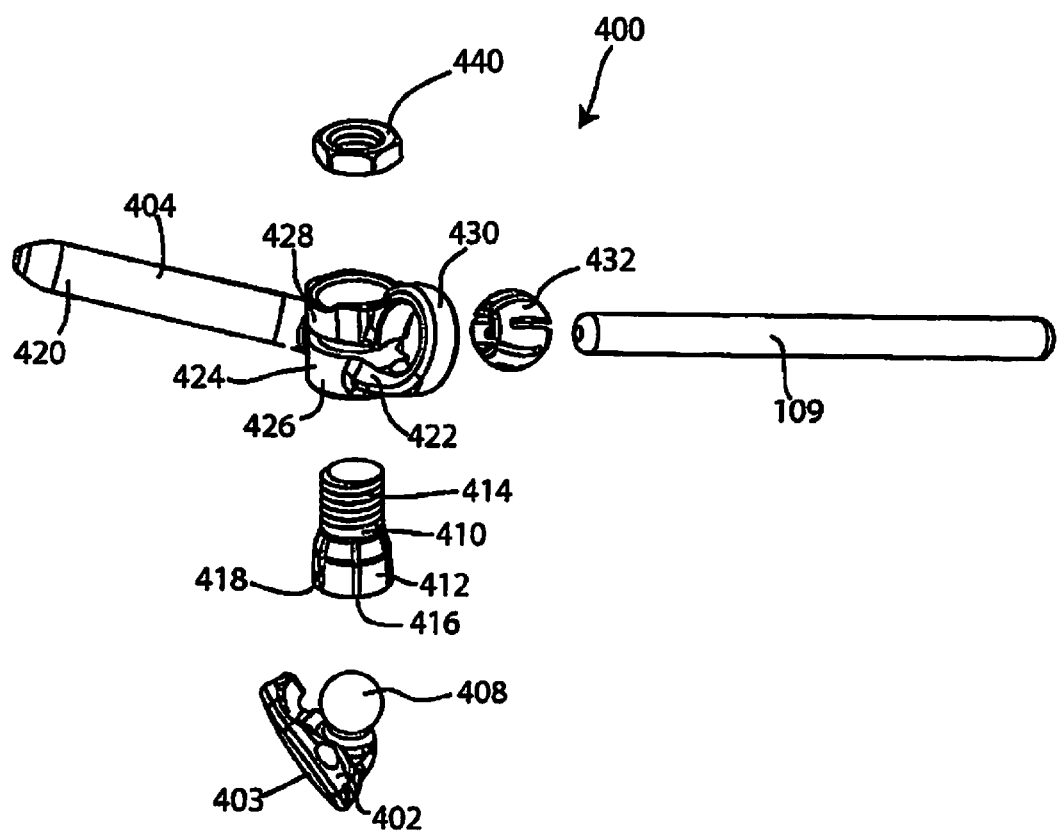
FIG. 13 is an exploded view of the inferior facet joint implant and crosslink rod of FIG. 12.

FIG. 13 is an exploded view of the inferior articular body 402, inferior strut 404, crosslink rod 109 and the attachment mechanism 406. The inferior articular body 402 is monolithic and comprises an inferior articulation surface 403 shaped to replace a natural inferior articular surface of a vertebra, and a connection feature which has a rounded surface 408, which in this embodiment is a spherical surface. A compressible member 410 includes a conical portion 412 and a threaded post 414. The conical portion 412 has an interior cavity 416 encircled by a plurality of expandable fingers 418. The interior cavity 416 is shaped to receive the rounded surface 408.

The inferior strut 404 has a first end 420 which is shaped as a rod and serves as the fixation portion for the strut. Other embodiments of the inferior strut may have a first end shaped as a ring or another shape. A second end 422 is shaped as a ring, and comprises a split ring clamp 424, the split ring clamp having an inner ring 426, an outer ring 428, and a collar 430, which connects the inner and outer rings. The collar 430 is oriented generally orthogonal to the inner and outer rings. The collar 430 is shaped to receive a split sphere 432, which has an interior shaped to receive the crosslink rod 109. A nut 440 is configured to be threaded on the threaded post 414. Inferior strut 404 may be straight, or it may be curved or bent such that the first and second ends 420, 422 are oriented at an angle relative to one another, as seen in FIG. 11.

Figure 14:
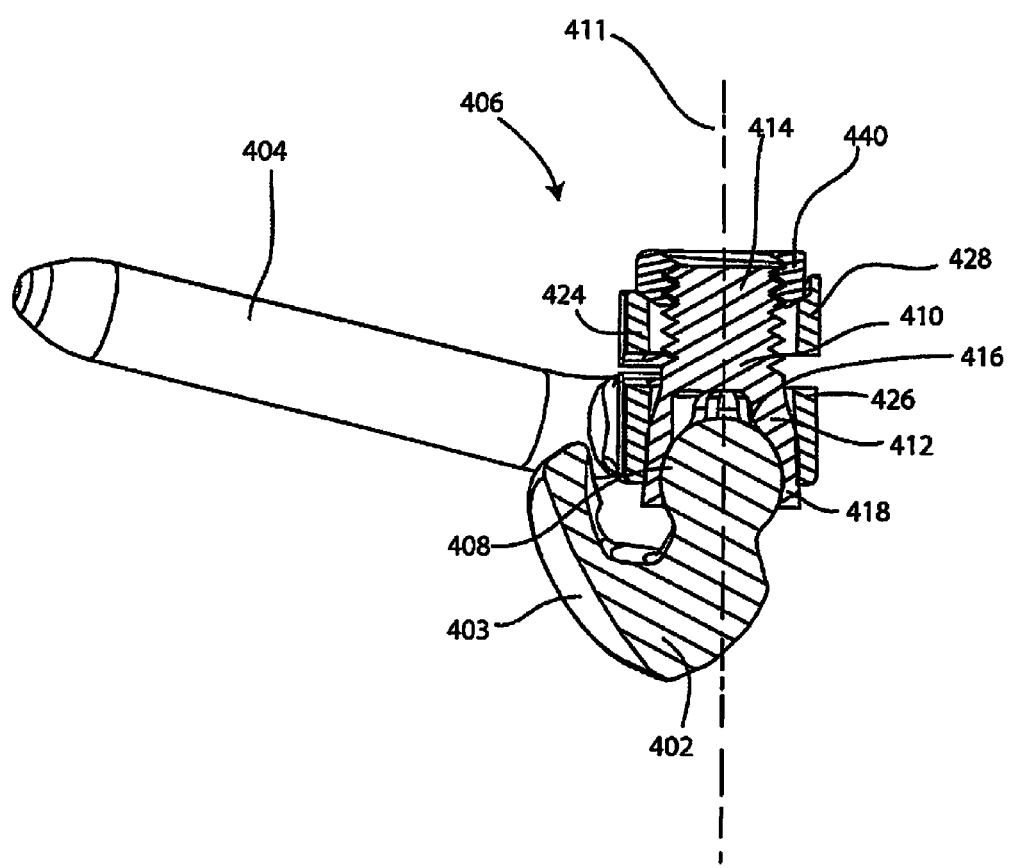
FIG. 14 is a partial cross-sectional view of the inferior facet joint implant of FIG. 12.

FIG. 14 is a partial cross-sectional view of the attachment mechanism 406 components in the locked configuration (the collar 430, split sphere 432 and crosslink 109 are not visible in this figure). A clamp axis 411 extends longitudinally through the attachment mechanism. As described previously, the rounded surface 408 is received in the cavity 416 of the compressible member 410. The split ring clamp 424 fits around the compressible member 410, with the inner ring 426 around the conical portion 412 and the outer ring 428 around the threaded post 414. The collar 430 fits around the split sphere 432, which receives the crosslink rod 109. Also with reference to FIG. 13, when thus assembled but not locked down, the attachment mechanism 406 is adjustable in multiple ways. The inferior articular surface 403 may be polyaxially rotated relative to the inferior strut 404 and the crosslink rod 409 by rotation of the rounded surface 408.

The split sphere encompassing the crosslink rod 109 may be polyaxially rotated within the split ring clamp 424 relative to the inferior strut 404 and the inferior articular surface 403. A length of the crosslink rod 109 which extends through the attachment mechanism 406 may be adjusted. The inferior strut 404 has relative angular freedom of motion about the clamp axis 411. These adjustments provide relative rotation between the inferior articulation surface 403 and the inferior strut 404 about three orthogonal axes. In addition, prior to lockdown, relative translation between the inferior strut 404, the inferior articulation surface 403, and the crosslink 109 is permitted. An attachment mechanism 407, for the right side of the vertebrae, is configured as a mirror image of attachment mechanism 406.

The attachment mechanism 406 is locked down by actuating, or turning the nut 440. Lockdown of the attachment mechanism locks out both the position of the inferior strut relative to the inferior articulation surface, and the position of the crosslink. As the nut is turned and its threads engage the threaded post 414, the compressible member 410 is urged "upward" through the nut 440, while the outer ring 428 of the split ring clamp 424 is urged "downward" toward the inner ring 426. As the compressible member 410 moves, the tapered outer wall of the conical portion 412 engages the inner surface of the inner ring 426. Simultaneously, the interior wall of the conical portion 412 exerts compressive force against the rounded surface 408 in the interior cavity 416. Similarly, the collar 430 of the split ring clamp 424 is compressed around the split sphere 432, which compresses around the crosslink rod 109, as the inner 426 and outer 428 rings of the clamp are urged together. The nut 440 may be actuated until the resulting internal compression prevents any further motion, and the mechanism is locked down.

Figure 15:
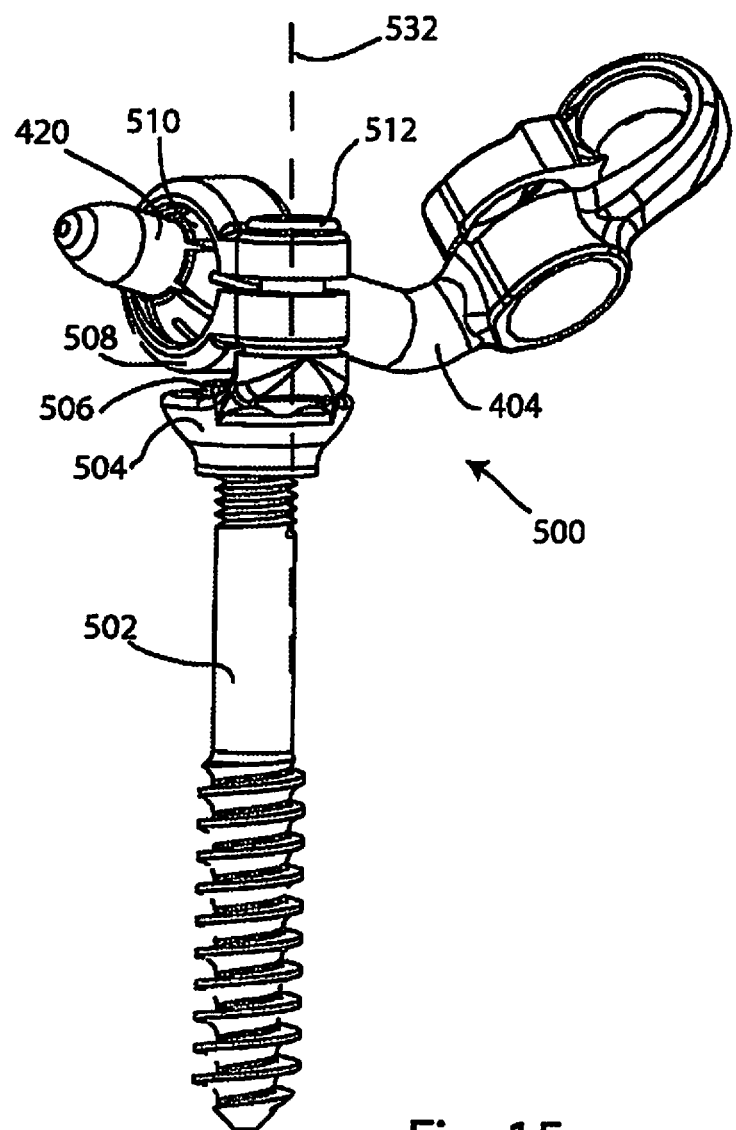
FIG. 15 is a perspective view of a fixation assembly and an inferior strut.

FIG. 15 is a perspective view of the fixation assembly 500, coupled to inferior strut 404. Fixation assembly 500 comprises a fixation member 502, a base member 504, a top nut 506, a split ring clamp 508, a split sphere 510 and a set screw 512. Fixation assembly 500 may also be termed an attachment mechanism, and it is adjustable, permitting polyaxial rotation of the inferior strut relative to the fixation member 502.

Figure 16:
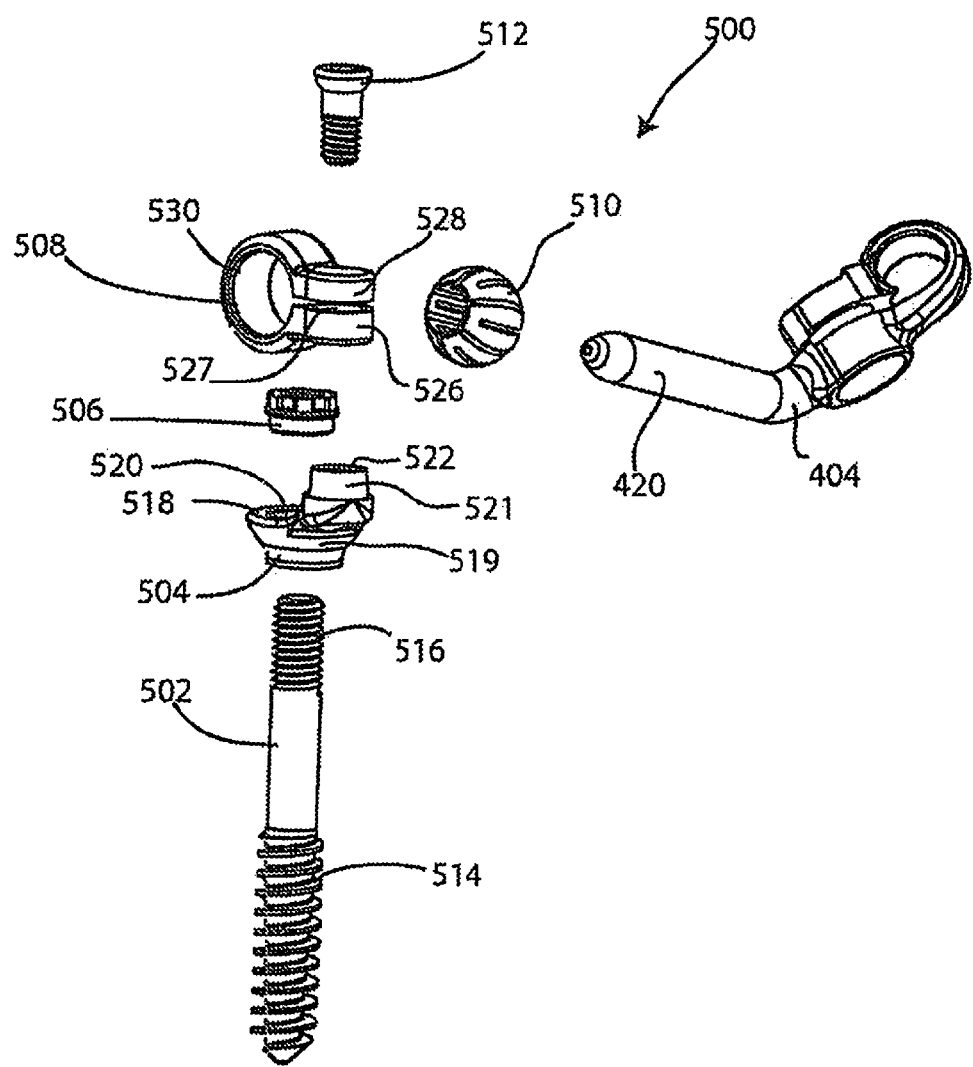
FIG. 16 is an exploded view of the fixation assembly and inferior strut of FIG. 15.

FIG. 16 is an exploded perspective view of the fixation assembly 500 and the inferior strut 404. The fixation member 502 comprises a threaded bone-engaging portion 514 and a threaded attachment portion 516. The base member 504 comprises a receptacle 518 with a fixation bore 520 sized to receive the fixation member 502, and a bone-facing side 519. On the bone-facing side 519 may be fins, pegs, teeth or other anti-rotation features. The base member 504 may be dish-shaped as in FIG. 16, or may be spherical, tapered, or another shape. Coupled to the receptacle 518 is a tapered pedestal 521 which encircles a threaded attachment bore 522 sized to receive the set screw 512. The top nut 506 is sized to fit into the receptacle 518, and to be threaded onto the attachment portion 516 of the fixation member. The split ring clamp 508 comprises an inner ring 526, an outer ring 528, and a collar 530 which connects the inner and outer rings. An inner wall 527 of the inner ring 526 may be tapered. The set screw 512 is threaded and sized to be received in the attachment bore 522. The split sphere 510 is sized to fit around the rod-like fixation portion or first end 420 of the inferior strut 404, and sized to fit inside the collar 530 of the split ring clamp 508. A mirror-image fixation assembly 501 is configured to be implanted on the right side of the vertebra.

Returning to FIG. 15, fixation assembly 500 may be assembled and locked down as follows. Fixation member 502 is driven into a prepared pedicle at a desired depth. Base member 504 is placed on the fixation member 502 so that the threaded attachment portion 516 fits through the fixation bore 520. The outer surface of the base member 504 may rest on the prepared pedicle. The top nut is threaded onto the attachment portion 516 and actuated to secure the base 504 to the pedicle. The split sphere 510 is captured in the collar 530 of the split ring clamp 508, and the fixation portion or rod portion 420 of the inferior strut may be slid into the split sphere. The split ring clamp 508, now connected to the inferior strut 404, is placed on the pedestal 521 so that the inner ring 526 surrounds the tapered pedestal 521. The set screw 512 is fit through the outer and inner rings 526, 528 and threaded into the attachment bore 522. At this juncture the angle of the inferior strut 404 relative to a clamp axis 532, which may be parallel to the fixation member 502, may be adjusted. Also, the split sphere 510 may be polyaxially rotated within the collar 530, permitting polyaxial adjustment of the inferior strut 404. When the preferred orientation of the inferior strut 404 relative to the clamp axis 532, and the preferred orientation of the inferior strut to the collar 530 are reached, the fixation assembly 500 is locked down by actuating the set screw 512. As set screw 512 is tightened, outer ring 528 is urged toward inner ring 526. As the rings 526, 528 come together, collar 530 is compressed around split sphere 510, which in turn compresses around rod portion 420, locking its position. As set screw 512 is turned, the tapered inner wall 527 of inner ring 526 is rigidly secured against the tapered pedestal 521, fixing the position of the split clamp ring 508 relative to the clamp axis 532.

With reference to FIGS. 11-16, the components comprising the fixation assemblies 300, 500, 501, superior 210, 211 and inferior 400, 401 implants and crosslink 109 may be implanted as follows. The pedicles are prepared for implantation, which may include resection of natural facet surfaces and bone preparation, and may include a broaching step to shape the pedicles to receive the base components. Broaching may ensure bone ingrowth and better mechanical retention of the bases and therefore the full implant system. The fixation member 302 for each fixation assembly 300 is driven into the pedicles of the caudal vertebra 2 to a prescribed or desired depth. A tapered base 304 is placed on each fixation member 302. A split sphere 306 and superior implant 210, 211 is placed on the tapered bases 304 intended for the superior implants, and the taper lock is locked down relative to the fixation assembly as described previously with reference to FIGS. 8-10.

Before or after the fixation assemblies 300 are prepared, the fixation members 502 for the fixation assemblies 500, 501 are driven to a desired depth in the cephalad vertebra 4. On the left side, base member 504 is placed over the fixation member 502 and secured by the top nut 506. The inferior strut 404 is assembled with the inferior articular body 402, and the attachment mechanism 406 as set forth previously, but not locked down. The split ring clamp 508 is assembled with the split sphere 510, and together they are slid onto the fixation portion of inferior strut 404. The split ring clamp 508, now attached to the inferior strut 404 and the inferior implant 400, is placed on the tapered pedestal 521 of the base member 504. On the right side, mirror-image duplicates of the left components are similarly assembled. The inferior implants 400, 401 are positioned so that the inferior articular surfaces are aligned with the superior articular surfaces of the superior implants 210, 211, and the inferior and superior articular bodies on each side may be temporarily clipped together to maintain the alignment. The inferior implant/ strut assemblies are locked down to the fixation assemblies by actuating the set screws 512.

The crosslink 109 may now be inserted through the collar 530 of the split clamp 508 of one inferior implant 400 or 401 and through a prepared spinous process, and through the other collar 530 on the remaining inferior implant 400 or 401. Alternatively, the crosslink 109 may be inserted before the inferior implants are locked down to the fixation assemblies. The attachment mechanisms 406 of each inferior implant 400, 401 are actuated to lock down the implants, fixing the positions of the articular surfaces 403, the inferior struts 404 and the crosslink 109.

Figure 17:
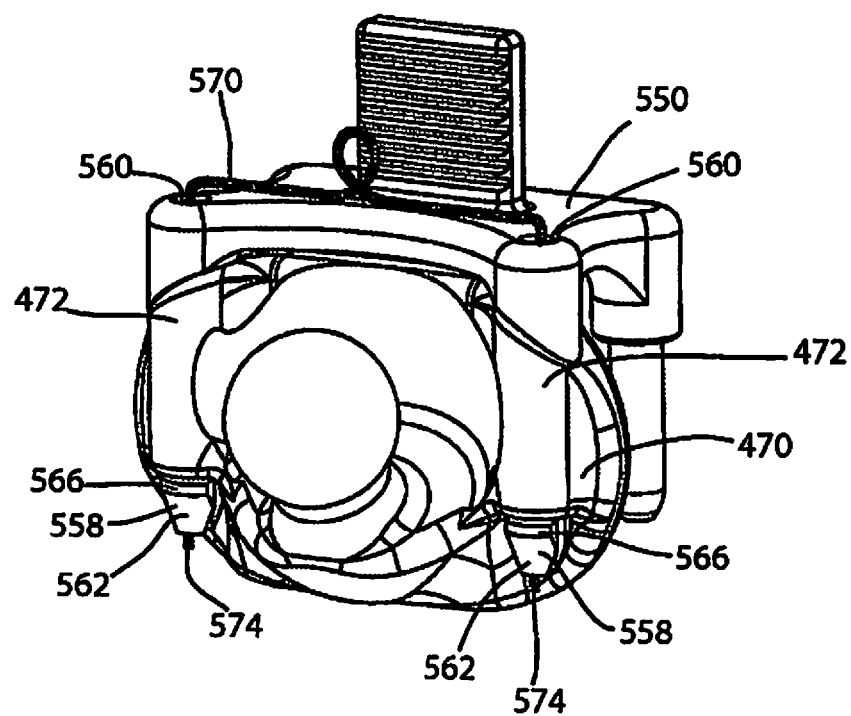
FIG. 17 is a perspective view of an inferior implant body coupled to a clip.

Some variation in the steps described above may occur. For example, as seen in FIG. 17, an inferior articular body 470 may be available pre-packaged temporarily locked to a coupler, or clip 550 with a plug 570, which will be described in further detail below. Alternatively, a gripping tool (not shown) may be used to hold the inferior articular body 470. The attachment mechanism 406 and the inferior strut 404 (not seen) are assembled to the inferior articular body 470. The superior implant 210 is placed on and taper locked with the fixation assembly 300, which is implanted in the pedicle. Using the clip 550 or gripping tool as a handle, the inferior implant articular body 470 with attached strut is placed adjacent to implanted superior implant 210 such that posts on the clip 550 engage in openings on the superior implant, and the inferior and superior articulation surfaces are aligned. Then the fixation portion of inferior strut 404 is slid into the split sphere 510 and the split ring clamp 508 of the fixation assembly 500. (Alternatively, the split sphere and split ring clamp 530 may be assembled to the inferior strut 404 before it is placed adjacent to the superior implant). Polyaxiality of the split sphere 510 relative to the collar 530 may be adjusted, and the set screw 512 is inserted and the fixation assembly 500 is locked down. The insertion of the crosslink 109 and final adjustment and lockdown of attachment mechanism 406 is as described previously. The clip 550 is unlocked and removed, allowing articulation between the inferior and superior implants along their respective articular surfaces.

Figure 18A:
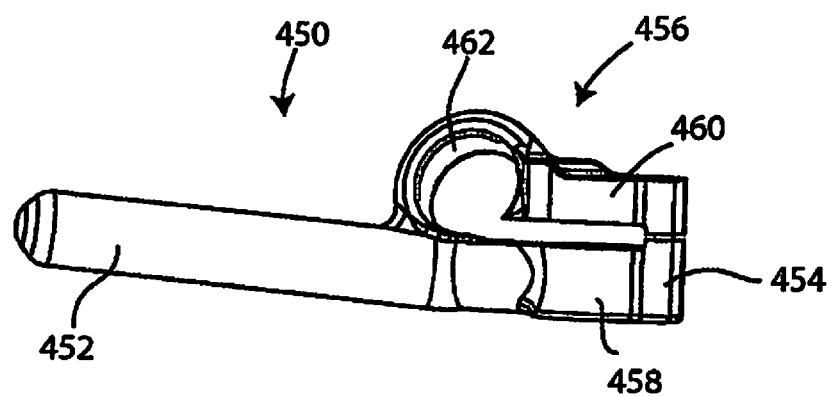
FIG. 18A is a perspective view of an alternate inferior strut.
Figure 18:
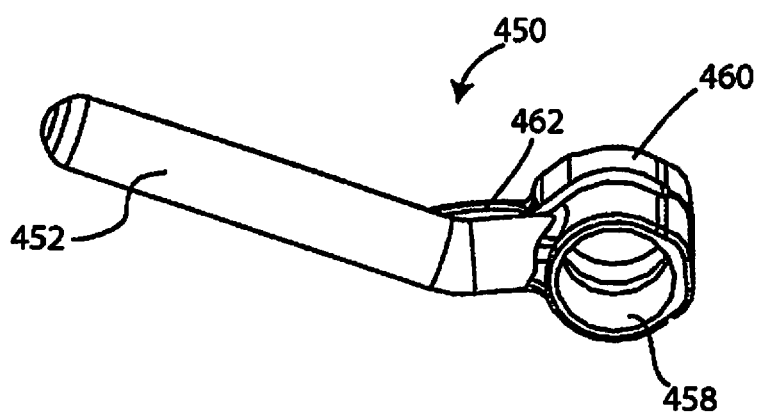
FIG. 18B is a perspective view from an alternate angle of the strut of FIG. 18A.

FIGS. 18A and 18B depict different perspective views of an alternate inferior strut 450. Inferior strut comprises a first end 452 and a second end 454. Fixation portion or first end 452 is post-like, and may be configured to be secured by a fixation assembly such as fixation assembly 500 seen in FIG. 15. Of course, other embodiments of the strut may include a first end which is a ring or a different shape. The second end 454 comprises a split ring clamp 456, which includes an inner ring 458 and an outer ring 460, which are joined by a collar portion 462. As seen in FIGS. 18A and 18B, the collar portion may be substantially orthogonal relative to the rings 458, 460, or it may be at another angle. Additionally, the angle of the second end 454 relative to the first end 452 may vary. Inferior strut 450 may be secured to an articular body by an attachment mechanism in the same manner as described for inferior strut 404; that is, a single actuating member may be actuated to urge the inner and outer rings 458, 460 together and compress the collar 462. Inferior strut 450 may differ from inferior strut 404 in features such as the position and/or angle of the split rings relative to the collar, and the angle of the second end comprising the split ring clamp relative to axis of the first post-like end, among others. It is appreciated that any inferior strut disclosed herein may be available in a variety of lengths, sizes, angles, and split ring clamp configurations.

Another alternative inferior strut (not pictured) may include separate polyaxially adjustable attachment mechanisms for a crosslink and an inferior articular body. Such an alternative strut may include a first ring positioned and shaped to receive a polyaxially adjustable crosslink rod, while a second ring is positioned and shaped to receive a polyaxially adjustable connection to an inferior articular body. Each ring may have an independent lockout mechanism such as a nut or screw.

Figure 19:
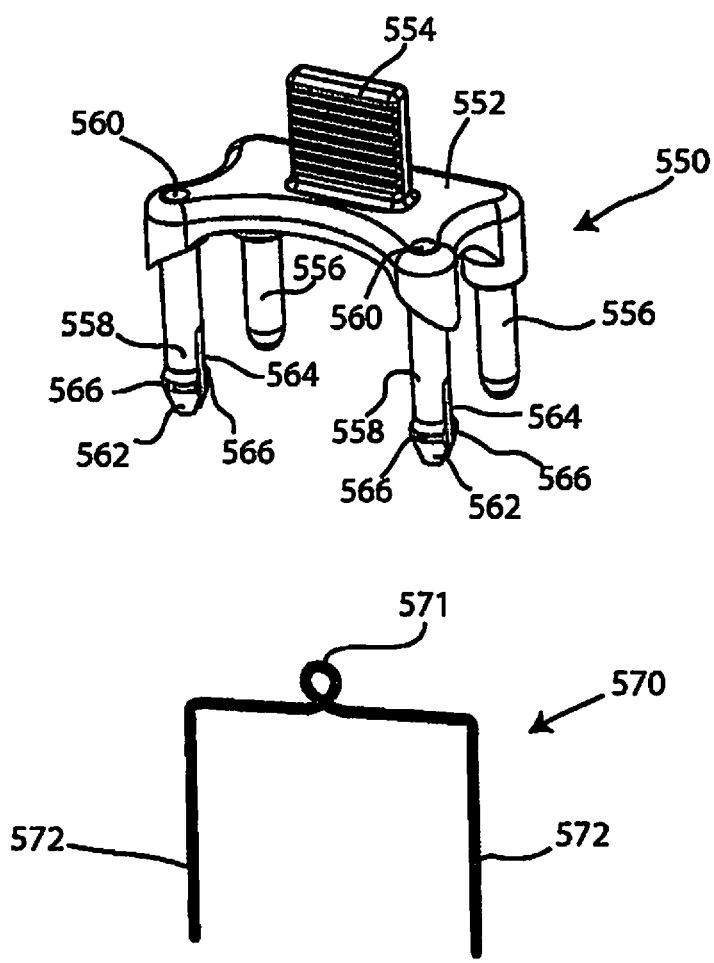
FIG. 19 is a perspective view of the clip of FIG. 17 and a plug.

FIG. 19 is a perspective view of the clip 550 and the plug 570. Clip 550 may be monolithic and comprises a clip body 552, a handle 554, and two pairs of posts which extend substantially orthogonally from the body: a pair of superior posts 556 and a pair of inferior posts 558. The inferior posts 558 are cannulated, each having a bore 560 which extends the length of the post, through a rigid portion 563 to a deformable flexible split end 562. Each split end 562 includes at least one slot 564 which extends partially along the length of the post 558, and a protruding flange 566. The inferior posts 558 are shaped to receive an inferior facet joint implant, and the superior posts 556 are shaped to receive a superior facet joint implant.

The plug 570 comprises a handle 571 and two wires 572 which are sized to extend through the bores 560 of the inferior posts 558 of the clip 550. When the plug 570 is inserted fully into the inferior posts 558, the wires 572 urge apart the flexible split ends 562 from a narrow first configuration to an expanded second configuration in which the slots 564 are widened, and the flanges 566 on each post are farther apart. When the plug 570 is removed, the split ends 562 deform, moving toward one another from the expanded second configuration to the narrow first configuration.

Returning to FIG. 17, the inferior articular body 470 is shown coupled with the clip 550 and the plug 570. The inferior posts 558 extend through tubes 472 formed on the inferior implant 470, such that the split ends 562 and flanges 566 emerge outside of the tubes. The plug 570 is fully inserted through the clip bores 560, and therefore the wires 574 keep the split ends in the expanded second configuration. In the expanded second configuration, the widened flanges 566 cause the diameter of the split ends 562 to be greater than the diameter of the tubes 472, retaining the articular body 470 and preventing the clip 570 from being withdrawn from the inferior articular body 470. Thus locked to the clip 550, the inferior articular body 470, with or without other attached components such as a compressible member and/or an inferior strut, may be clipped to a superior implant.

Figure 20:
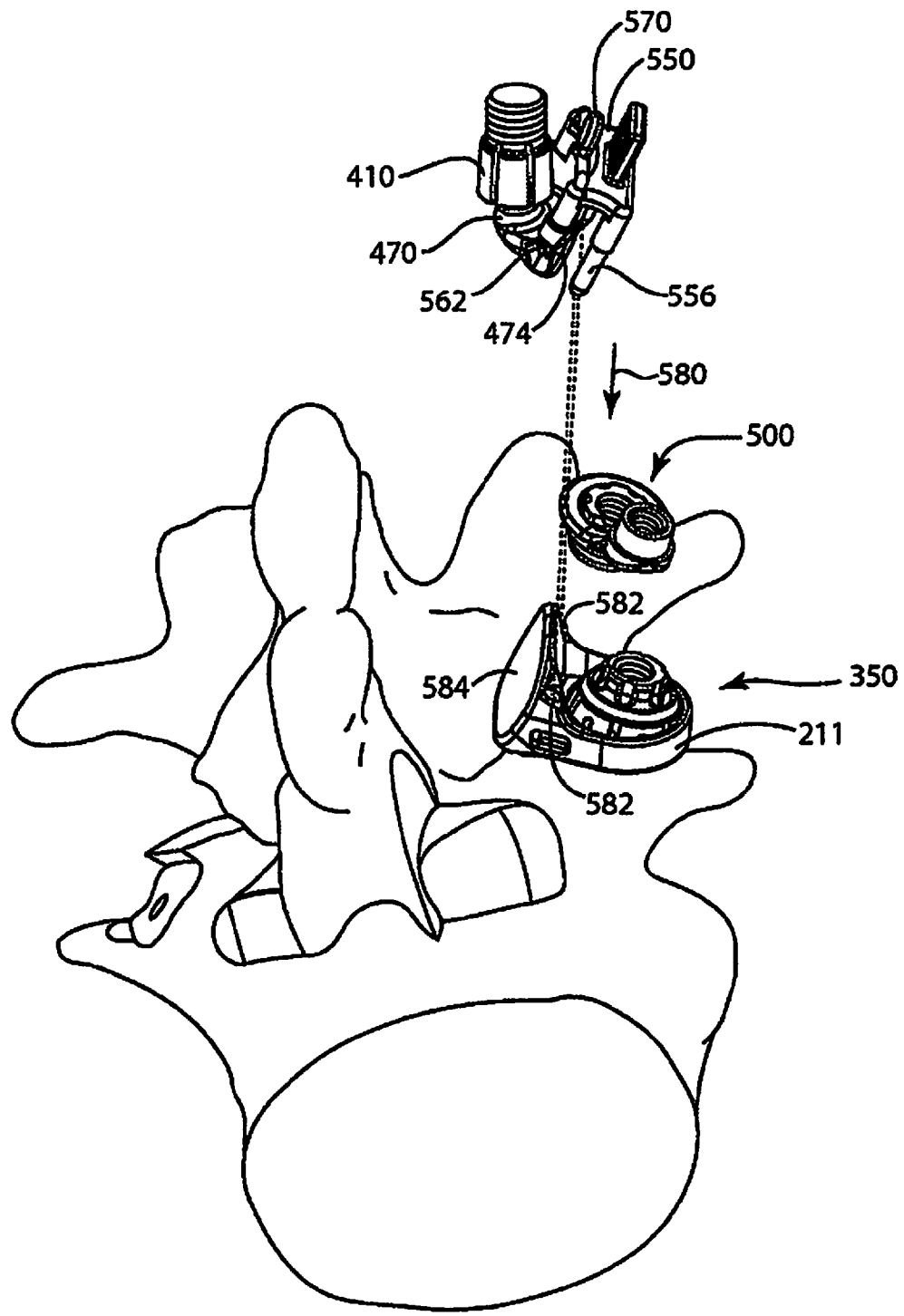
FIG. 20 is a perspective view of the clip of FIG. 17 coupled to an inferior facet joint implant, and the superior facet joint implant and fixation assembly of FIG. 8.

Referring to FIG. 20, a perspective view shows the inferior articular body 470 joined to the compressible member 410, attached to a clip 550. A direction arrow 580 indicates the direction in which the articular body, compressible member and clip may be moved to align them with a superior implant 211. The superior implant 211 is implanted in a pedicle via fixation assembly 350 previous to alignment with the inferior articular body 470, and a fixation assembly 500 is implanted into the adjacent pedicle. Using the handle 554, the clip may be moved until the superior posts 556 fit into openings 582 on the superior implant 211. Alternatively, as will be described below, clip 550 and inferior articular body 470 may be joined with strut 450 and with superior implant 211 into an assembly, and the assembly moved on to fixation members implanted in the pedicles.

Figure 21:
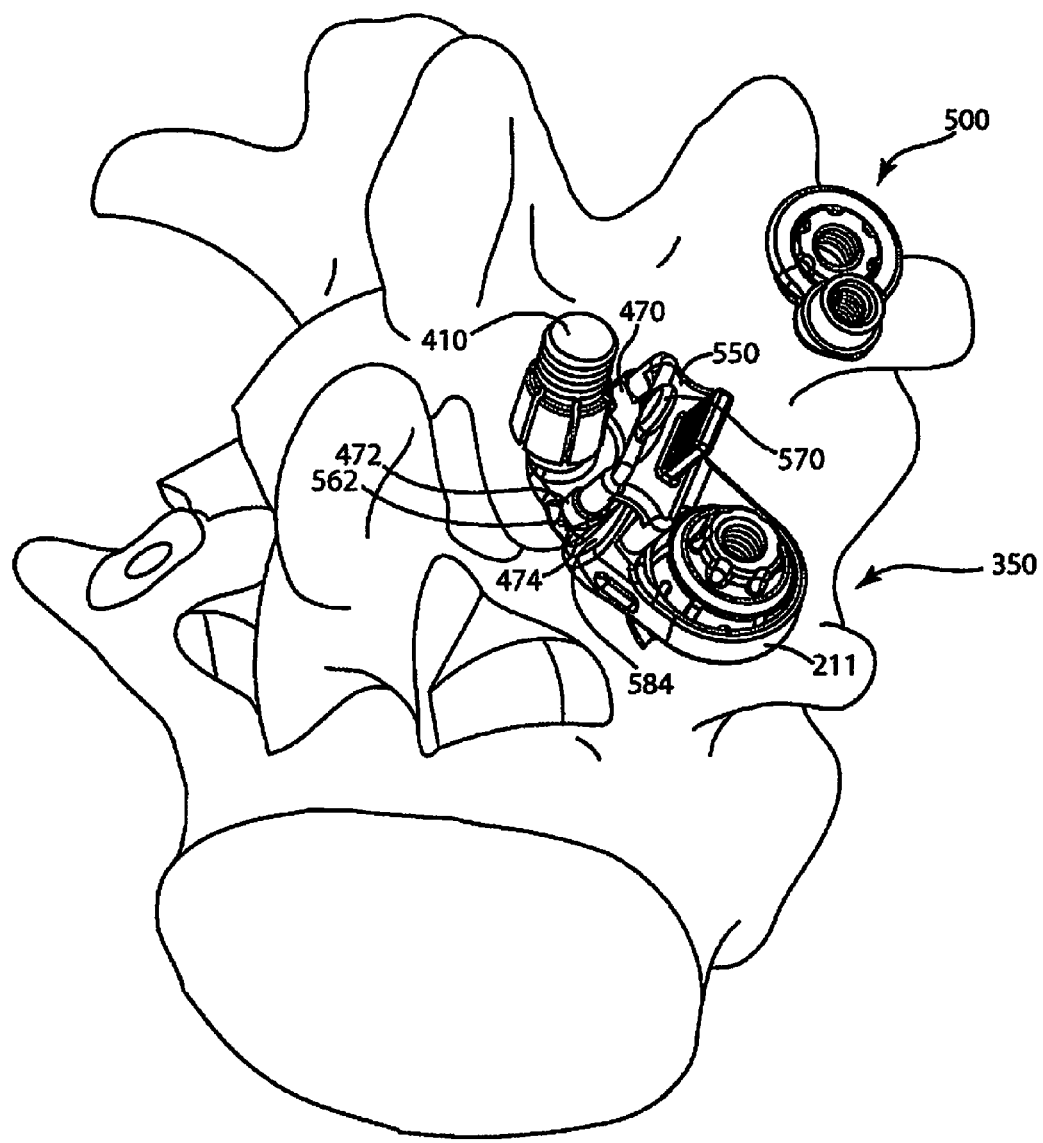
FIG. 21 is a perspective view of the inferior and superior facet joint implants of FIG. 20 joined by the clip of FIG. 17.

As seen in FIG. 21, when the posts 556 are fully inserted into the openings 582, inferior articulation surface 474 is aligned with superior articulation surface 584 in a preferred orientation. At this point, an appropriately sized and configured inferior strut may be chosen, its second end or split ring clamp coupled to the compressible member, and its first end or fixation portion coupled with and locked down to the fixation assembly 500. Additionally, a crosslink rod may be added and locked down as the attachment mechanism is locked down. To unlock and detach the clip 550, the plug 570 is removed, allowing the split ends 562 to deform and return to the first narrow configuration and making them narrow enough to be withdrawn through the tubes 472. Then the clip 550 may be removed.

Figure 22:
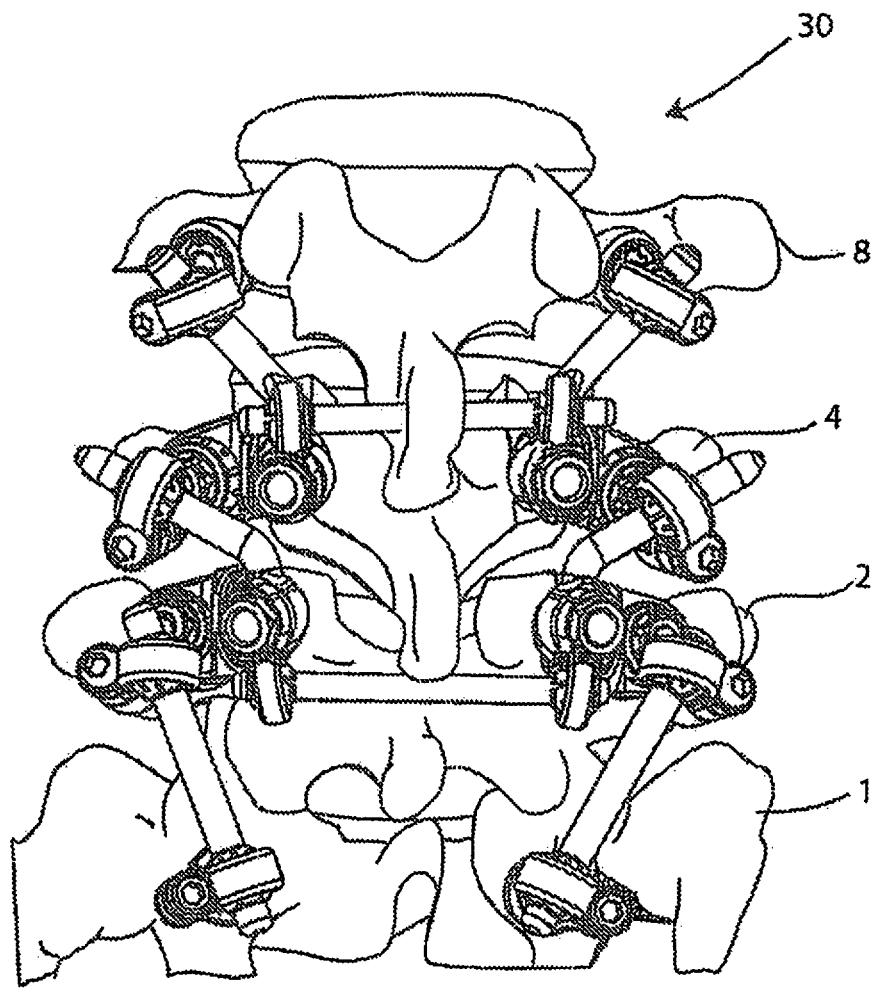
FIG. 22 is a perspective view of a multi-level facet joint replacement system implanted in a portion of a spine.

Referring to FIG. 22, a multi-level facet joint replacement system 30 is shown implanted in a portion of a spine. Between adjacent vertebrae 8 and 4, a first artificial facet joint replacement assembly replaces the natural facet joints. The first assembly is linked to a second artificial facet joint replacement assembly which replaces the natural facet joints between adjacent vertebrae 4 and 2. At the next level, the second artificial facet joint replacement assembly is linked to a fusion rod system which provides rigid fusion between vertebra 2 and the sacrum 1. Crosslink rods connect the left lateral assemblies with the right lateral assemblies.

Figure 23:
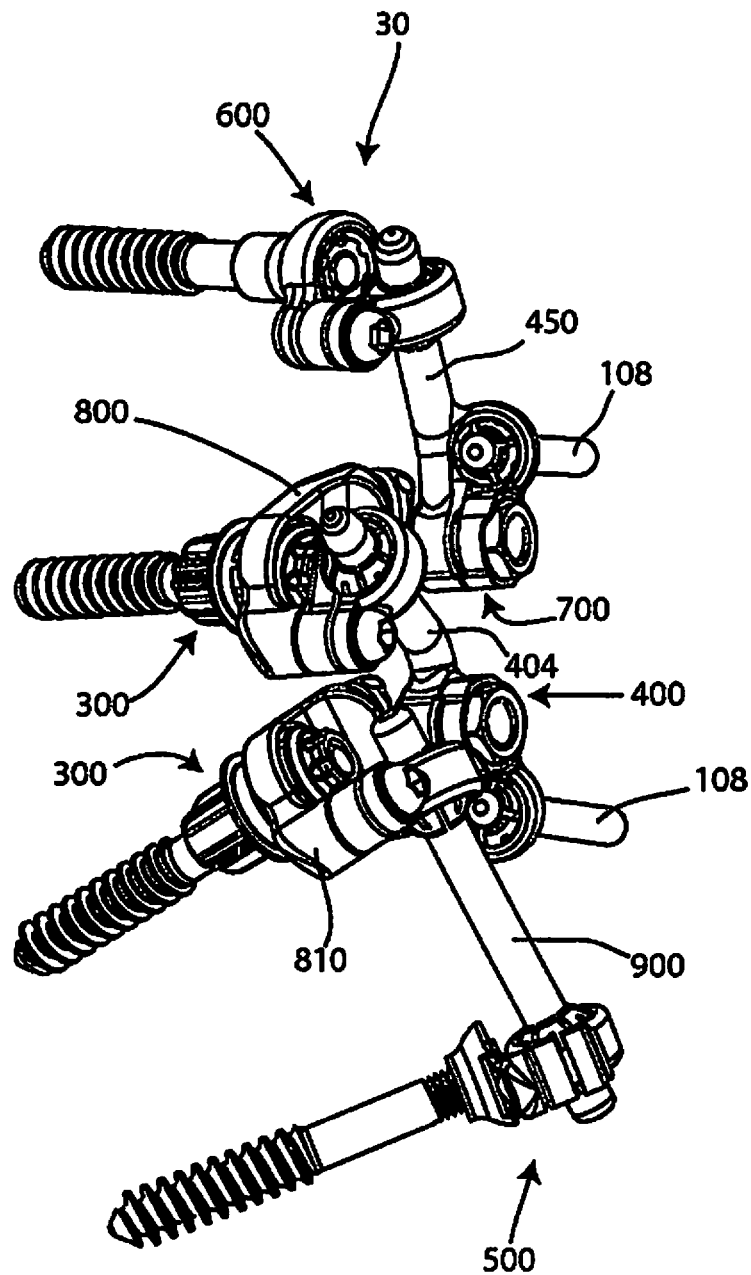
FIG. 23 is a lateral perspective view of a portion of the multi-level facet joint replacement system of FIG. 22.

Referring to FIG. 23, a lateral view shows the left lateral side of system 30. System comprises many of the same components as system 20. Viewing the system in a cephalad to caudal direction, system 30 includes a fixation assembly 600 configured to be implanted in a first vertebra. A fixation portion of inferior strut 450 is secured by a split clamp to fixation assembly 600, and forms part of inferior facet implant 700. Inferior facet implant 700 articulates with a first superior facet implant 800 which is secured to a first fixation assembly 300 which is configured to be implanted a second vertebra. An inferior strut 404 is secured by a split clamp to the first superior facet implant 800, and forms part of inferior facet implant 400. Inferior facet implant 400 articulates with a second superior facet implant 810 which is secured to a second fixation assembly 300 which is configured to be implanted in a third vertebra. A fusion rod 900 is secured by a split clamp to the second fixation assembly 300, and extends to a fourth vertebra or sacrum, where it is configured to be secured by a fixation assembly 500. Two crosslinks 108 are coupled to the inferior implants and extend across the sagittal plane to the right lateral side of the spine where they may be secured to right lateral side assemblies (as seen in FIG. 22). Multi-level applications of this system are not restricted to three or four levels; additional vertebral levels could be included by adding additional components including inferior implants, superior implants, crosslinks, and/or fusion rods. It is appreciated that the sizes and configurations of components included in system 30 may vary to fit various vertebral sizes, offset distances and configurations and particular patient anatomy. System 30 is polyaxially adjustable at each vertebral level.

Figure 24:
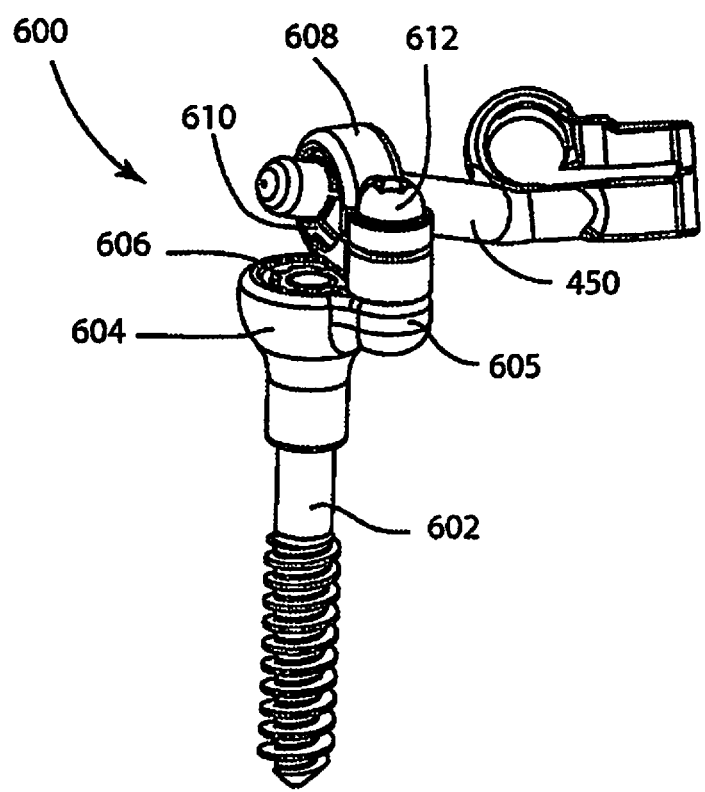
FIG. 24 is a perspective view of a fixation assembly of FIG. 22.

Referring to FIG. 24, a perspective view of fixation assembly 600, coupled with inferior strut 450 is shown. Fixation assembly 600 comprises fixation member 602, base member 604 with tapered pedestal 605, top nut 606, split ring clamp 608, split sphere 610 and set screw 612. Fixation assembly 600 is similar to fixation assembly 500 seen in FIGS. 16 and 17, and is assembled similarly. Base member 604 may be rotated about the axis of fixation member 602 prior to lockdown by top nut 606. Similarly, split ring clamp 608 may be rotated about the axis of the tapered pedestal 605 prior to lockdown by set screw 612. Base member 604 may extend farther along the fixation member and deeper into the bone than base member 504, and may include anti-rotation elements such as teeth, fins, and posts or studs, among others. It is appreciated that various component parts of the fixation assemblies herein disclosed may be mixed and matched to form a variety of other alternatives. For example, base members 504 and 604 may be substituted for one another if appropriate for the application, as may set screws 512 and 612. Similarly, fixation assembly 500 may be coupled with inferior strut 450, or another inferior strut or fusion rod, and fixation assembly 600 may coupled with inferior strut 404, or another inferior strut or fusion rod.

Figure 25:
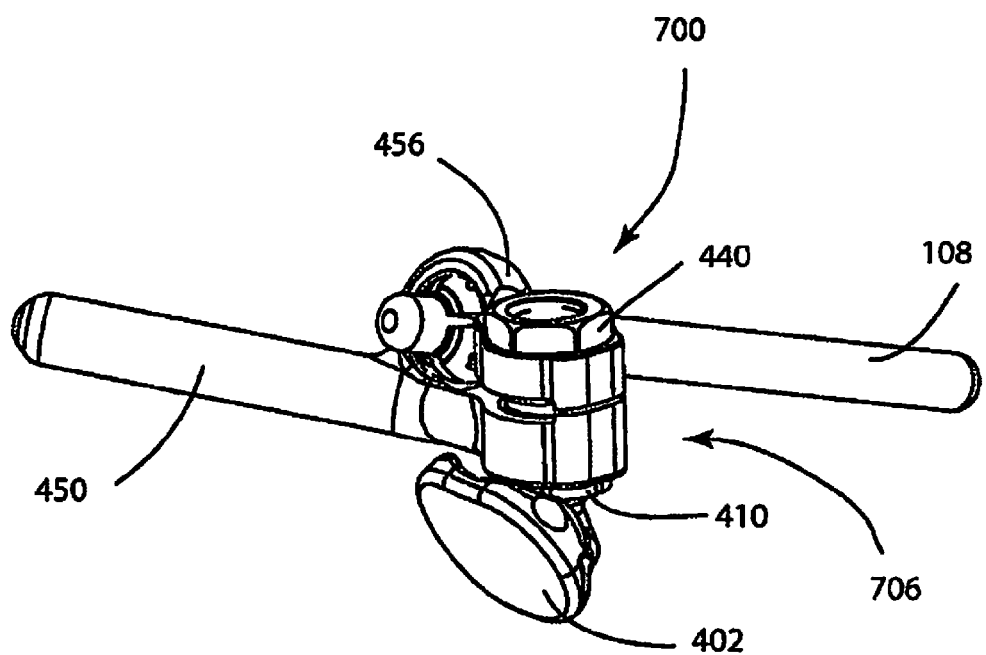
FIG. 25 is a perspective view of an inferior facet joint implant of FIG. 22.

Referring to FIG. 25, a perspective view of inferior facet implant 700 is shown coupled to crosslink rod 108. Inferior facet implant 700 comprises inferior articular body 402, inferior strut 450, and attachment mechanism 706 which couples the inferior articular body to the strut. Attachment mechanism 706 comprises compressible member 410, split clamp 456, and nut 440. Inferior facet implant 700 may be implanted in a multi-level application such as that seen in FIGS. 22 and 23, or in conjunction with a superior facet implant, or singly.

Figure 26:
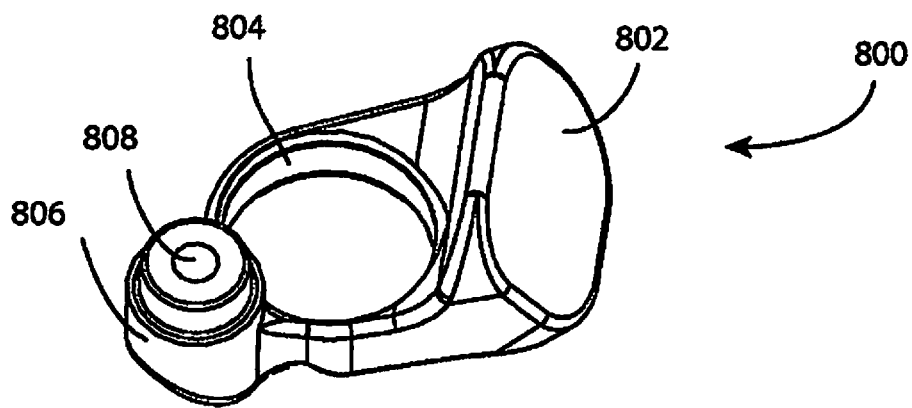
FIG. 26A is a perspective view of a superior facet joint implant of FIG. 22.
FIG. 26B is a perspective view of an alternate embodiment superior facet joint implant of FIG. 22.
Figure 26:
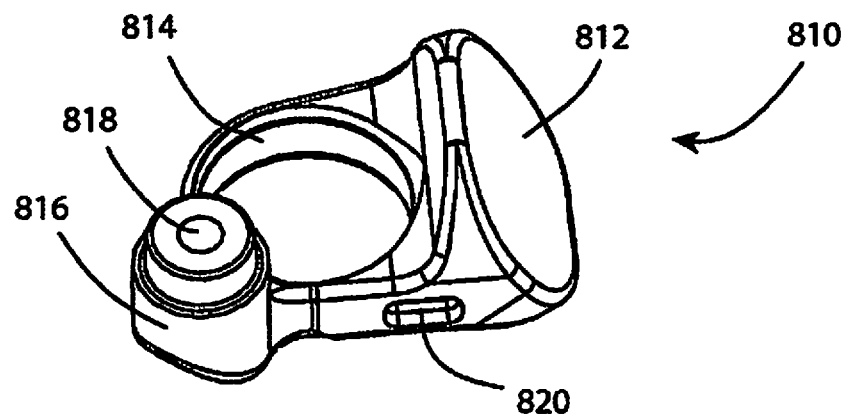
Figure 27:
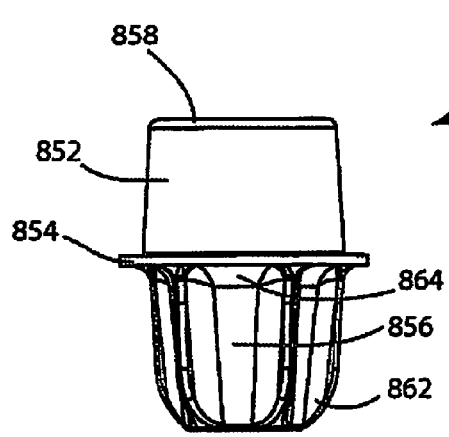
FIG. 27A is a lateral view of a fixation assembly base member.
FIG. 27B is a posterior view of the fixation assembly base member of FIG. 27A.
FIG. 27C is an anterior perspective view of the fixation assembly base member of FIG. 27A.
FIG. 27D is a cross-sectional view of the fixation assembly base member of FIG. 27A.
Figure 27:
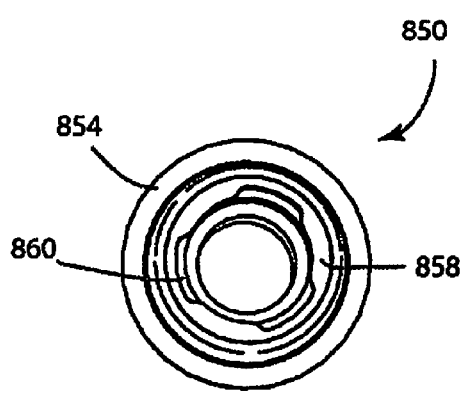
Figure 27:
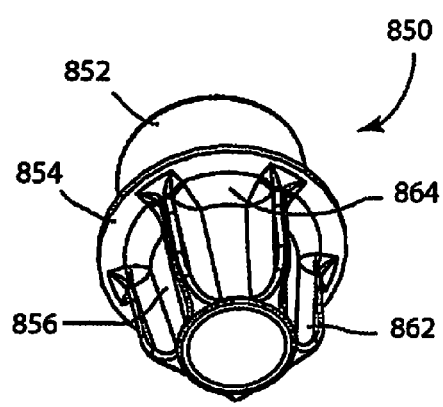
Figure 27:
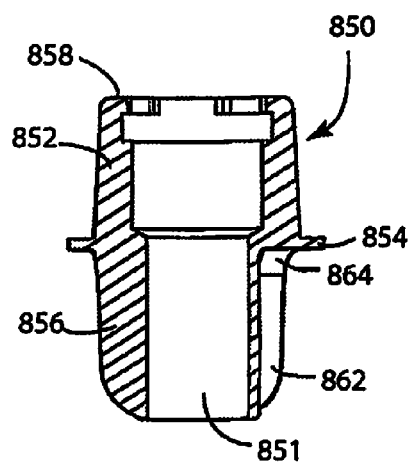

Referring to FIG. 26A, a perspective view of a superior facet implant 800 is shown, and in FIG. 26B, an alternative embodiment of a superior facet implant 810 is shown. Superior implant 800 comprises a superior articulating surface 802 and a fixation portion, or ring 804. Superior articulating surface 802 may be shaped to articulate with an inferior facet articulating surface. It is appreciated that the dimensions of the surface 802 may vary, as can the orientation and angle of the surface 802 relative to the remainder of the implant. The ring 804 is shaped to receive a split sphere such as sphere 306 or 356, thus allowing polyaxially adjustable coupling of the implant 800 to a fixation assembly such as fixation assembly 300. Adjacent the ring 804 is a pedestal 806 which includes a bore 808. The pedestal 806 may be tapered and is configured to receive a split ring clamp, and the bore 808 is configured to receive a set screw, to form an attachment mechanism capable of coupling an inferior strut, fusion rod or other rod-like member to the superior implant 800.

As seen in FIG. 26B, superior facet implant 810 may be similar to implant 800. Implant 810 comprises a superior articulating surface, a fixation portion or ring 814, a pedestal 816 and a bore 818. The implant further comprises at least one notch 820 configured to receive a tool. Either superior implant 800 or 810 may include features to allow the implant to be held in alignment with an inferior implant by a clip or gripping tool.

FIGS. 27-34 depict alternative embodiments of facet implant base members. Each base member comprises a tapered portion shaped to mate with an expandable member, or collet that is tapered inside and substantially spherical outside, such as split sphere 306, 356 or split shell 128. The tapered surface facilitates a taper lock between the base and the collet (and inferior or superior implant), thereby locking out adjustability between the implant and the base as described previous with regard to FIGS. 6 and 9. Below the tapered portion may be a flange to prevent subsidence and provide a stable surface against the adjacent bone, and to provide additional surface area for bone ingrowth. In addition, a generally cylindrical bone-engaging portion of the base extends down into the pedicle of the vertebra. The bone-engaging portion, which may also be tapered forming a conical shape, may have any number of fins or other features (3-7 in preferred embodiments) which may project into the surrounding bone to resist rotation forces. Each base has a lumen extending throughout both the tapered portion and bone-engaging portion to fit over a pedicle screw or other fixation member. The lumen may be cylindrical or may include a non-cylindrical indexing surface with one or more flat sections, shaped to receive a hexagonal driver or a driver of another shape, including triangular, square, pentagonal, or octagonal, among others. Additionally, each base may have engagement features such as notches or threads which allow a tool or gripping instrument to engage with and hold the base during implantation and lockout procedures. Implantation of each base may follow the same procedures as set forth previously for base 304. Bases with fins or other protruding anti-rotation features may require additional bone preparation steps such as broaching to create slots in the bone for the fins.

Each base member embodiment may differ in the number of fins that radiate outward from the center axis to resist rotation. The length, width and taper of fins or other anti-rotation features may vary. Other embodiments could use studs, pegs or posts instead of fins, or have slots in the bone-engaging portion that extend downward into the pedicle. Also, the flange and/or bone-engaging portion may be coated with bone in-growth material such as porous material or hydroxyapatite, among others. Additional embodiments may incorporate sawteeth to allow for self-guiding and/or self-cutting, therefore eliminating a separate preparation step. It is appreciated that the bases disclosed herein may be used with the fixation assemblies also disclosed herein, or in other orthopedic applications employing bone-engaging fixation members for which the anti-rotation or other properties of the bases are desired.

The combination of a base member such as those disclosed herein with a fixation member such as a pedicle screw may provide several advantages to a pedicle screw alone. The contact area between the pedicle and the fixation assembly over which bending loads are distributed will be increased, since the bone-engaging portion of each base provides a greater surface to bone contact area than a pedicle screw alone. According to Wolff's Law, a bone in a healthy person or animal will adapt to the loads it is placed under. If loading on a particular bone increases, the bone will remodel itself over time to become stronger to resist that sort of loading. Increasing the bone contact area through the use of a base member may therefore result in strengthening of a larger portion of the bone around the implant fixation assembly. Additionally, less load may be placed on the pedicle screw, which may result in decreased likelihood of loosening of the screw over time.

FIG. 27A is a side view of a facet implant base member 850; FIG. 27B is an end view of the base 850; FIG. 27C is a perspective view of the base 850; and FIG. 27D is cross-sectional view of the base 850. Base 850 comprises a tapered portion 852 separated from a bone-engaging portion 856 by a flange 854. A lumen 851 extends the length of the base, the lumen shaped to receive a fixation member such as 302, 352, 502, or a pedicle screw, among others. A first end 858 includes several notches 860 which are engagement features shaped to mate with a placement and/or lockout tool. In this embodiment, five evenly spaced fins 862 project outward from the bone-engaging portion 856. The fins 862 may prevent rotation of the base 850 in the pedicle. A fillet 864 is located between each fin and the adjacent fin and provides a transition between the flange 854 and the bone-engaging portion 856. In other embodiments of the base, there may be fewer or more fins, and the fins may be evenly or unevenly spaced, or paired, or grouped. The morphology of the fins may vary; some fins may have sharp, well-defined edges while others may have more rounded edges. The fins may taper between the flange and the distal end of the bone-engaging portion. Similarly, the sizes of the fillets 864 may vary; a larger fillet will provide a less sharp, more continuous transition between fins. Providing more gradual, less acute transitions between features on the base may prevent the occurrence of low-load areas where less bone in-growth might occur.

Figure 28A:
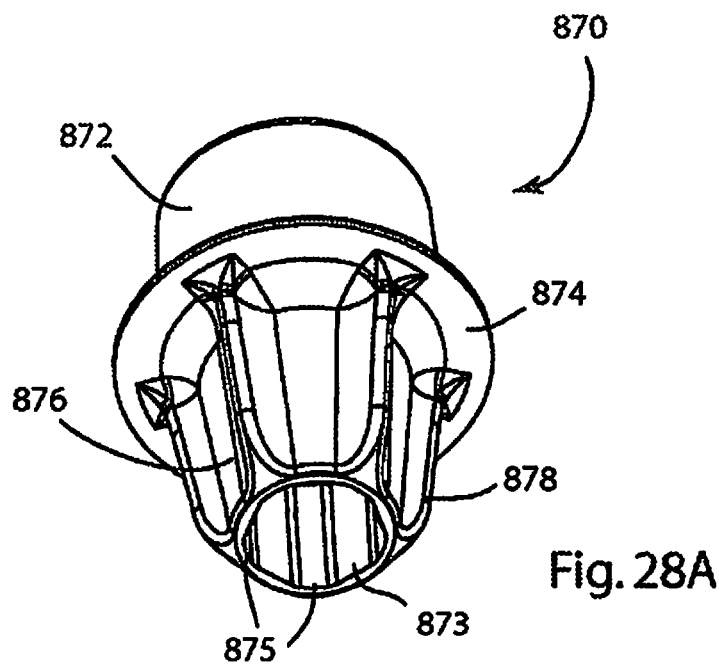
FIG. 28A is a lateral perspective view of an alternate fixation assembly base member.
Figure 28B:
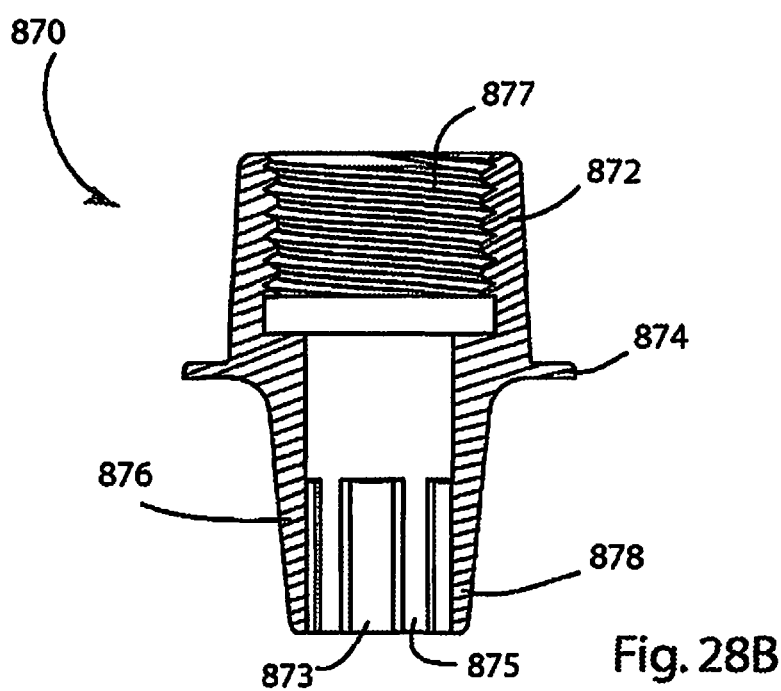
FIG. 28B is a cross-sectional view of the fixation assembly base member of FIG. 28A.

Referring to FIG. 28, an alternative embodiment of an implant base member is shown. Implant base 870 has a tapered portion 872, a flange 874 and a bone-engaging portion 876. A plurality of fins 878 extend outward from the bone-engaging portion 876. The central lumen 871 includes flat sections 873 interspersed with curved sections 875, allowing for engagement with a tool such as a pentagonal driver (not shown). The flat sections may provide a practitioner with immediate orientation of the fins 878 relative to the bone screw with which the base is coupled, as well as to broached slots in the bone. The curved sections 875 have a diameter outside the dimensions of the flat sections, allowing rotary bone preparation tools to be passed through and used in the lumen. The tapered portion includes threads 877 which may extend throughout the tapered portion as shown or, in other embodiments, may extend only partially through the tapered portion. The threads 877 are configured to engage with a placement and/or lockout tool, which may provide force to effect a taper lock between an implant and the base, as set forth previously.

Figure 29:
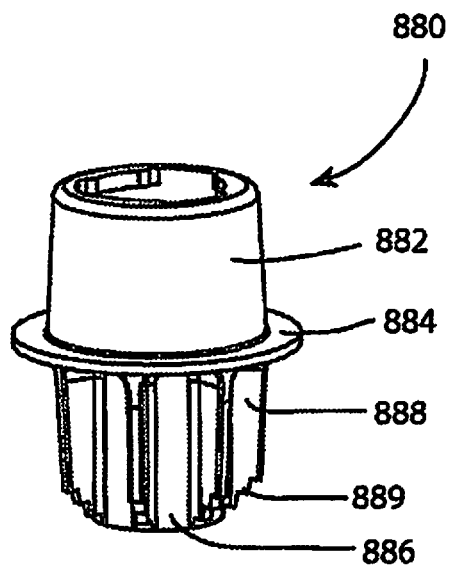
FIG. 29 is a lateral perspective view of an alternate fixation assembly base member.

Referring to FIG. 29, another alternative embodiment of an implant base member is shown. Implant base 880 has a tapered portion 882, a flange 884 and a bone-engaging portion 886. A plurality of fins 888 extend outward from the bone-engaging portion 886. Each fin 888 is serrated with several teeth 889, which may provide self-broaching of the bone during implantation of the base.

Figure 30:
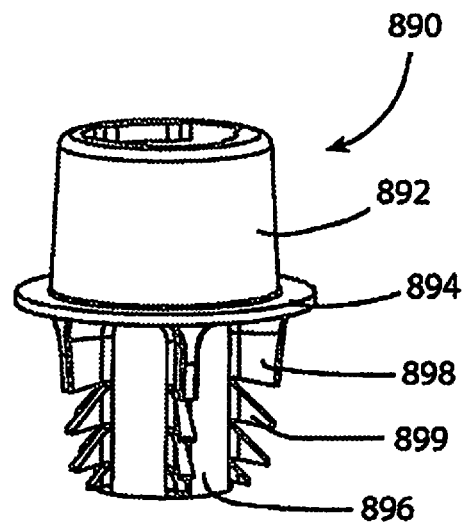
FIG. 30 is a lateral perspective view of an alternate fixation assembly base member.

Referring to FIG. 30, yet another alternative embodiment of an implant base member is shown. Implant base 890 has a tapered portion 892, a flange 894 and a bone-engaging portion 896. A plurality of jagged fins 898 extend outward from the bone-engaging portion 896. Each fin 898 comprises a series of teeth 899 which may be graduated in size. Similar to implant base 880, the teeth may provide self-broaching during implantation, and may reduce the bone preparation needed prior to implantation.

Figure 31:
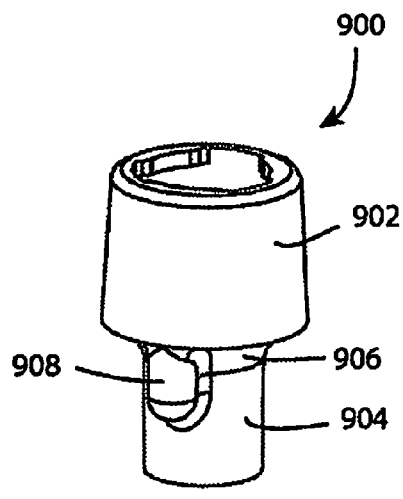
FIG. 31 is a lateral perspective view of an alternate fixation assembly base member.

Referring to FIG. 31, another alternative embodiment of an implant base member is shown. Implant base 900 comprises a tapered portion 902 and a bone-engaging portion 904. A curved transitional area 906 connects the tapered portion and the bone-engaging portion. The transitional area serves a similar function as the flange in other embodiments, preventing subsidence of the implant. Two pegs 908, which may prevent rotation of the base, protrude outward from the bone-engaging portion 904.

Figure 32:
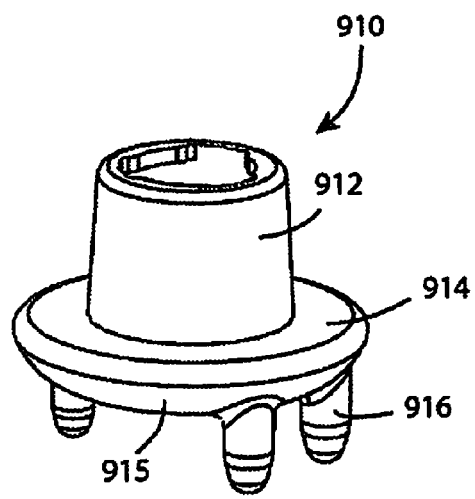
FIG. 32 is a lateral perspective view of an alternate fixation assembly base member.

Referring to FIG. 32, another alternative embodiment of an implant base member is shown. Implant base 910 comprises a tapered portion 912 and a bone-engaging portion 914. In this embodiment, the dish-shaped bone-engaging portion 914 has a greater diameter than the tapered portion 912. Bone-engaging portion 914 has a spherical bone-contacting surface 915. The configuration of the bone-engaging portion 914 may prevent subsidence of the implant, distribute the implant load over a larger surface area, and provide increased surface area for bone ingrowth. A plurality of pegs 916 protrude from the bone-engaging portion 914 and may prevent rotation of the base. The pegs 916 are positioned farther away from the central axis of the base 910, in comparison to the configuration of base 900 and pegs 908.

Figure 33:
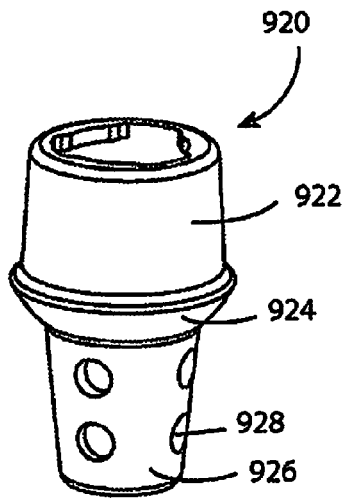
FIG. 33 is a lateral perspective view of an alternate fixation assembly base member.

Referring to FIG. 33, another alternative embodiment of an implant base member is shown. Implant base 920 comprises a tapered portion 922, a spherical transition portion 924 and a bone-engaging portion 926. Bone-engaging portion 926 is tapered and includes a plurality of holes 928 which open into the central cannulated area, and may allow additional bone ingrowth. Bone-engaging portion 926 may provide a narrower profile allowing for less disturbance of the pedicle during preparation and implantation.

Figure 34:
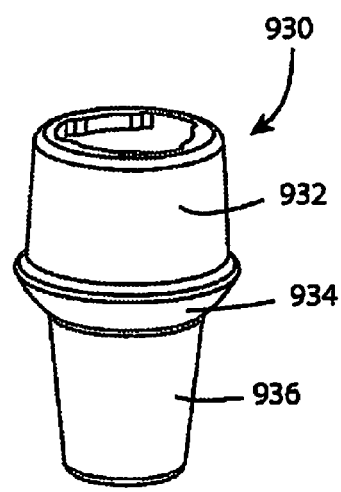
FIG. 34 is a lateral perspective view of an alternate fixation assembly base member.

Referring to FIG. 34, another alternative embodiment of an implant base member is shown. Implant base 930 comprises a tapered portion 932, a spherical transition portion 934 and a tapered bone-engaging portion 936.

Figure 35:
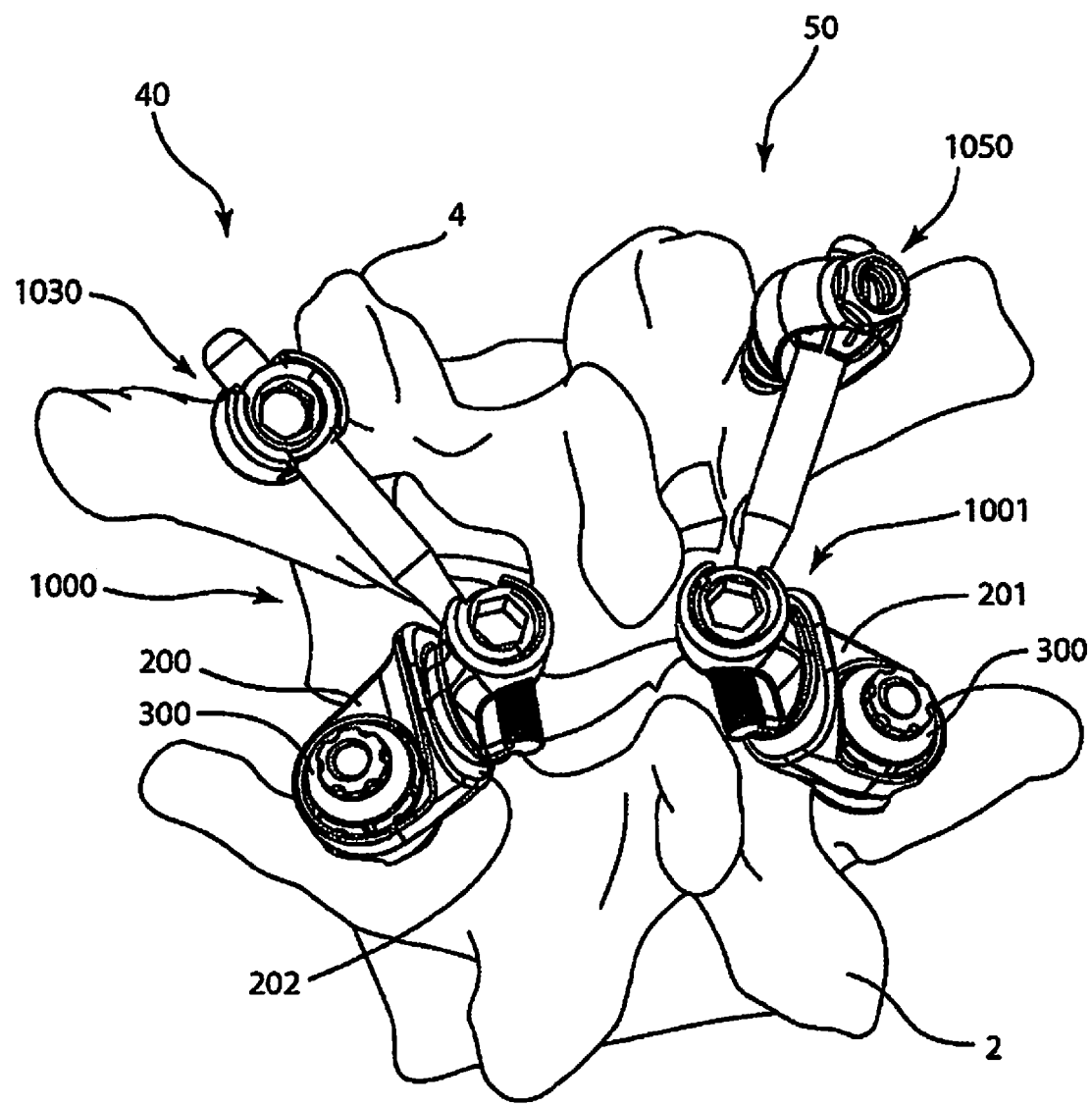
FIG. 35 is a posterior perspective view of a bi-lateral low-profile facet joint replacement system implanted into two adjacent vertebrae.

FIG. 35 depicts a low profile facet replacement system 40 implanted on the left side of two adjacent vertebrae 2, 4, and another low profile facet replacement system 50 implanted on the right side. System 40 comprises a superior facet implant 200 anchored to the pedicle by fixation assembly 300, and an inferior facet implant 1000 anchored by a fixation assembly 1030. System 50 comprises a superior facet implant 201 anchored by fixation assembly 300, and an inferior facet implant 1001 anchored by a fixation assembly 1050. Systems 40 and 50 are mirror images of one another, with the exception that two different fixation assemblies, 1030 and 1050, are used to anchor the inferior implants. In other embodiments of the invention, both systems 40 and 50 may include the same fixation assemblies. A crosslink (not shown) may be coupled to each assembly 40, 50 to provide a crosslink connection between the assemblies. The low profile design of the system results in an inferior facet joint implant that may have a reduced anterior-posterior dimension when compared to other inferior facet joint implants.

Referring to FIG. 36A, a perspective view of inferior facet implant 1000 is shown, and in FIG. 36B an alternative perspective view of the implant is shown. An implant articular surface is coupled with a low-profile capture feature on the posterior side. The capture feature accepts a strut that has a spherical end. The spherical end mates with a concavity in the capture feature shaped to allow polyaxial range of motion. A locking member, or set screw may be tightened down, applying compression forces on the sphere, thereby locking it out. Specifically, inferior implant 1000 comprises an inferior articulation body 1002, an inferior strut 1004 and a set screw 1006. Inferior articulation body 1002 comprises an inferior articulation surface 1008, a capture member 1010, and an attachment feature 1012. Attachment feature 1012 is shaped to mate with a crosslink clamp attachment (not shown).

Figure 37:
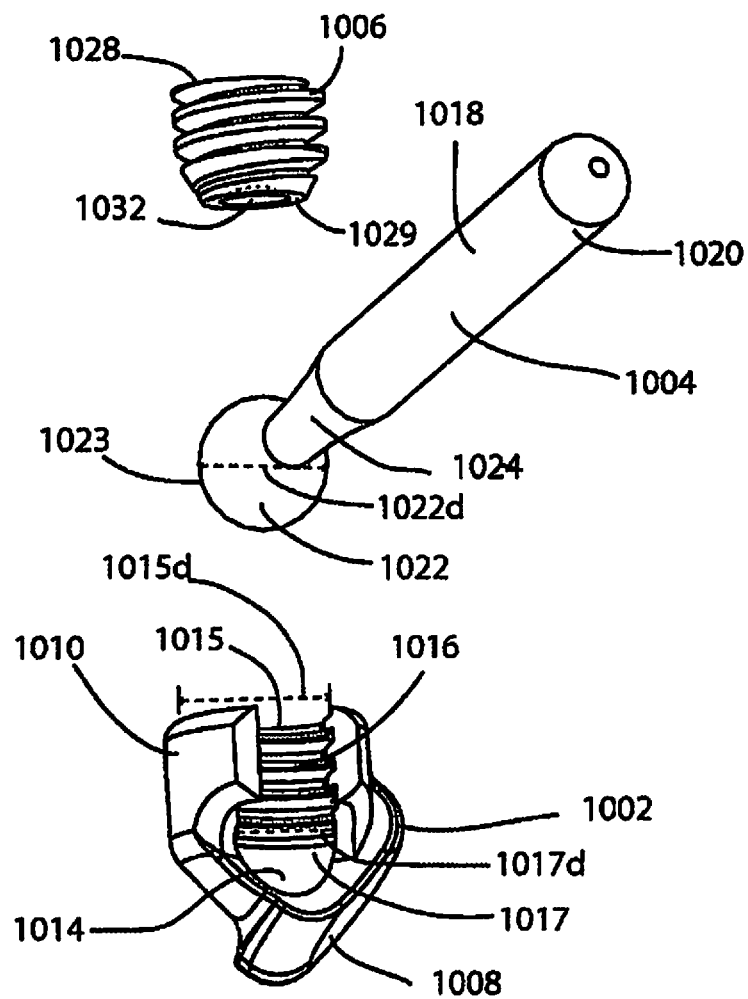
FIG. 37 is an exploded view of the low profile inferior facet implant of FIG. 35.

Referring to FIG. 37, an exploded perspective view of implant 1000 is shown. Inferior articulation body 1002 may be monolithic, and includes the inferior articulation surface 1008 which is shaped to replace a natural articular surface, and to articulate with a superior articulation surface. The capture member 1010 is coupled to body 1002 and may be formed monolithically with the body 2002. The capture member 1010 comprises a spherical concavity 1014 shaped to capture a spherical end of the inferior strut 1004. Posterior to the spherical concavity 1014 is a substantially circular concave threaded wall 1016 which is shaped to receive the set screw 1006. A generally posterior first opening 1015 creates access to the concave threaded wall 1016 and the spherical concavity 1014. Adjacent to the spherical concavity 1014 and anterior to the concave threaded wall 1016 is a second opening 1017 which allows for polyaxial adjustability of the inferior strut 1004.

The inferior strut 1004 comprises a strut body 1018 with a rod-like fixation portion or first end 1020 and a spherical second end 1022 which has a hemispherical surface 1023. The hemispherical surface is uninterrupted, meaning the surface is continuous across the hemisphere and there are no breaks or interruptions in the hemispherical surface such as, for example, connection features extending outwardly from the hemispherical surface. However, the surface may be roughened to facilitate engagement with the spherical concavity. A sphere diameter 1022d is less than a diameter 1015d of the first opening 1015, but greater than a diameter 1017d of the second opening 1017, allowing the spherical second end 1022 to be captured in the spherical concavity 1014. The strut body 1018 may further include a tapered portion 1024 between the first and second ends. Features of the inferior strut 1004 may vary, including but not limited to the size of the spherical second end, and the degree of taper and placement of the tapered portion. The first 1020 and second 1022 ends of the strut may be linearly oriented relative to one another resulting in a radially symmetrical strut, or they may be oriented at an angle. The set screw 1006 is exteriorly threaded, and may include a drive feature 1026 (visible in FIG. 36A) at a first end 1028. At a second end 1029, the screw includes a spherical pocket 1032 shaped to mate with the spherical second end 1022 of the strut 1004.

Assembled as in FIGS. 36A and 36B, the spherical second end 1022 of the strut 1004 fits into the spherical concavity 1014 of the capture member 1010, and the first end 1020 of the strut extends out of the capture member 1010. Prior to lockout, the second opening 1017 allows room for polyaxial range of motion adjustment of the strut 1004 relative to the articular surface 1008. The strut 1004 may be positioned with at least 40 degrees of variability inside the capture member before lockout. Both the second end 1022 and the spherical concavity 1014 may include roughened surfaces to help facilitate engagement and lock-out between the strut and the capture member. The set screw 1006 is threadibly engaged in the threaded wall 1016, and the spherical pocket 1032 of the set screw mates with the spherical second end 1022 of the strut. After adjustment, the set screw 1006 is tightened down, applying compression forces on the spherical second end, locking out all motion of the strut 1004 relative to the articular surface 1008. When locked down, the set screw 1006 may be entirely positioned within the capture member 1010, contributing to the low profile characteristics of the system.

Figure 36:
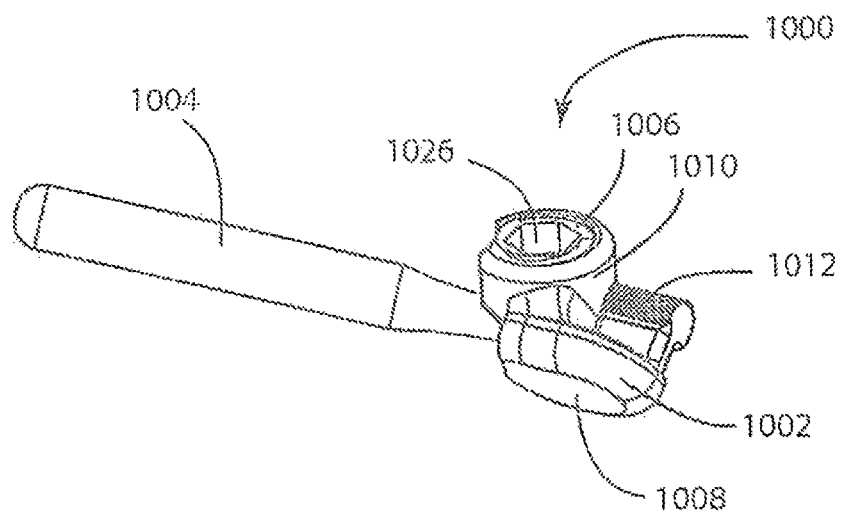
FIG. 36A is a perspective view of the low profile inferior facet implant of FIG. 35.
FIG. 36B is an alternate perspective view of the low profile inferior facet implant of FIG. 35.
Figure 36:
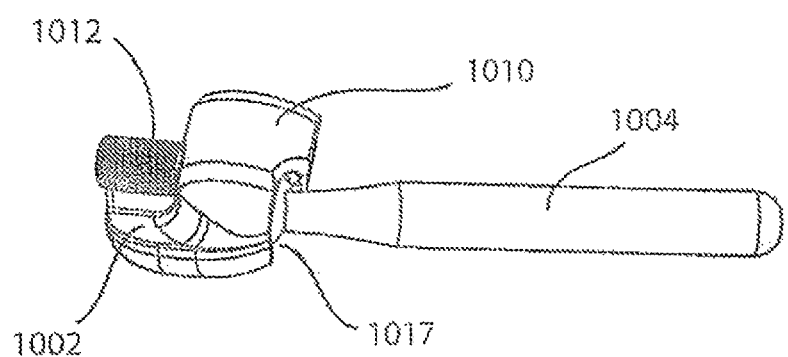

System 40 may be implanted as follows, and it is understood that system 50 may be implanted in a similar manner with a similar or different fixation assembly in the cephalad vertebra 4. The pedicle of the caudal vertebra 2 is prepared for fixation member 302 and tapered base member 304 which comprise fixation assembly 300. The pedicle of cephalad vertebra 4 is prepared for fixation assembly 1030, described in more detail below. Existing natural facet surfaces may be resected as necessary. Fixation assembly 300 is anchored in the prepared pedicle of caudal vertebra 2, and fixation assembly 1030 is anchored in the cephalad vertebra 4. Superior implant 200 is be placed and locked on to fixation assembly 300 so that the articular surface 202 is at a specified facet angle. The spherical second end 1022 is placed in the capture member 1010 of the inferior articular body 1002, and the set screw 1006 may be engaged with the capture member 1010 but not tightened down. The fixation portion, or first end 1020 of inferior implant 1000 is placed in the fixation assembly 1030 but not locked down. Inferior implant 1000 is polyaxially adjusted to align inferior articulation surface 1008 with superior articulation surface 202, and locked down by tightening the set screw 1006. As seen in FIGS. 35 and 36, the capture member 1010 is medially and posteriorly positioned relative to the inferior articular surface 1008. Additionally, the entire inferior articular surface 1008 may be positioned laterally of the sagittal plant of the caudal and cephalad vertebrae 2, 4. The fixation assembly 1030 is locked down. Alternatively, the fixation assembly 1030 may be locked down first, followed by the inferior implant 1000. Following lock-down of the fixation assemblies, the superior and inferior implants may articulate along their respective articular surfaces, preserving a level of spinal motion.

In an alternative order of assembly, a fixation assembly 300 may be anchored in a prepared pedicle of caudal vertebra 2, and a fixation assembly 1030 anchored in a prepared pedicle of cephalad vertebra 4. Superior implant 200 and inferior articular body 1002 may be clipped together so their articulating surfaces are aligned, as described previously, and dropped on to the fixation assembly 300. The spherical second end 1022 of inferior implant 1000 is placed in the capture member 1010 of the inferior articular body 1002, and the first end 1020 of the inferior implant 1000 is pivoted into the saddles of fixation member 1030. Inferior implant 1000 is locked down by actuating set screw 1006, and fixation member 1030 is locked down by actuating its set screw.

Figure 38:
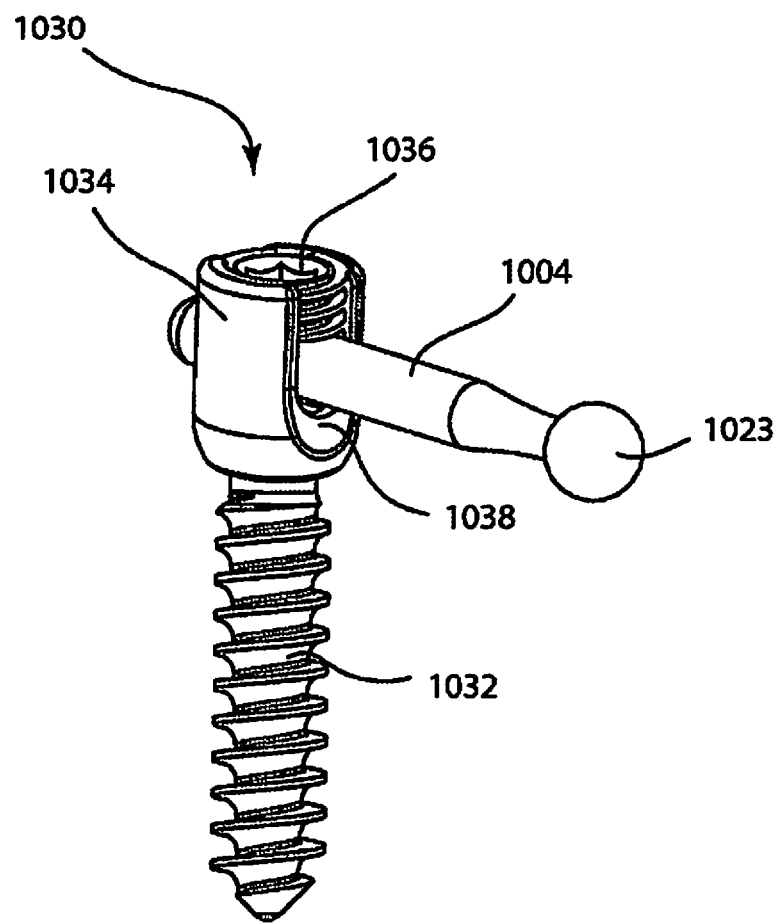
FIG. 38 is a perspective view of a fixation assembly of FIG. 35.

Referring to FIG. 38, a perspective view of fixation assembly 1030 and inferior strut 1004 is shown. Fixation assembly 1030 comprises a fixation member 1032, a capture member 1034, and a set screw 1036. A pair of saddles 1038 in the capture member 1034 is shaped to hold the fixation portion of strut 1004 or another rod-like member. During assembly, capture member 1034 may be rotated about the axis of the fixation member 1032. Prior to lockdown, the length of the strut 1004 extending through the capture member 1034 may be adjusted. Lockdown is attained by turning the set screw 1036, thereby compressing the strut 1004 within the saddles 1038.

Figure 39:
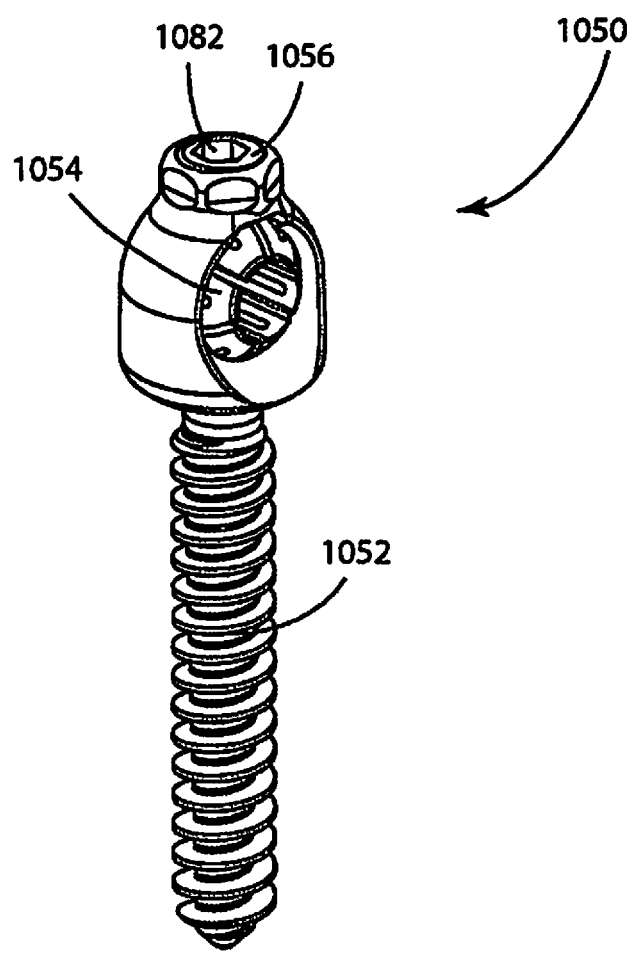
FIG. 39 is a perspective view of another fixation assembly of FIG. 35.

Referring to FIG. 39, a perspective view of an inferior strut 1004 captured in a fixation assembly is shown. Bone anchor assembly 1050 comprises an eyelet screw body 1052, a compression sphere 1054, and a set screw 1056. The eyelet screw body 1052 is of monolithic, one-piece construction, although alternative embodiments could include separate screw and eyelet pieces. Bone anchor assembly 1050 provides polyaxial and linear adjustments to allow for variations in pedicle to pedicle offset dimensions.

Figure 40:
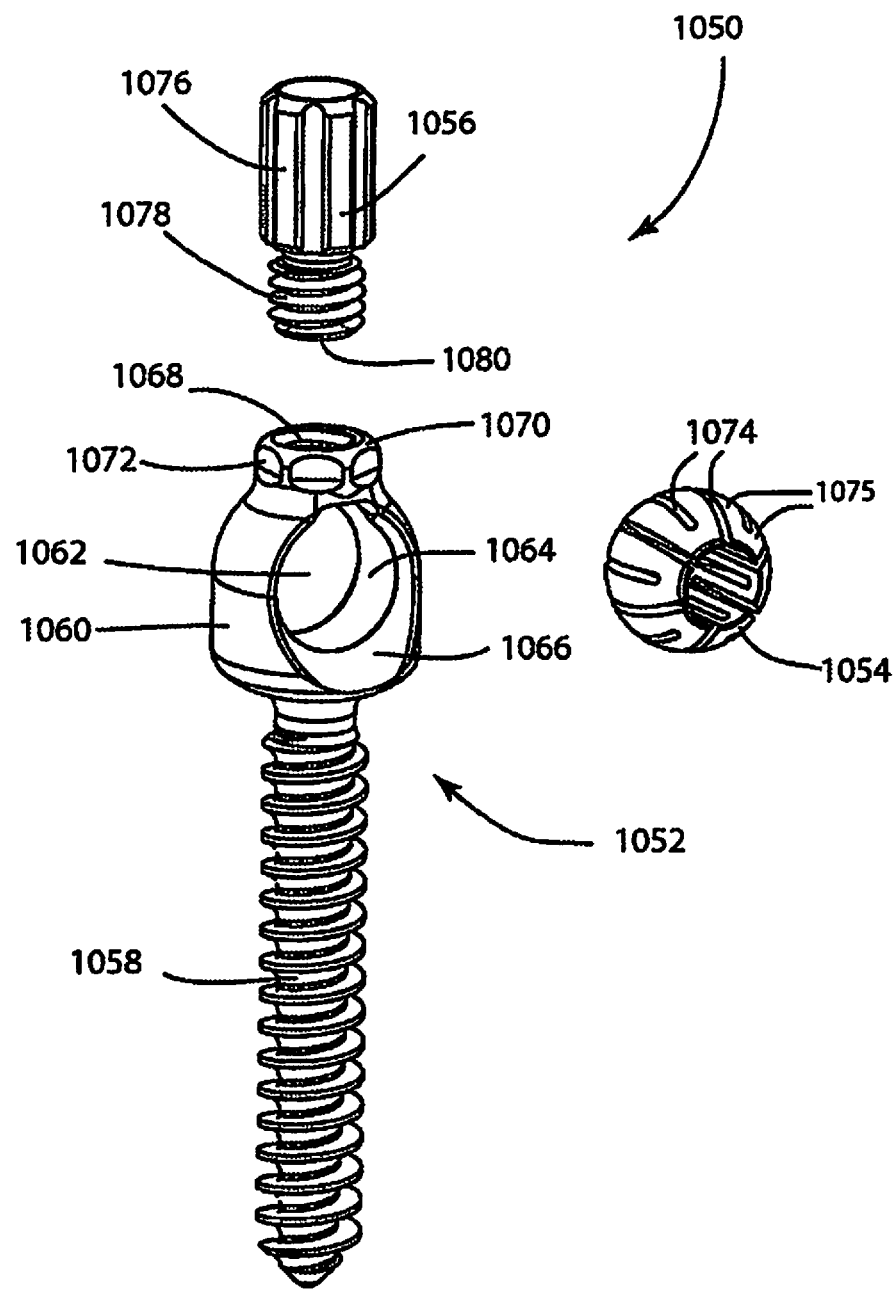
FIG. 40 is an exploded view of the fixation assembly of FIG. 39.

FIG. 40 is an exploded view of bone anchor assembly 1050. Eyelet screw body 1052 comprises a fixation portion or threaded bone-engaging portion 1058, and an eyelet portion, or coupling member 1060. The coupling member comprises a closed loop portion, through which a passageway 1062 extends in an orthogonal orientation relative to the bone-engaging portion 1058. A concave wall 1064, shaped to substantially capture the compression sphere 1054, encircles the passageway 1062. A countersink 1066 flares out from the concave wall 1064 to the outer surface of the coupling member 1060. The countersink 1066 provides increased surface area which may contribute to improved bone ingrowth. Posterior to, and coincident with the center of the passageway 1062, is a threaded aperture 1068 encircled by a ring 1070. The threaded aperture 1068 may be coaxial with the longitudinal axis of the threaded bone-engaging portion 1058, as in FIG. 40. On the exterior of the ring 1070 may be a drive feature 1072.

The compression sphere 1054 comprises a plurality of slots 1074 interleaved with curved wall segments 1075. Multiple slots and wall segments allow for local deformations, providing more points of registration against the concave wall 1064 when compressed and inserted into the passageway 1062. The compression sphere 1054 has a compressible bore shaped to receive an elongated member such as strut 1004. The compression sphere may have an uncompressed state, a first compressed state in which it is compressed sufficiently to fit into the passageway 1062 of the closed loop portion, with the outer diameter of the sphere equal to the diameter of the passageway. The sphere may further have a second compressed state in which the slots 1074 and wall segments 1075 are deformed about the strut 1004 sufficiently to both prevent movement of the strut and fix the position of the sphere relative to the coupling member.

The set screw 1056 is of a twist-off configuration, in which a head segment or drive element 1076 fractures from a threaded portion 1078 at a predetermined torque. The threaded portion 1078 has a spherical recess 1080 which is shaped to mate with the compression sphere 1054. The entire set screw 1056 may be cannulated, and the threaded portion 1078 has an internal drive feature 1082 (visible in FIG. 39) which may be a hex drive feature.

Figure 41:
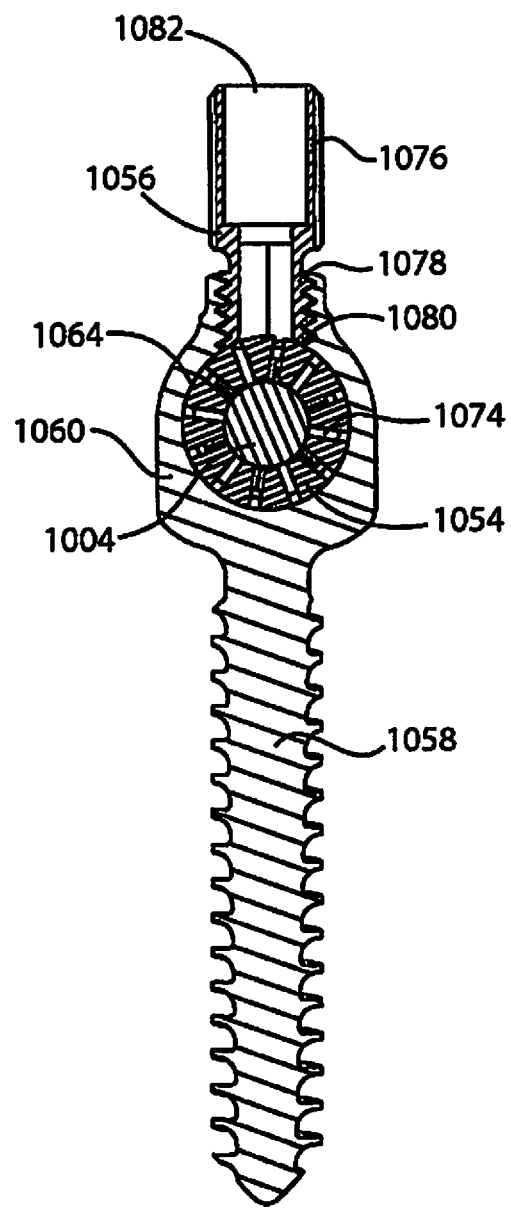
FIG. 41 is a cross-sectional view of the fixation assembly of FIG. 39.

FIG. 41 is a cross-sectional view of bone anchor assembly 1050 with an inferior strut 1004 locked in the compression sphere 1054. During implantation, eyelet screw body 1058 is driven into a prepared pedicle, with compression sphere 1054 compressed to the first compressed state and captured in the passageway 1062 of the closed loop portion. The fixation portion of inferior strut such as strut 1004, or other strut or rod which the bone anchor assembly 1050 is anchored, is inserted through the compression sphere 1054. The strut and sphere may be polyaxially rotated to attain a desired orientation. The combination of the rotatable sphere and flared countersink 1066 allows for a range of motion of +/−35 degrees, for a total included angle of 70 degrees. Also, the length of the strut extending through the sphere 1054 may be adjusted to attain a desired pedicle to pedicle offset. When the desired position and orientation of the strut are attained, the set screw 1056 is threaded through the threaded aperture 1068 and torqued to lock out movement between the sphere, strut and eyelet. The set screw 1056 directly contacts the compression sphere 1054, the spherical recess 1080 mates with the compression sphere 1054 and the sphere 1054 is compressed around the strut 1004, and deformed within the closed loop portion, forming many areas of contact between the sphere 1054 and the concave wall 1064. At this second compressed state, movement of the strut is prevented and the sphere is locked in a fixed position relative to the coupling member. At a predetermined torque, the drive element 1076 fractures from the threaded portion 1078 of the set screw 1056.

Figure 42:
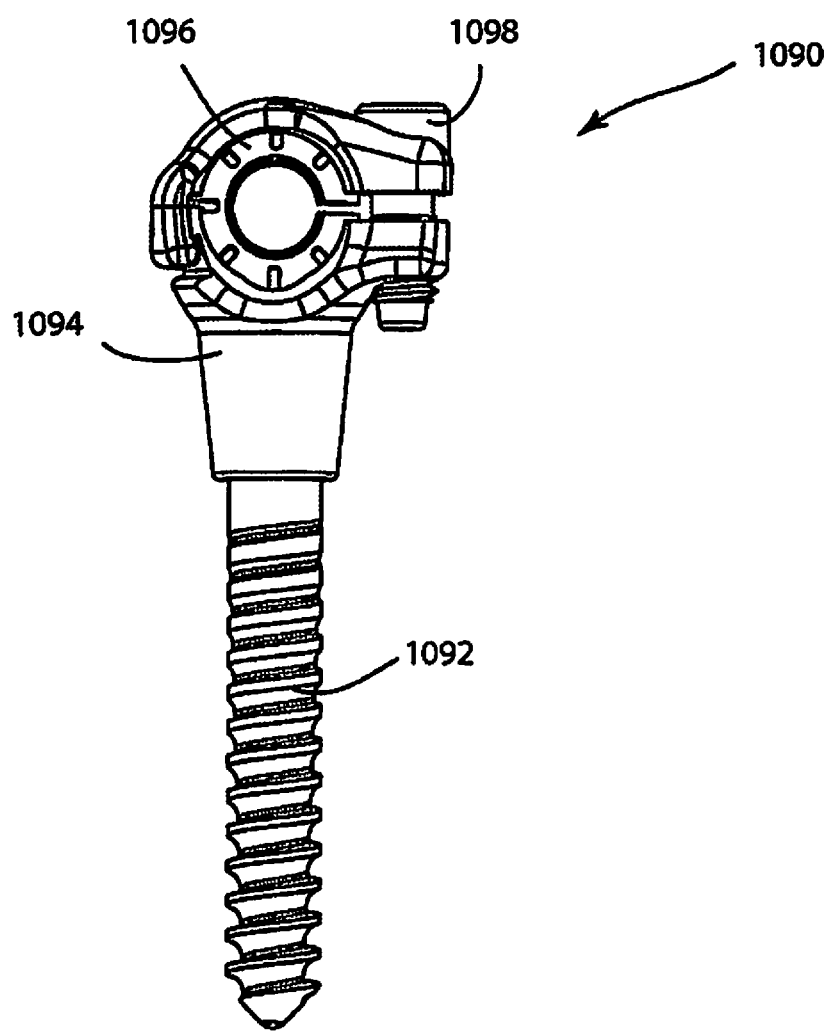
FIG. 42 is a perspective view of an alternate fixation assembly.

FIG. 42 illustrates an alternative fixation assembly 1090, which may be described as a split eyelet clamp bone anchor assembly. Fixation assembly 1090 comprises fixation member 1092, a split ring clamp 1094, a compression sphere 1096, and a set screw 1098. Fixation assembly 1090 may be used to anchor an inferior facet joint implant such as implant 1000 or implant 400, or another rod-like member such as a fusion rod, to a vertebra.

Figure 43:
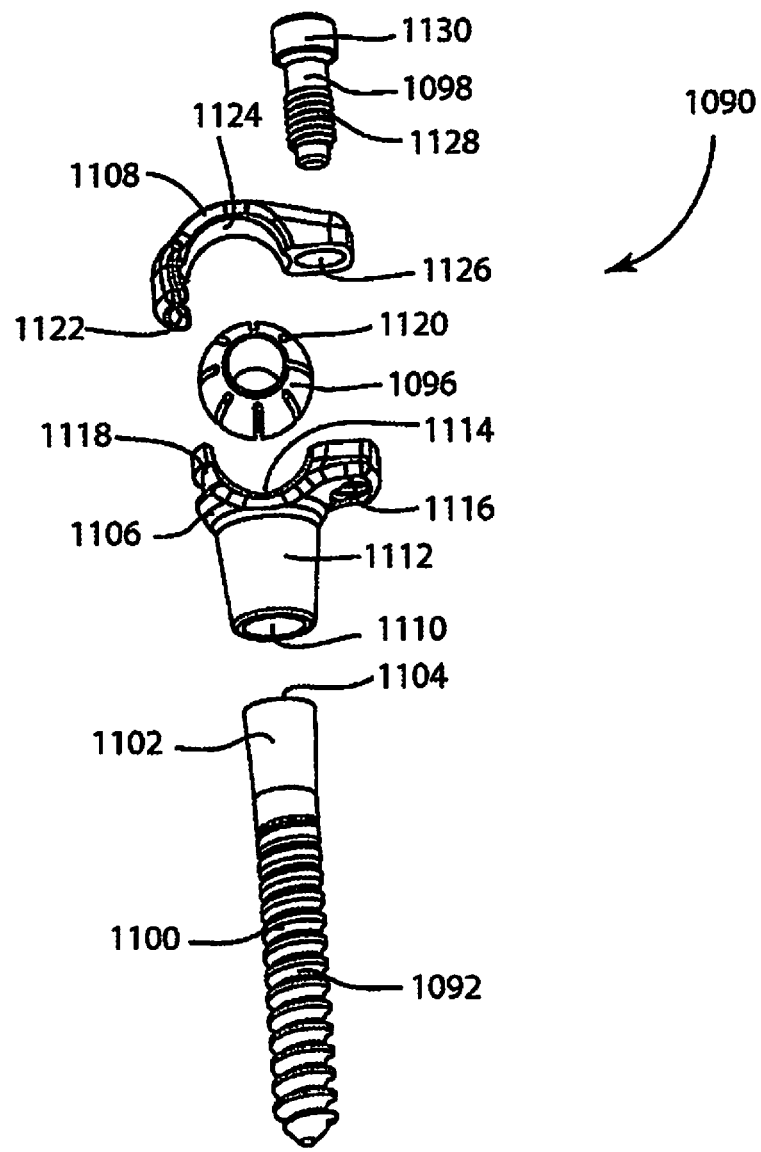
FIG. 43 is an exploded view of the alternate fixation assembly of FIG. 42.

Referring to FIG. 43, an exploded view of fixation assembly 1090 is shown. Fixation member 1092 has a threaded portion 1100 and an attachment portion 1102 which may be tapered. The attachment portion 1102 may include a drive feature 1104 such as a hex drive. The split ring clamp 1094 is of two piece construction, comprising a lower clamp body 1106 and an upper clamp body 1108. The lower clamp body 1106 is cannulated with a bore 1110 which may be tapered, in order to form a tapered connection between fixation member 1092 and lower clamp body portion 1106. Lower clamp body 1106 further comprises an outer surface 1112 which may be a bone ingrowth surface; a spherical pocket 1114 shaped to receive the compression sphere 1096; a threaded lower ring 1116 shaped to receive the set screw 1098; and a linking feature 1118 which may be a groove shaped to mate with a corresponding feature on the upper clamp body 1108. Alternative embodiments of lower clamp body 1106 could include anti-rotation features configured to engage with surrounding bone to prevent rotation of the assembly, including but not limited to fins, teeth, studs, and pins. The compression sphere 1096 is a C-shaped split sphere, and includes a plurality of slits 1120. Upper clamp body 1108 comprises a linking feature 1122 which may be a protrusion, a spherical pocket 1124, and an upper ring 1126. The set screw 1098 comprises a threaded portion 1128 and a head 1130.

Fixation member 1092, coupled with lower clamp body 1106, may be anchored in a prepared pedicle. A lockout tool may be implemented to effect a taper lock between the fixation member and the lower clamp body. The compression sphere 1096 may be coupled with fixation portion of an inferior strut such as strut 1004, or another rod-like member, such that a desired length of the strut extends through the sphere so as to match a vertebral offset. The coupled sphere 1096 and strut are placed in the spherical pocket, and the sphere may be rotated until the strut is at a desired orientation. The upper clamp body 1108 is coupled to the lower clamp body 1106 such that the linking features 1118, 1122 mate and the upper ring 1126 is aligned with the lower ring 1116. The set screw 1098 is inserted through the upper ring 1126 and threaded into the lower ring 1116. As the set screw is actuated, the engagement of the threaded portion 1128 with the threaded lower ring 1116 draws the lower ring upward, and the head 1130 presses down on the upper ring 1126. As the rings 1116, 1126 are thus urged together, the upper and lower clamp bodies 1106, 1108 compress around the compression sphere 1096, which compresses around the strut. Motion of the sphere 1096 and the strut relative to one another and to the remainder of the assembly 1090 is locked out.

Figure 44:
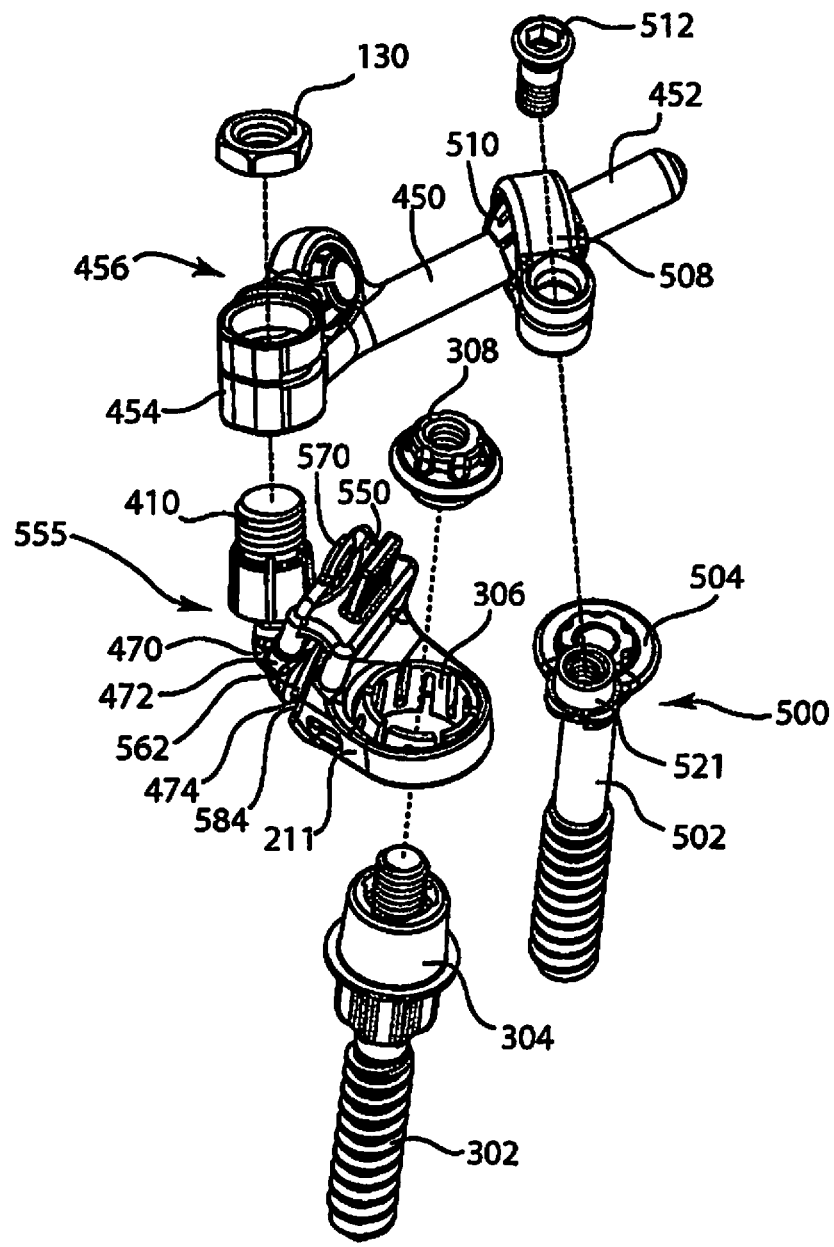
FIG. 44 is a partially exploded perspective view of superior and inferior facet joint implants coupled to the clip of FIG. 17.

Referring to FIG. 44, an alternative method of securing inferior and superior facet joint implants using a coupling clip is illustrated in a partial exploded view. In such an implantation procedure, a fixation member such as fixation member 302 is anchored in a prepared pedicle of a caudal vertebra, and base member 304 is placed on the fixation member. In the adjacent cephalad vertebra, a fixation member such as 502 is implanted in a prepared pedicle and a base such as 504 is coupled to the fixation member. Superior implant 211, split sphere 306, clip 550, inferior body 470, and compressible member 410 may be provided pre-assembled as assembly 555 in a sterile package. Clip 550 secures superior implant 211 to inferior body 470 such that superior articulation surface 584 and inferior articulation surface 474 are in a desired orientation relative to one another. The clip body 552, combined with the rigid superior posts and rigid portions of the inferior posts, provides a rigid feature which holds the superior 584 and inferior 474 articulation surfaces in a fixed alignment. Assembly 555 is placed over fixation member 302 so that sphere 306 fits onto tapered based 304. Superior implant 211, with attached inferior body 470, may be polyaxially adjusted to a preferred orientation relative to fixation member 302 and the caudal vertebra. When a desired orientation is attained, a compression tool may be used to effect a taper lock, as described above with reference to FIG. 6, and set screw 308 is actuated to lock down the assembly 555 to the fixation member 302.

A sphere 510 and split ring clamp 508 are placed on the first end 452, or fixation portion, of inferior strut 450 at a desired linear position. Inferior strut 450 is placed such that its second end 454 encircles compressible member 410, and, generally simultaneously, the split ring clamp 508 on the first end 452 of the strut fits over the pedestal 521 of base member 504. Compressible member 410 may be adjusted relative to inferior body 470, and sphere 510 may be polyaxially rotated to adjust inferior strut 450 relative to base member 504. Optionally, a crosslink such as 108 or 109 (not shown) may be placed in split ring clamp 456. The final position and orientation of the inferior strut 450 is locked out by actuating set screw 512 and nut 130. Plug 570 is removed from clip 550, allowing split ends 562 to deform and contract. Clip 550 is withdrawn from inferior body 470 and superior implant 211, and removed. Once the clip is removed, the superior and inferior implants may articulate along their articular surfaces, allowing a level of natural spinal motion.

Referring to FIG. 45A, an alternate embodiment of a coupling clip is shown. Clip 1200 is of one-piece construction, and is shaped to couple an inferior facet replacement implant such as implant 100 with a superior facet replacement implant such as implant 210. Clip 1200 may retain the implants such that the inferior and superior articulation surfaces are held at a desired relative position. A portion of the clip 1200 is deformable and may be flexed to detach the clip from at least one of the implants.

Clip 1200 comprises a first end 1202 and a second end 1204, and the ends are linked by a connecting portion 1206. First end 1202 comprises a rigid shoulder 1208, and at opposing ends of the rigid shoulder 1208 are a tab 1210 and a post 1212. The tab 1210 and post 1212 are also rigid, and are shaped to couple with and align the inferior and superior implants. A recess 1220 is located on the shoulder 1208. Similarly, second end 1204 comprises a rigid shoulder 1214, tab 1216, post 1218, and recess 1222. Tabs 1210, 1216 are shaped to receive an inferior facet joint implant, and posts 1212, 1218 are shaped to receive a superior facet joint implant. Connecting portion 1206 is deformable, and when it is flexed, first end 1202 rotates about the axis of post 1212, and second end 1204 rotates about the axis of post 1218, such that tabs 1210, 1216 are urged apart.

FIG. 45B is a perspective view of clip 1200 coupled to an inferior facet joint implant 1230. Inferior facet joint implant 1230 is similar to implant 100 seen in FIG. 2, but includes an alternative inferior articular body 1232. Inferior facet joint implant 1230 comprises inferior articular body 1232, conical expander 126, split shell 128 (not visible), split clamp 110, top nut 130, inferior strut 104, and sphere 356 which may be captured in the fixation portion or first end 182 of the inferior strut. Inferior articular body 1232 comprises an inferior articular surface 1234 and a set of slots 1236 which are shaped to receive the tabs 1210, 1216 of the clip 1200. Inferior facet joint implant 1230 may be delivered coupled to clip 1200. Packaging (not shown) may be shaped to prevent connecting portion 1206 from flexing, and to keep posts 1212, 1218 in a fixed position.

Figure 46:
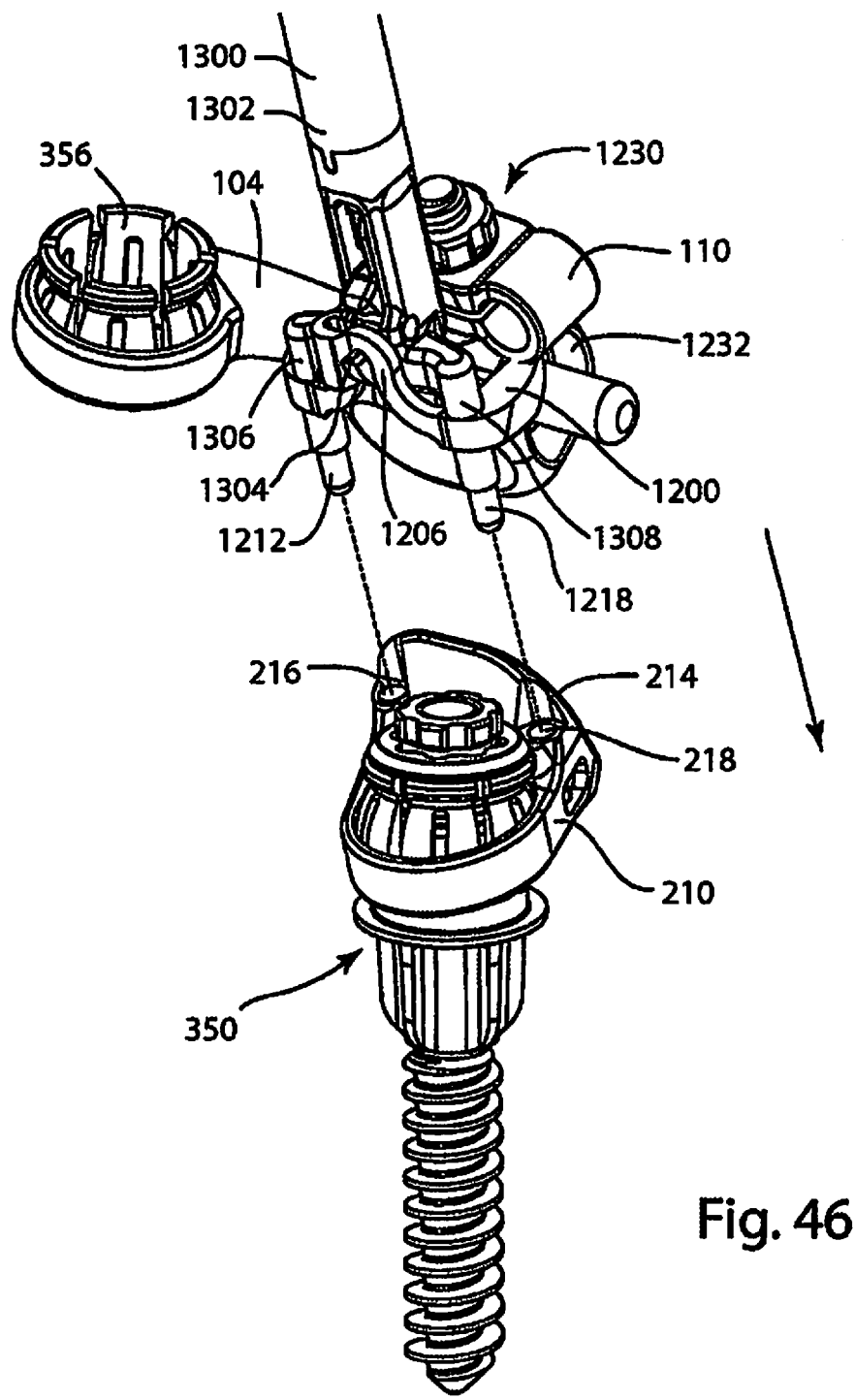
FIG. 46 is a perspective view of the clip and implant of FIG. 45 coupled to a delivery tool, and a superior facet joint implant.

Referring to FIG. 46, clip 1200 and implant 1230 are shown gripped by a delivery tool 1300. Additionally, superior facet implant 1200 is shown coupled to fixation assembly 350. The delivery tool 1300 comprises handles (not shown), a shaft 1302, a hook 1304 which may be actuated to grip and release the clip 1200, and a pair of pegs 1306, 1308. Upon removal of the packaging described above, the delivery tool 1300 may be connected to the clip 1200 via the hook 1304 which hooks on the connection portion 1206, and the pegs 1306, 1308 which protrude into the recesses 1220, 1222. The spacing of the pegs keeps the posts 1212, 1218 of the clip 1200 in a proper position for coupling with the superior implant 210. The hook 1304 may prevent premature flexure of the connection portion 1206. The delivery tool 1300 may be manipulated to position the clip 1200 and implant 1230 such that the posts 1212, 1218 fit into the holes 216, 218 on the superior implant, thus properly aligning the inferior 1234 and superior 214 articulation surfaces relative to one another.

Figure 47:
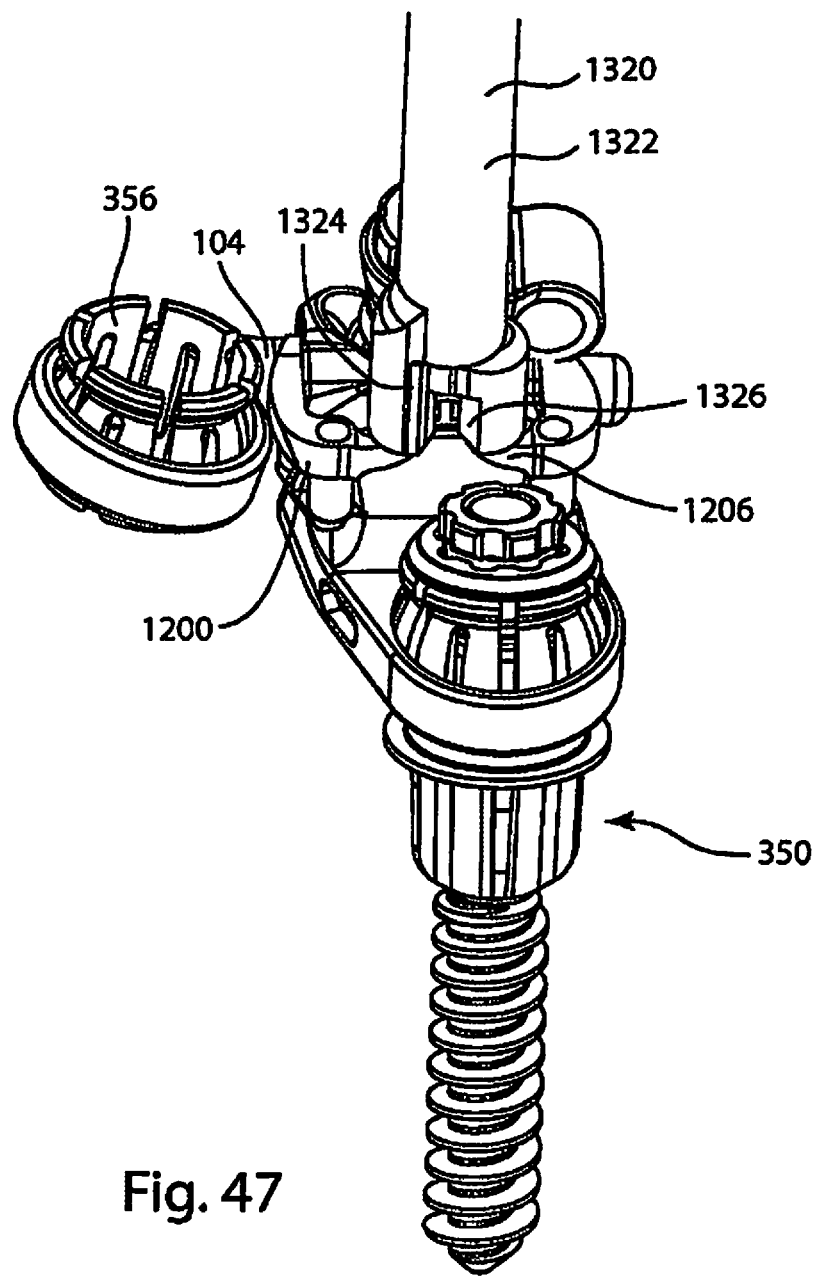
FIG. 47 is a perspective view of the clip and implant of FIG. 45 coupled to a flexing tool, coupled to a superior facet joint implant.

Referring to FIG. 47, a flexing tool 1320 is shown coupled to the connecting portion 1206 of the clip 1200. Flexing tool 1320 is co-axial, and comprises handles (not seen), a shaft 1322, and two gripping features 1324, 1326. The gripping features 1324, 1326 are shaped and positioned to grip two locations on the connecting portion 1206. The flexing tool 1320 may be activated to move the gripping features 1324, 1326 relative to one another such that the connecting portion 1206 is flexed.

Figure 45:
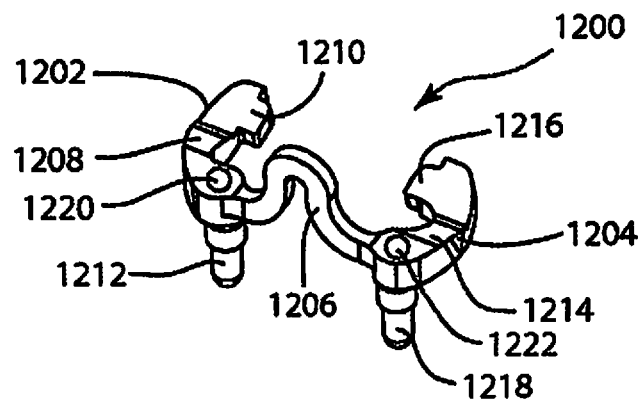
FIG. 45A is a perspective view of an alternate embodiment of a clip.
FIG. 45B is a perspective view of the clip of 45A coupled to an inferior facet joint implant.
Figure 45:
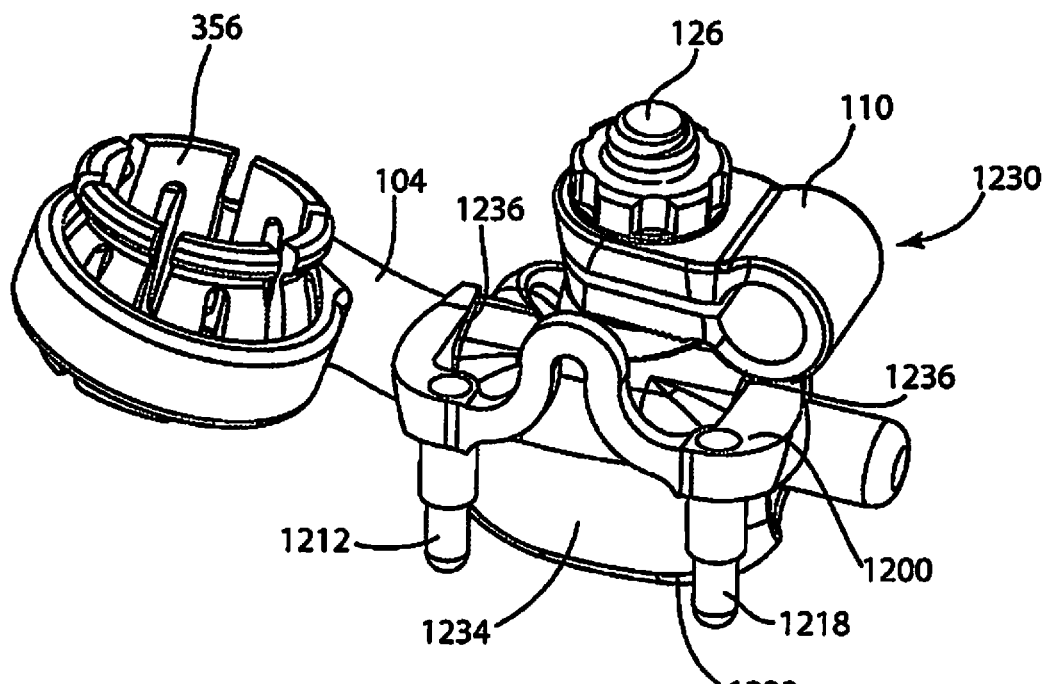

With reference to FIGS. 45-47, one method of implanting inferior facet replacement implant 1230 and superior facet replacement implant 210 is as follows. It is understood that steps may occur in the order presented, or in a different sequence. It is further understood that right and left facet joint replacements may be implanted during the same procedure and optionally linked via a crosslink. Fixation assembly 350 is implanted into a prepared pedicle, and fixation portion or ring 212 of superior implant 210 is positioned and taper-locked onto the fixation assembly, as described previously. A second fixation assembly 350 (not shown) is implanted into the pedicle of the adjacent cephalad vertebra, minus sphere 356, capture nut 358 and top nut 360. Clip 1200 and attached inferior implant 1230 are removed from sterile packaging and coupled to delivery tool 1300. The delivery tool 1300 is manipulated to position sphere 356 onto fixation assembly 350, and posts 1212, 1218 of the clip 1200 into the holes 216, 218 of the superior facet implant 210. As the clip is positioned, polyaxial adjustment may occur at several junctures, allowing adjustment of the inferior articular surface 1234 relative to the fixation assembly 350. Sphere 356 may rotate relative to the fixation assembly 350, the linear position of inferior strut 104 may be adjusted to match the offset distance between the vertebrae, and the split shell 128 may rotate within the inferior articular body 1232. When the clip 1200 is properly positioned so that the posts 1212, 1218 fit into the holes 216, 218 and the articular surfaces 214, 1234 are aligned, the delivery tool 1300 may be triggered to release the clip from the hook 1304, and the delivery tool 1300 is removed. A crosslink such as 108 may be positioned in the split clamp 110. The fixation assembly 350 is taper-locked relative to the sphere 356 and inferior strut 104, and capture nut 358 and top nut 360 are added to secure the assembly. Nut 130 is actuated on conical expander 126 to lock down the relative orientation of inferior strut 104 and inferior articular body 1232, and lock position of crosslink 108. Flexing tool 1320 is attached to the connecting portion 1206 of the clip 1200, and activated to flex the connecting portion. As the connecting portion 1206 of the clip 1200 is flexed, shoulder 1208 rotates relative to the axis of post 1212, and shoulder 1214 rotates relative to the axis of post 1218, and tabs 1210, 1216 are urged apart, and out of slots 1236. Thus, clip 1200 is detached from inferior implant 1230 and also can be urged away from superior implant 210.

The coupling clips disclosed herein may be made in a variety of sizes, and with varied dimensions, to fit implants configured for different vertebral levels. Other embodiments of clips may include different deformable retention features, different alignment features, and/or different features shaped to receive the superior and inferior implants. Coupling clips without deformable features or plugs, and/or with other attachment features are contemplated within the scope of the invention. In addition, trial clips in a variety of sizes and configurations may be provided, to allow the practitioner to choose the correct size or configuration of implant. Trial clips may include integrated superior and/or inferior implant trials. A trial clip and implant may be used to select the proper length of inferior strut to match an offset distance between the vertebrae. Specifically, fixation members and base members may be secured in adjacent vertebrae, and a succession of trials, each comprising a clip retaining an inferior and optionally a superior implant may be positioned on the bases, until the proper length of inferior strut is determined. Then the sterile package containing the proper choice of clip and implants may be opened and the appropriate clip and implants secured to the base members. Use of the trials prevents practitioners from unnecessarily opening more than one sterile package of implants to determine a correct fit.

Figure 48:
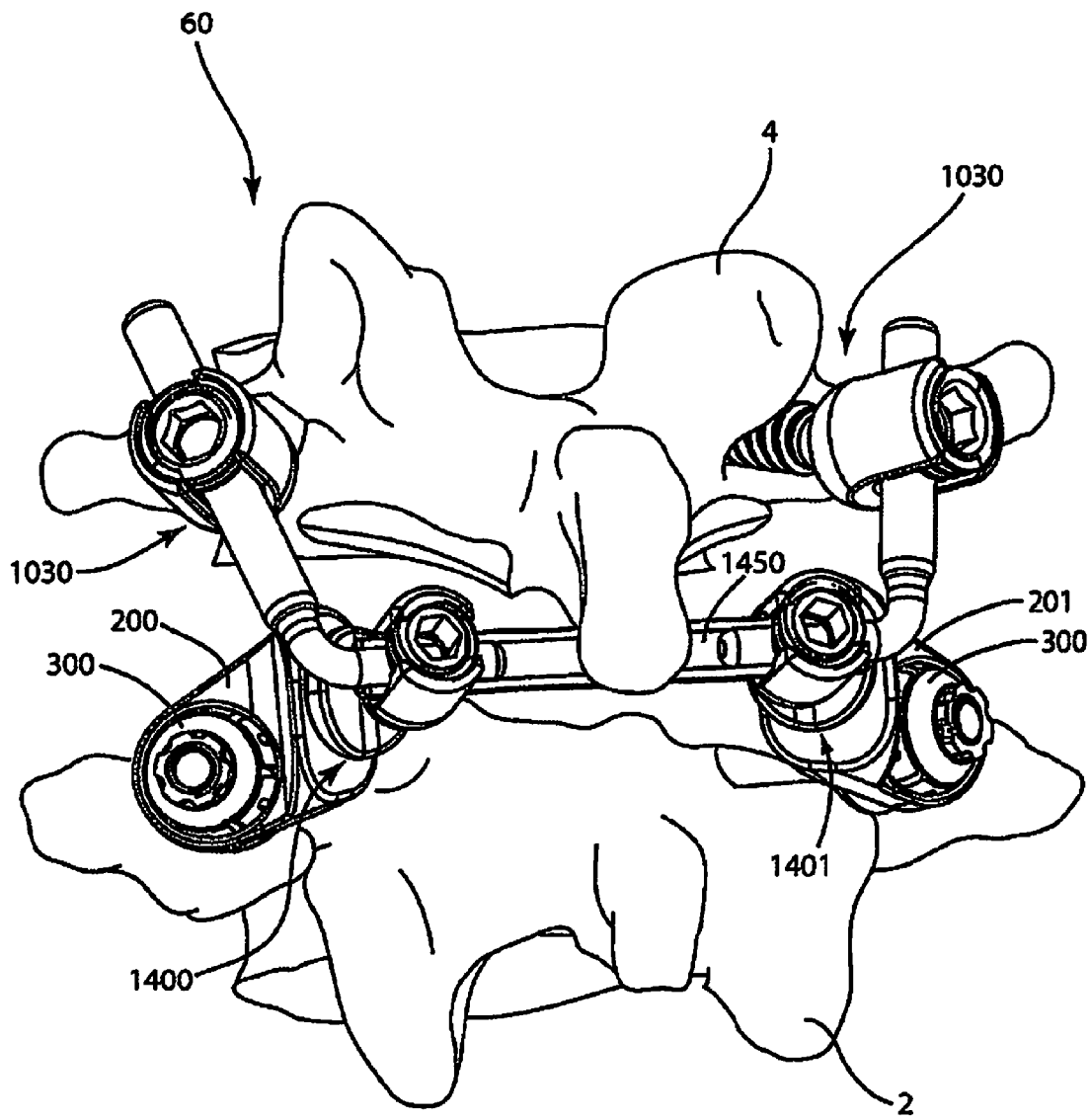
FIG. 48 is a perspective posterior view of a bi-lateral facet joint replacement system with medial-lateral adjustability implant in a portion of a spine.

Referring to FIG. 48, a posterior perspective view shows an alternative embodiment of a bi-lateral facet joint replacement system. System 60 comprises superior facet joint implants 200, 201 each anchored in the caudal vertebra 2 by a fixation assembly 300, and inferior facet joint implants 1400, 1401 each anchored in the cephalad vertebra 4 by a fixation assembly 1030. A crosslink 1450 links implants 1400, 1401. System 60 is configured so that a medial-lateral distance between implants 1400, 1401 is adjustable by sliding the implants along the axis of the crosslink to vary the location of the implants relative to one another. The articular surfaces of the implants 1400, 1401 may also be rotated about the axis of the crosslink and oriented in a polyaxial manner with respect to all other components. Additionally, each inferior strut may be independently rotated relative to the crosslink and the articulation surfaces, and medial-laterally adjusted relative to the crosslink and the articulation surfaces. This high degree of adjustability may allow practitioners to tailor the system to the specific morphology of a patient's spine, including patients with extreme morphology.

Figure 49:
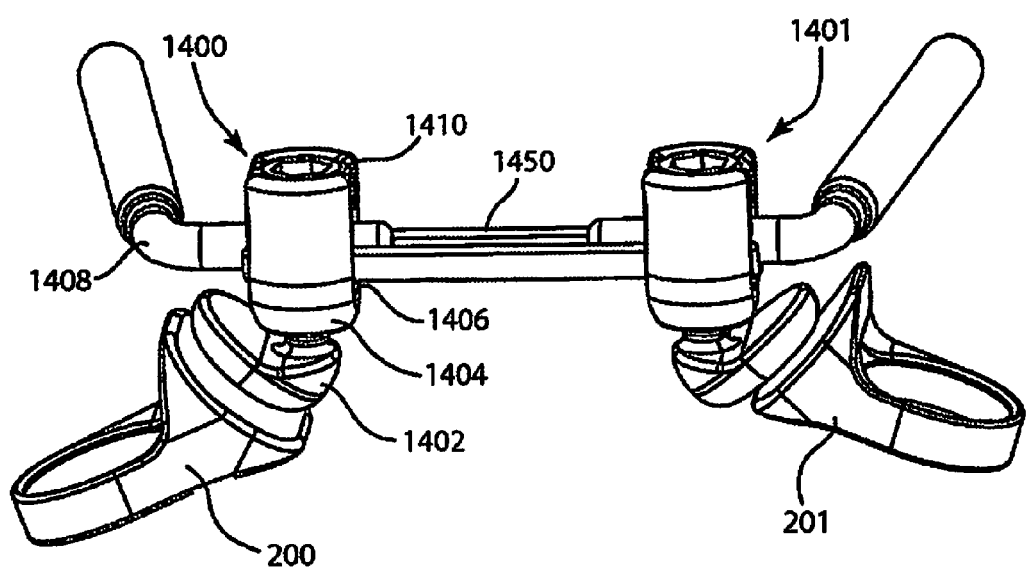
FIG. 49 is a caudal perspective view of a portion of the system of FIG. 48.

FIG. 49 displays a caudal perspective view of implants 1400, 1401, and crosslink 1450. Superior implants 200, 201 are included to show the alignment of the articulation surfaces of the implants. As with previous embodiments, implants on one lateral side will be described and it may be assumed that the other lateral side is a mirror image, unless otherwise specified. Of course, components on either side may vary in size and positioning. It is also noted that an alternative embodiment of the invention could include a system omitting the crosslink 1450.

Figure 50:
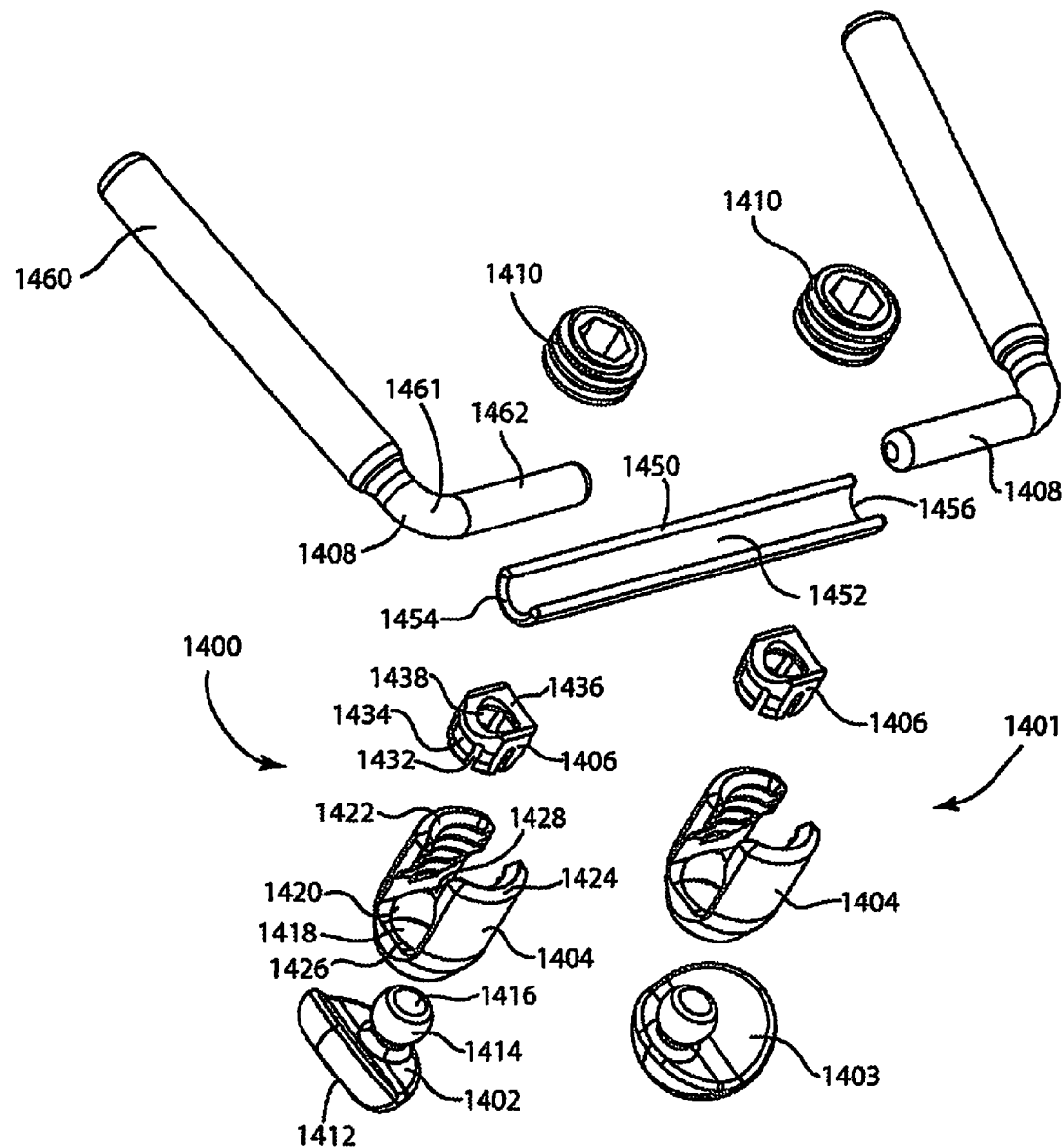
FIG. 50 is an exploded perspective view of a portion of the system of FIG. 48.

Referring to FIG. 50, an exploded view of implants 1400, 1401 and crosslink 1450 are shown. Inferior facet joint replacement implant 1400 comprises an inferior articulation body 1402, a coupling body which may be a tulip body 1404, compressible member 1406, inferior strut 1408, and set screw 1410. Inferior articular body 1402 comprises an inferior articulation surface 1412 and a spherical member 1414. The spherical member 1414 is polyaxially rotatable within the compressible member 1406 and the tulip body 1404 prior to lockout, so that the inferior articulation surface 1412 may be aligned at a desired orientation. The spherical member 1414 may or may not comprise a flattened section 1416 for clearance.

The tulip body 1404 is generally U-shaped. A rounded cavity 1418, sized and shaped to receive the compressible member 1406, is partially enclosed by a concave wall 1420. Two opposably oriented sidewalls 1422, 1424 extend posteriorly from the concave wall. A portion of the interior surfaces of the sidewalls are threaded to receive the set screw 1410. Two opposably oriented saddles 1426, 1428 are formed posterior to the concave wall 1420 and between the sidewalls 1422, 1424.

The compressible member 1406 comprises an interior cavity 1432 partially enclosed by a plurality of fingers 1434. A trough 1436 extends across the compressible member 1406 posterior to the interior cavity 1432, and an opening 1438 may or may not connect the trough 1436 to the interior cavity. The interior cavity 1432 is shaped to receive the spherical member 1414. The outer surface of the fingers 1434 are sized and shaped to deflect inward as the member is pressed in an anterior direction through the cavity 1418 of the tulip body 1404. Additionally, the outer surface of the compressible member is shaped such that the trough 1436 maintains alignment with the saddles 1426, 1428 of the tulip body 1404.

The crosslink 1450 is shaped as a longitudinally split cylinder. It comprises a half-pipe body 1452 with a first end 1454 and a second end 1456. The half-pipe body 1452 is sized and shaped to be received in the trough 1436 of the compressible member 1406, and sized and shaped to receive a portion of each inferior strut 1408.

The inferior strut 1408 comprises a fixation portion, or first end 1460 and a second end 1462 connected by a transition portion 1461. The strut 1408 is generally L-shaped with the first and second ends at approximate right angles relative to one another, although other embodiments could include struts with angles of more or less than 90 degrees or struts that may be bent to the desired angle. The first end 1460 is cylindrical, sized and shaped to be received by fixation assembly 1030. The second end 1462 is sized and shaped to be received in the half-pipe body 1452.

Figure 51:
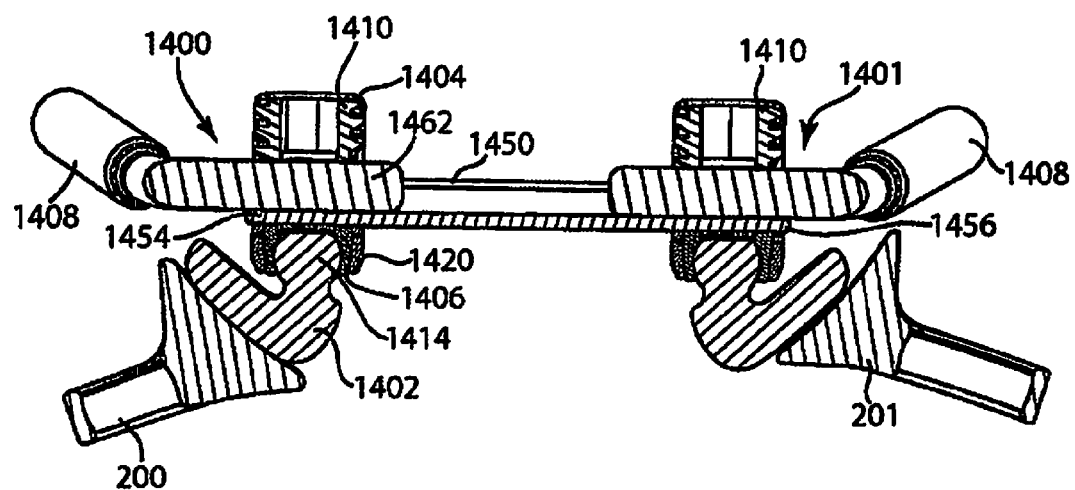
FIG. 51 is a caudal partial cross-sectional view of a portion of the system of FIG. 48.

FIG. 51 is a partial cross-sectional caudal view of inferior implants 1400, 1401, superior implants 200, 201, and crosslink 1450. Referring to FIGS. 48 and 51, one method of implanting system 60 into a portion of a spine may be as follows. Fixation assemblies 300 and superior implants 200, 201 are implanted in the caudal vertebra 2 and locked out, as described previously. The pedicle screw and tulip portions of fixation assemblies 1030 are anchored in the cephalad vertebra 4. Implants 1400 and 1401, minus their respective inferior struts, are positioned so that their inferior articular surfaces are aligned with the superior articular surfaces of implants 200 and 201 at a desired orientation and temporarily held together. Positioning the implants 1400, 1401 may comprise polyaxially adjusting the spherical members and attached articular surfaces, and/or translating the inferior articular surfaces along the medial-lateral axis of the caudal 2 and cephalad 4 vertebrae. Alternatively, the inferior facet implants 1400, 1401 may be temporarily attached to the superior facet implants 200, 201 in the desired orientation allowing opposing articulating surfaces to be implanted together. The crosslink may be inserted from a posterior approach into the tulip body 1404 of implant 1400 and maneuvered until the first end 1454 of the crosslink is within the saddles 1426, 1428 and contacting the trough 1436 of the compression member 1406. The crosslink may then be slid through the hole in the spinous process or interspinous process tissue until the second end 1456 is within the saddles of the tulip body 1404 of implant 1401 and contacting the trough 1436 of the compression member 1406. Alternatively, the crosslink 1450 may be dropped down into both tulips at the same time if there is no bone or tissue in the way. The crosslink 1450 is then rotated about its longitudinal axis until the rounded outer wall of the half-pipe body 1452 rests in the saddles of both tulip bodies and contacts the troughs 1436 of the compression members 1406. In this position, the crosslink 1450 may not pop posteriorly out of the tulip bodies, but may be slidably adjustable along the medial-lateral axis.

With the crosslink 1450 spanning the tulip bodies 1404 as described, the inferior struts 1408 may be placed in the system, one on each lateral side. The left inferior strut is placed so that its second end 1462 is received in the first end 1454 of the crosslink 1450, and the right inferior strut is placed so that its second end 1462 is received in the second end 1456 of the crosslink. Trial inferior struts in a variety of sizes may be provided to aid in determining proper strut size. Once the proper size of inferior strut is chosen, each appropriately sized strut is placed in the crosslink and may be slidably adjusted along the medial-lateral axis of the crosslink and rotated about that axis. Each strut is rotated until its first end 1460 is received in the saddles 1038 of the capture member 1034 of its respective fixation assembly 1030. The struts may also be adjustable along the cephalad-caudal axis of the vertebrae. Until lockdown, the capture members 1034 may be polyaxially rotated to desired positions to receive and adjust the inferior struts 1408.

Once the struts 1408 are placed and adjusted, the set screws 1410 are actuated in the tulip bodies 1404 to lock out motion of the spherical members 1414, crosslink 1450, and struts 1408. As set screw 1410 is tightened, its threads engage with the threaded inner walls of sidewalls 1422, 1424. The tulip body 1404 is drawn posteriorly or "upward" and the set screw moves anteriorly or "downward". This opposing motion compresses together the first end 1462 of the inferior strut, the crosslink 1450, and the compressible member 1406, locking out their motion. The fingers 1434 of the compressible member 1406 are urged together by the concave wall 1420 of the tulip body, in turn compressing the compressible member about the spherical member 1414, and locking out motion of the inferior articular body 1402. Set screws 1036 are actuated in the capture members 1034 to lock out motion in the fixation assemblies 1030. The inferior facet implants 1401 and 1402 are then allowed to articulate against their respective superior facet implants 200 and 201 by removing any temporary holding device.

Referring to FIG. 51, it is noted that the orientation of inferior implant 1400 relative to superior implant 200 is not the same as the orientation of inferior implant 1401 relative to superior implant 201, however there is enough adjustability to allow them to have similar alignments. It is appreciated that the medial-lateral and rotatable adjustability of the tulip bodies 1404 and the struts 1408, along with the polyaxial adjustability of the inferior articular body 1402, allow for precise yet differing orientation of the implants relative to one another. This adjustability, along with the adjustability in the fixation assemblies 1030 connecting the first end 1460 of the struts 1408, allow the system 60 to be adjusted to a full range of vertebral morphologies.

The present invention includes variances of the systems herein described. Alternative embodiments may include different geometries and intermediate parts. Changes in the geometry, especially on the ends of the inferior strut, could be made to facilitate instrumentation or overall function. It is appreciated that various features of the above-described examples can be mixed and matched to form a variety of other alternatives. For example, a strut, fusion rod or other rod-like member may be anchored or locked down by any of the fixation assemblies herein disclosed. Applications of the present invention may include single- or multi-level facet joint replacement with motion preservation, or other iterations in which a rod or rod-like member is fixed to a second member to attain spinal fusion.

The present invention may be embodied in other specific forms without departing from its spirit or essential characteristics. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A surgical method comprising:
   inserting an implantation system into a patient, wherein the implantation system comprises:
   a left fixation member implantable in a first vertebra;
   a left strut operably connected to the left fixation member
   a right fixation member implantable in the first vertebra;
   a right strut operably connected to the right fixation member; and
   a crosslink, wherein the crosslink receives the left strut in a slot formed through the crosslink and the right strut in the slot formed through the crosslink,
   wherein the implantation system further comprises a coupling body for receiving the left strut and the coupling body therein.

2. The surgical method of claim 1, wherein the left strut is bent.

3. The surgical method of claim 2, wherein the left strut comprises an L-shape.

4. The surgical method of claim 1, wherein the crosslink comprises a half-pipe body.

5. The surgical method of claim 1, wherein the implantation system further comprises a compressible member received in the coupling body, wherein the compressible member comprises a trough for receiving the crosslink.

6. The surgical method of claim 5, wherein the compressible member comprises a plurality of fingers.

7. The surgical method of claim 1, wherein the implantation system further comprises an articular body received in the coupling body.

8. The surgical method of claim 7, wherein the articular body is attached to a spherical member that is received in the coupling body.

9. The surgical method of claim 1, wherein the implantation system further comprises a coupling body and a set screw, wherein the coupling body receives the crosslink, the left strut and the set screw therein.

10. A surgical method comprising:
    inserting an implantation system into a patient, wherein the implantation system comprises:
    a left fixation member implantable in a first vertebra;
    a left strut operably connected to the left fixation member
    a right fixation member implantable in the first vertebra;
    a right strut operably connected to the right fixation member;
    a crosslink, wherein the crosslink receives the left strut in a slot formed through the crosslink and the right strut in the slot formed through the crosslink;
    a left coupling body for receiving the left strut and the crosslink therein; and
    a right coupling body for receiving the right strut and the crosslink therein.

11. The surgical method of claim 10, wherein the left strut is bent.

12. The surgical method of claim 11, wherein the left strut comprises an L-shape.

13. The surgical method of claim 10, wherein the crosslink comprises a half-pipe body.

14. The surgical method of claim 10, wherein the implantation system further comprises a compressible member received in the left coupling body, wherein the compressible member comprises a trough for receiving the crosslink.

15. The surgical method of claim 14, wherein the left coupling body further comprises one or more fingers extending downwardly therefrom.

16. The surgical method of claim 10, wherein the left coupling body is tulip-shaped.

17. The surgical method of claim 16, wherein the left coupling body receives an articulation body therein.

18. The surgical method of claim 17, wherein the articulation body comprises a spherical member.

19. The surgical method of claim 18, wherein the left coupling body receives a compressible member over the spherical member of the articulation body.

\* \* \* \* \*